US011453670B2

(12) United States Patent
Li et al.

(10) Patent No.: US 11,453,670 B2
(45) Date of Patent: Sep. 27, 2022

(54) SUBSTITUTED HETEROCYCLE FUSED GAMMA-CARBOLINES SYNTHESIS

(71) Applicant: INTRA-CELLULAR THERAPIES, INC., New York, NY (US)

(72) Inventors: Peng Li, New Milford, NJ (US); Qiang Zhang, Plainsboro, NJ (US)

(73) Assignee: INTRA-CELLULAR THERAPIES, INC., New York, NY (US)

( * ) Notice: Subject to any disclaimer, the term of this patent is extended or adjusted under 35 U.S.C. 154(b) by 0 days.

(21) Appl. No.: 16/438,163

(22) Filed: Aug. 16, 2019

(65) Prior Publication Data

US 2020/0102309 A1  Apr. 2, 2020

Related U.S. Application Data

(60) Provisional application No. 62/780,742, filed on Dec. 17, 2018, provisional application No. 62/683,411, filed on Jun. 11, 2018.

(51) Int. Cl.
*C07D 471/16* (2006.01)
*C07D 519/00* (2006.01)

(52) U.S. Cl.
CPC ......... *C07D 471/16* (2013.01); *C07D 519/00* (2013.01)

(58) Field of Classification Search
CPC .................................................. C07D 471/16
See application file for complete search history.

(56) References Cited

U.S. PATENT DOCUMENTS

| | | |
|---|---|---|
| 2,490,813 A | 12/1949 | Hughes et al. |
| 3,299,078 A | 1/1967 | Pachter |
| 3,813,392 A | 5/1974 | Sellstedt et al. |
| 3,914,421 A | 10/1975 | Rajagopalan |
| 4,001,263 A | 1/1977 | Plattner et al. |
| 4,115,577 A | 9/1978 | Rajagopalan |
| 4,183,936 A | 1/1980 | Rajagopalan |
| 4,219,550 A | 8/1980 | Rajagopalan |
| 4,238,607 A | 12/1980 | Rajagopalan |
| 4,522,944 A | 6/1985 | Doria et al. |
| 4,530,840 A | 7/1985 | Tice et al. |
| 4,971,971 A | 11/1990 | Tokunaga et al. |
| 4,985,432 A | 1/1991 | Tokunaga et al. |
| 5,004,602 A | 4/1991 | Hutchinson |
| 5,114,976 A | 5/1992 | Norden |
| 5,151,419 A | 9/1992 | Perenyi et al. |
| 5,538,739 A | 7/1996 | Bodmer et al. |
| 5,576,460 A | 11/1996 | Buchwald et al. |
| 5,648,539 A | 7/1997 | Goodbrand et al. |
| 5,648,542 A | 7/1997 | Goodbrand et al. |
| 5,654,482 A | 8/1997 | Goodbrand et al. |
| 5,705,697 A | 1/1998 | Goodbrand et al. |
| 5,723,669 A | 3/1998 | Goodbrand et al. |
| 5,723,671 A | 3/1998 | Goodbrand et al. |
| 5,847,166 A | 12/1998 | Buchwald et al. |
| 5,902,901 A | 5/1999 | Goodbrand et al. |
| 5,992,338 A | 7/1999 | Brich et al. |
| 6,043,370 A | 3/2000 | Kubo et al. |
| 6,166,226 A | 12/2000 | Buchwald et al. |
| 6,235,936 B1 | 5/2001 | Buchwald et al. |
| 6,307,087 B1 | 10/2001 | Buchwald et al. |
| 6,323,366 B1 | 11/2001 | Wolfe et al. |
| 6,395,916 B1 | 5/2002 | Buchwald et al. |
| 6,407,092 B1 | 6/2002 | Hester et al. |
| 6,465,693 B2 | 10/2002 | Buchwald et al. |
| 6,541,639 B2 | 4/2003 | Zhou et al. |
| 6,544,599 B1 | 4/2003 | Mesens et al. |
| 6,548,493 B1 | 4/2003 | Robichaud et al. |
| 6,552,017 B1 | 4/2003 | Robichaud et al. |
| 6,699,852 B2 | 3/2004 | Robichaud et al. |
| 6,713,471 B1 | 3/2004 | Robichaud et al. |
| 6,759,554 B2 * | 7/2004 | Buchwald ............. C07C 249/02 564/407 |
| 6,762,329 B2 | 7/2004 | Marcoux et al. |
| 6,849,619 B2 | 2/2005 | Robichaud et al. |
| 6,867,298 B2 | 3/2005 | Buchwald et al. |
| 6,888,032 B2 | 5/2005 | Buchwald et al. |
| 6,929,803 B2 | 8/2005 | Wong et al. |
| 6,946,560 B2 | 9/2005 | Buchwald et al. |
| 7,026,498 B2 | 4/2006 | Buchwald et al. |
| 7,071,186 B2 | 7/2006 | Robichaud et al. |
| 7,081,455 B2 | 7/2006 | Robichaud et al. |
| 7,109,339 B2 | 9/2006 | Lee et al. |
| 7,115,784 B2 | 10/2006 | Buchwald et al. |
| 7,183,282 B2 | 2/2007 | Robichaud et al. |
| 7,223,870 B2 | 5/2007 | Ghosh et al. |

(Continued)

FOREIGN PATENT DOCUMENTS

| | | |
|---|---|---|
| GB | 1476087 | 6/1977 |
| WO | WO 2000/064899 | 11/2000 |

(Continued)

OTHER PUBLICATIONS

U.S. Environmental Protection Agency TSCA "Chemical Data Reporting Fact Sheet: Non-lsolated Intermediates" Apr. 2016.*
Anderson "Practical Process Research and Development" 2000, p. 34.*
Surry "Diamine ligands in copper-catalyzed reactions." Chemical Science 2010, 1, 13-31.*
Huang "Efficient Copper-Promoted N-Arylations of Aryl Halides with Amines" J. Comb. Chem. 2008, 10, 617-619.*
Avendano, C., et al., "The problem of the existence of C(Ar)-H . . . N Intramolecular Hydrogen Bonds in a Family of 9-Azaphenyl-9H-carbazoles," J. Chem. Soc. Perkin Trans., vol. 2, p. 1547-1555, (1993).
Balbach, et al. "Pharmaceutical evaluation of early development candidates 'the 100 mg-approach'", International Journal of Pharmaceutics, vol. 275, pp. 1-12 (2004).

(Continued)

*Primary Examiner* — David K O'Dell
(74) *Attorney, Agent, or Firm* — Hoxie & Associates LLC

(57) ABSTRACT

The present invention provides improved methods for the preparation of substituted heterocycle fused gamma-carbolines, intermediates useful in producing them and methods for producing such intermediates and such heterocycle fused gamma-carbolines.

28 Claims, 2 Drawing Sheets

(56) References Cited

U.S. PATENT DOCUMENTS

| | | | |
|---|---|---|---|
| 7,223,879 | B2 | 5/2007 | Buchwald et al. |
| RE39,679 | E | 6/2007 | Robichaud et al. |
| RE39,680 | E | 6/2007 | Robichaud et al. |
| 7,238,690 | B2 | 7/2007 | Robichaud et al. |
| 7,247,731 | B2 | 7/2007 | Buchwald et al. |
| 7,323,608 | B2 | 1/2008 | Buchwald et al. |
| 7,375,226 | B2 | 5/2008 | Jolidon et al. |
| 7,462,641 | B2 | 12/2008 | Igo et al. |
| 7,592,454 | B2 | 9/2009 | Lee et al. |
| 7,998,971 | B2 | 8/2011 | Barlow et al. |
| 8,309,722 | B2 | 11/2012 | Tomesch et al. |
| 8,598,119 | B2 | 12/2013 | Mates et al. |
| 8,648,077 | B2 | 2/2014 | Tomesch et al. |
| 8,779,139 | B2 | 7/2014 | Tomesch et al. |
| 8,993,572 | B2 | 3/2015 | Mates et al. |
| 9,168,258 | B2 | 10/2015 | Mates et al. |
| 9,199,995 | B2 | 12/2015 | Tomesch et al. |
| 9,315,504 | B2 | 4/2016 | Tomesch et al. |
| 9,371,324 | B2 | 6/2016 | Mates et al. |
| 9,393,192 | B2 | 7/2016 | Yam et al. |
| 9,428,506 | B2 | 8/2016 | Mates et al. |
| 9,586,960 | B2 | 3/2017 | Tomesch et al. |
| 9,616,061 | B2 | 4/2017 | Mates et al. |
| 9,708,322 | B2 | 7/2017 | Peng et al. |
| 9,745,300 | B2 | 8/2017 | Mates et al. |
| 9,751,883 | B2 | 9/2017 | Tomesch et al. |
| 9,956,227 | B2 | 5/2018 | Vanover et al. |
| 10,072,010 | B2 | 9/2018 | Li et al. |
| 10,077,267 | B2 | 9/2018 | Mates et al. |
| 10,117,867 | B2 | 11/2018 | Mates et al. |
| 10,221,176 | B2 * | 3/2019 | Tomesch ............... A61P 15/00 |
| 10,245,260 | B2 | 4/2019 | Yao et al. |
| 10,322,134 | B2 | 7/2019 | Vanover et al. |
| 10,472,359 | B2 | 11/2019 | Li et al. |
| 10,597,395 | B2 * | 3/2020 | Tomesch ............. C07D 471/16 |
| 10,688,097 | B2 | 6/2020 | Yao et al. |
| 10,702,522 | B2 | 7/2020 | Mates et al. |
| 10,799,500 | B2 | 10/2020 | Yao et al. |
| 10,844,061 | B2 | 11/2020 | Li et al. |
| 10,960,009 | B2 | 3/2021 | Vanover et al. |
| 10,960,010 | B2 | 3/2021 | Vanover et al. |
| 11,026,951 | B2 | 6/2021 | Mates et al. |
| 2001/0008942 | A1 | 7/2001 | Buchwald et al. |
| 2004/0034015 | A1 | 2/2004 | Robichaud et al. |
| 2004/0127482 | A1 | 7/2004 | Robichaud et al. |
| 2004/0186094 | A1 | 9/2004 | Robichaud et al. |
| 2004/0220178 | A1 | 11/2004 | Robichaud et al. |
| 2005/0182749 | A1 | 8/2005 | Matsui |
| 2005/0239768 | A1 | 10/2005 | Lee et al. |
| 2006/0128713 | A1 | 6/2006 | Jolidon et al. |
| 2015/0072964 | A1 | 3/2015 | Mates et al. |
| 2015/0080404 | A1 | 3/2015 | Mates et al. |
| 2016/0194326 | A1 | 7/2016 | Tomesch et al. |
| 2019/0112309 | A1 | 4/2019 | Peng et al. |
| 2019/0231780 | A1 | 8/2019 | Yao et al. |
| 2020/0102309 | A1 | 4/2020 | Li et al. |
| 2021/0070755 | A1 | 3/2021 | Berecz et al. |

FOREIGN PATENT DOCUMENTS

| | | |
|---|---|---|
| WO | WO 2000/077001 | 12/2000 |
| WO | WO 2000/077002 | 12/2000 |
| WO | WO 2000/077010 | 12/2000 |
| WO | WO 2002/085838 | 10/2002 |
| WO | WO 2004/013094 | 2/2004 |
| WO | WO 2004/039788 | 5/2004 |
| WO | WO 2004/056324 | 7/2004 |
| WO | WO 2008/112280 | 9/2008 |
| WO | WO 2009/114181 | 9/2009 |
| WO | WO 2009/145900 | 12/2009 |
| WO | WO 2013/155504 | 10/2013 |
| WO | WO 2013/155506 | 10/2013 |
| WO | WO 2014/145192 | 9/2014 |
| WO | WO 2015/085004 | 6/2015 |
| WO | WO 2015/154025 | 10/2015 |
| WO | WO 2017/165843 | 9/2017 |
| WO | WO 2019/102240 | 5/2019 |
| WO | WO 2019/183546 | 9/2019 |
| WO | WO 2020/131895 | 6/2020 |
| WO | WO 2020/131911 | 6/2020 |

OTHER PUBLICATIONS

Bastin, "Salt Selection and Optimized Procedures for Pharmaceutical New Chemical Entities", Organic Process and Research Development, vol. 4, No. 5, pp. 427-435 (2000).

Berger et al. "Synthesis of some conformationally restricted analogs of fentanyl." Journal of Medicinal Chemistry, vol. 20, No. 4, p. 600-602, (1977).

Boger, D., et al. J. Org. Chem., vol. 50, pp. 5782-5789, (1985).

Bowman, W.R., "Synthesis of 1H-quinazoline-4-ones using intramolecular aromatic nucleophilic substitution," ARKIVOC, vol. x, p. 434-442, (2003).

Bowman, W.R., et al., "Intramolecular Aromatic Substitution (SRN1) Reactions—Use of Entrainment for the Preparation of Benzothiazoles," Tetrahedron Letters, vol. 23, p. 5093-5096, (1982).

Bowman, W.R., et al., Tetrahedron Letters, vol. 25, p. 5821-5824, (1984).

Byrn, "Pharmaceutical Solids: A Strategic Approach to Regulatory Considerations", vol. 12, No. 7, p. 945-954 (1995).

Crawford, K.R., et al., Tetrahedron Letters, vol. 43, p. 7365-7368, (2002).

Evindar, G., et al., Organic Letters, vol. 5, No. 2, p. 133-136, (2003).

Ezquerra, J., et al., J. Org. Chem., vol. 61, p. 5804-5812, (1996).

Fee, W.W., et al., "Copper (II)-promoted solvolyses of nickel (II) complexes III. Tetradentate Schiff base ligands containing various diamine segments," Aust. J. Chem., vol. 26, p. 1475-1485, (1973).

Ferreira, I., et al., Tetrahedron, vol. 58, p. 7943-7949, (2002).

Finet, J-P., et al., "Recent advances in ullmann reaction: copper(II) diacetate catalysed N-,)- and S-arylation involving polycoordinate heteroatomic derivatives," Current Organic Chemistry, vol. 6, p. 597-626, (2002).

Goodbrand, H.B., et al., "Ligand-Accelerated catalysis of the Ullmann condensation: Application to hole conducting triarylamines," J. Org. Chem., vol. 64, p. 670-674, (1999).

Grant, "Polymorphism in Pharmaceutical Solids", Chapter 1, pp. 1-10 (1999).

Guillory, "Polymorphism in Pharmaceutical Solids", Chapter 5, pp. 183-226 (1999).

Hackman, et al. JAMA, 296(14), 2006, 1731-1732.

Hamann, B.C., et al., J. Am. Chem. Soc. vol. 120, p. 2694-2703, (1998).

Hartwig, J., "Palladium-catalyzed amination of aryl halides: Mechanism and rational catalyst design," Synlett, p. 329-340, (1996).

Hassan, J., et al., "Aryl-aryl bond formation one century after the discovery of the ullmann reaction," Chem. Rev., vol. 102, p. 1359-1469, (2002).

Haynes, "Occurrence of Pharmaceutically Acceptable Anions and Cations in the Cambridge Database", Journal of Pharmaceutical Sciences, vol. 94, No. 10, pp. 2111-2120 (2005).

Ito, T., & Watanabe, K., "Studies of organic catalytic reactions. VI. The function of pyridine and copper in the Rosenmund-von Braun reaction," Bulletin of the Chemical Society of Japan, vol. 41, p. 419-423, (1968).

Jain et al., "Polymorphism in Pharmacy", Indian Drugs, 23(6), 315-316 (1986).

Ji, J., et al., "Selective amination of polyhalopyridines catalyzed by a palladium-xantphos complex," Organic Letters, vol. 5, No. 24, p. 4611-4614, (2003).

Jordan, V.C. Nature Reviews: Drug Discovery, 2, 2003, 205.

Kametani, T., et al., Heterocycles, vol. 14, No. 3, p. 277-280, (1980).

Kang, S-K., et al., "Copper-catalyzed N-arylation of aryl iodides with benzamides or nitrogen heterocycles in the presence of ethylendiamine," Synlett, No. 3, p. 427-430, (2002).

(56) References Cited

OTHER PUBLICATIONS

Kiyomori, A., et al., "An efficient copper-catalyzed coupling of aryl halides with imidazoles," Tetrahedron Letters, vol. 40, p. 2657-2660, (1999).
Klapars, A., et al., "A general and efficient copper catalyst for the amidation of aryl halides and the N-arylation of nitrogen heterocycles," J. Am. Chem. Soc., vol. 123, p. 7727-7729, (2001).
Klapars, A., et al., "A general and efficient copper catalyst for the amidation of aryl halides," J. Am. Chem. Soc., vol. 124, p. 7421-7428, (2002).
Kondratov, S.A., et al., "Nucelophilic substitution in the aromatic series. Lv. Reaction of o-nitrochlorobenzene with ammonia in the presence of copper compounds," Zhurnal Organidreskoi Khimii, vol. 51, No. 11, p. 2387-2390, (1979).
Kwong, F.Y., et al., "Mild and efficient copper-catalyzed amination of aryl bromides with primary alkylamines," Organic Letters, vol. 5, No. 6, p. 793-796, (2003).
Li et al., "Discovery of a Tetracyclic Quinoxaline Derivative as a Potent and Orally Active Multifunctional Drug Candidate for the Treatment of Neuropsychiatric and Neurological Disorders", vol. 57, pp. 2670-2682 (2014).
Li et al., "Dopamine Targeting Drugs for the Treatment of Schizophrenia: Past, Present and Future," Current Topics in Medicinal Chemistry, vol. 16, pp. 3385-3403 (2016).
Lee, T., et al. "Novel, Highly Potent, Selective 5-HT2A/D2 Receptor Antagonists as Potential Atypical Antipsychotics," Bioorg. Med. Chem. Lett. vol. 13, p. 767-770, (2003).
Louie, J., et al., Tetrahedron Letters, vol. 36, No. 21, pp. 3609-3612, (1995).
Marcoux, J-F., et al., "A general copper-catalyzed synthesis of diaryl ethers," J. Am. Chem. Soc., vol. 119, p. 10539-10540, (1997).
Murakami, Y., et al., Chem. Pharm. Bull, vol. 43, No. 8, p. 1281-1286, (1995).
Newman et al., "Solid-state analysis of the active pharmaceutical ingredient in drug products", *Drug Discovery Today*, vol. 8, No. 9, 898-903 (2003).
Protective Groups in Organic Synthesis, Third Edition, John Wiley & Sons, Inc., p. 494-505, (1999).
Rackova et al. "Free Radical Scavenging and Antioxidant Activities of Substituted Hexahydropyridoindoles. Quantitative Structure-Activity Relationships." Journal of Medicinal Chemistry, vol. 49, No. 8, p. 2543-2548, (2006).
Sadighi, J.P., et al., "A highly active palladium catalyst system for the arylation of anilines," Tetrahedron Letters, vol. 39, p. 5327-5330, (1998).
Savjani et al., "Drug Solubility: Importance and Enhancement Techniques", International Scholarly Research Network Pharmaceutics (2012), vol. 2012, pp. 1-10.
Sigel. H., et al., Inorganic Chemistry, vol. 13, No. 2, p. 462-465, (1974).
Singhal et al., "Drug polymorphism and dosage form design: a practical perspective", Advanced Drug Delivery Reviews, vol. 56, pp. 335-347 (2004).
Skoog, "Principles of Instrumental Analysis, 4$^{th}$ Edition", p. 577 (1992).
Smith, A.D., et al., "Oxford Dictionary of Biochemistry and Molecular Biology", Oxford University Press, p. 145, (1997).
Sugahara, M., et al. Chem. Pharm. Bull., vol. 45, No. 4, p. 719-721, (1997).
Snyder et al., "Functional profile of a novel modulator of serotonin, dopamine, and glutamate neurotransmission", *Psychophamacology*, 232:605-621 (2015).
Wagaw, S., et al., "A palladium-catalyzed method for the preparation of indoles via the Fischer indole synthesis," Journal of the American Chemical Society, vol. 121, No. 44, p. 10251-10263, (1999).
Wolfe, J.P., "An improved catalyst system for aromatic carbon-nitrogen bond formation: The possible involvement of bis(phosphine) palladium complexes as key intermediates," JACS, vol. 118, p. 7215-7216, (1996).

Wolfe, J.P., et al., "Intramolecular palladium-catalyzed aryl amination and aryl amidation," Tetrahedron, vol. 52, No. 21, p. 7525-7546, (1996).
Wolter, M., et al., "Synthesis of N-aryl hydrazides by copper-catalyzed coupling of hydrazides with aryl iodides," Organic Letters, vol. 3, No. 23, p. 3803-3805, (2001).
Yamada, K., et al., "A mild copper-mediated intramolecular amination of aryl halides," Synlett, No. 2, p. 231-234, (2002).
Yang, B.H., "The development of efficient protocols for the palladium-catalyzed cyclization reactions of secondary amides and carbamates," Organic Letters, vol. 1, No. 1, p. 35-37, (1999).
Zhang, Z., et al., Catalysis Communications, vol. 6, p. 784-787, (2005).
Aiken, C., "An Overview of Atypical Antipsychotics for Bipolar Depression," published on Jan. 3, 2020 at https://www.psychiatrictimes.com/view/overview-atypical-antipsychotics-bipolar-depression, 11 pages.
Angst et al. "Prevalence and Characteristics of Undiagnosed Bipolar Disorders in Patients With a Major Depressive Episode", Arch Gen Psychiatry, vol. 68(8), p. 701-709, (2011).
Beletskaya, I.P., et al., "Pd- and Cu-catalyzed selective arylation of benzotriazole," *Tetrahedron Letters*, vol. 39, pp. 5617-5620, (1998).
Darmani, et al., "Do Functional Relationships Exist Between 5-HT$_{1A}$ and 5-HT$_2$ Receptors?" *Pharmacology and Biochemistry & Behavior*, vol. 36, pp. 901-906, (1990).
Davis, et al., "ITI-007 in the Treatment of Schizophrenia: From Novel Pharmacology to Clinical Outcomes," *Expert Review of Neurotherapeutics*, vol. 16, No. 6, pp. 601-614, (2016).
Ellenbroek et al., "Animal Models for the Negative Symptoms of Schizophrenia," Behavioural Pharmacology, vol. 11, pp. 223-233, (2000).
Fletcher, P., et al., "Perceiving is Believing: A Bayesian Approach to Explaining the Positive Symptoms of Schizophrenia," Nature Reviews/Neuroscience, vol. 10, pp. 48-58, (2009).
Gramigna, J, "Lumateperone Safe, Effective for Depressive Symptoms Among Patients with Bipolar Disorders," American Society of Clinical Psychopharmacology Annual Meeting, Jun. 2, 2020, 3 pages.
Hlavinka, E., "Schizophrenia Tx Eases Depression in Bipolar Disorder: Lumateperone Offers Greater Rate of Response, Remission versus Placebo," Medpage Today, 7 pages, (2020); https://www.medpagetoday.com/meetingcoverage/psychcongress/88584.
Kahn, et al., "Residual Symptoms of Schiziphrenia. What are Realistic Treatment Goals? Lingering Symptoms Require you to Evaluate Pharmacotherapy and Offer Psychosocial Interventions," *Current Psychiatry*, vol. 16, No. 3, pp. 35-40, (2017).
Kay, et al., "The Positive and Negative Syndrome Scale (PANSS) for Schizophrenia," *Schizophrenia Bulletin*, vol. 13, No. 2, pp. 261-276, (1987).
Kessler, et al., "Lifetime Prevalence and Age-of-Onset Distributions of DSM-IV Disorders in the National Comorbidity Survey Replication," *Arch Gen Psychiatry*, vol. 62, pp. 593-602, (2005).
Khorana, et al., "Gamma-Carbolines: Binding at 5-HT5A Serotonin Receptors," *Bioorganic & Medicinal Chemistry*, vol. 11, pp. 717-722, p. 718 Table 1, (2003).
Lammers, et al., "Risperidone Long-acting Injection in Schizophrenia Spectrum Illnesses Compared to First Generation Depot Antipsychotics in an Outpatient Setting in Canada," BMC Psychiatry, vol. 13, No. 155, 9 pages, (2013); http://www.biomedcentral.com/1471-244X/13/155.
Makadia et al., "Poly Lactic-co-Glycolic Acid (PLGA) as Biodegradable Controlled Drug Delivery Carrier," Polymers (Basel), vol. 3, No. 3, pp. 1377-1397, (2011).
Marek et al. Synergistic Action of 5-HT2A Antagonists and Selective Serotonin Reuptake Inhibitors in Neuropsychiatric Disorders. Neuropsychopharmacology, 2003. vol. 28, pp. 402-412. (Year: 2003).
Medisorb Fact Sheet in Medisorb Microspheres Technology (Jan. 2009) at https://static.secure.website/wscfus/6472891/uploads/Medisorb.pdf (retrieved from the internet May 18, 2020) (Year: 2009).

(56) References Cited

OTHER PUBLICATIONS

Mueller, et al., "Detection of Depression in Acute Schizophrenia: Sensitivity and Specificity of 2 Standard Observer Rating Scales," Can J Psychiatry, vol. 51, No. 6, pp. 387-392, (2006).

Mulrooney, C.A., "Recent developments in copper-catalyzed n-arylation with aryl halides," Essa—University of Pennsylvania, 4 pages, (2004).

Nagai et al. "Synthesis of 2,3,4,4a,5,9b-hexahydro-1H-pyrido[4,3-b] indole derivatives and their central nervous system activities." *Journal of Medicinal Chemistry*, vol. 22, No. 6, p. 677-683, (1979).

Palanisamy, M. et al., "Cellulose-Based Matrix Microspheres of Prednisolone Inclusion Complex; Preparation and Characterization." American Association of Pharmaceutical Scientists PharmSciTech, vol. 12, No. 1, p. 388-400, (2011).

Perlis et al., "Clinical Features of Bipolar Depression Versus Major Depressive Disorder in Large Multicenter Trials", Am J Psychiatry, vol. 163, p. 225-231, (2006).

Rainer, M.K., "Risperidone Long-acting Injection: A Review of its Long Term Safety and Efficacy," *Neuropsychiatric Disease and Treatment*, vol. 4, No. 5, pp. 919-927, (2008).

Schennach, et al., "What Are Residual Symptoms in Schizophrenia Spectrum Disorder? Clinical Description and 1-year Persistence Within a Naturalistic Trial," *Eur. Arch. Psychiatry Clin. Neurosci.*, vol. 265, pp. 107-116, (2015); DOI: 10.1007/s00406-014-0528-2.

Snyder, et al., "Functional Profile of a Novel Modulator of Serotonin, Dopamine, and Glutamate Neurotransmission," *Psychopharmacology*, vol. 232, pp. 605-621, (2015); Published online Aug. 2014, DOI 10.1007/s00213-014-3704-1.

Tohhn, M., et al., "Efficacy of Olanzapine and Olanzapine-Fluoxetine Combination in the Treatment of Bipolar I Depression," Arch Gen Psychiatry, vol. 60, pp. 1079-1088, (2003).

Vanover, et al., "Dopamine D2 receptor occupancy of lumateperone (ITI-007): a Positron Emission Tomography Study in patients with schizophrenia," *Neuropsychopharmacology* 44:598-605, (2019).

Vanover, et al., "A Novel Approach to Address an Unmet Need in the Treatment of Schizophrenia and Depression: Lumateperone, an Innovative Modulator of Dopamine, Serotonin, and Glutamate," Abstract presented at the American Society of Clinical Psychopharmacology (ASCP) Annual Meeting; May 29-Jun. 1, 2018; Miami, FL.

Vanover, K., et al., "ITI-007: A Novel Therapy for the Treatment of Schizophrenia and Related Psychoses," International Clinical Psychopharamcology, vol. 26, e56, 1 page, (2011).

Vyas, P., et al., "An Evaluation of Lumateperone Tosylate for the Treatment of Schizophrenia," Expert Opinion on Pharmacotherapy, vol. 21, No. 2, pp. 139-145, (2020); https://doi.org/10.1080/14656566.2019.1695778.

Wennogle, et al., "Activation of NMDA and AMPA Receptors by Lumateperone (ITI-007): Implications for Antidepressant Activity," Abstract presented at the 2017 Collegium Internationale Neuro-Psychopharmacologicum (CINP) Thematic Meeting: Treatment Resistant Depression; Jul. 20-22, 2017; Prague.

* cited by examiner

SUBSTITUTED HETEROCYCLE FUSED GAMMA-CARBOLINES SYNTHESIS

CROSS REFERENCE TO RELATED APPLICATIONS

The present application is a U.S. national application filed under 35 U.S.C. § 111 which claims priority to and the benefit of U.S. Provisional Applications 62/683,411, filed on Jun. 11, 2018, and 62/780,742, filed on Dec. 17, 2018, the contents of each of which are hereby incorporated by reference in their entireties.

FIELD OF THE INVENTION

The present invention relates to methods for the preparation of substituted heterocycle fused gamma-carbolines, intermediates useful for producing them, and methods for producing such intermediates, and compositions comprising such compounds made according to these methods.

BACKGROUND OF THE INVENTION

Substituted heterocycle fused gamma-carbolines are useful as agonists or antagonists of 5-HT2 receptors, particularly 5-HT2A and 5-HT2C receptors, in treating central nervous system disorders, including obesity, anxiety, depression, psychosis, schizophrenia, sleep disorders, sexual disorders, migraine, conditions associated with cephalic pain, social phobias, and gastrointestinal disorders such as dysfunction of the gastrointestinal tract motility.

Traditional methods for the preparation of enantiomerically pure substituted heterocycle fused gamma-carbolines involve Fischer indole cyclization of aryl hydrazine (e.g., dihydroquinoxalin-1-(2H)-amine, 2H-benzo[b][1,4]oxazin-4(3H)-amine or 2H-benzo[b][1,4]thiazin-4(3H)-amine) with suitably substituted cyclic ketones (e.g., piperidin-4-one) to afford tetracyclic indole compounds (e.g., 1,3,7,8,9,10-hexahydro-1H-pyrido-[3',4':4,5]-pyrrolo[1,2,3-de]quinoxaline). This indole core is then reduced to afford the cis or trans tetracyclic dihydroindole (i.e., cis or trans tetracyclic indoline) product, which requires exhaustive purification procedures such as chiral column chromatography to afford enantiomerically pure product. This method, as a whole, is inefficient because excess reagents and reaction intermediates are required to produce racemic products, wherein such product is purified at the final step to give a 25-50% yield at best. There is thus a need for a more efficient process to make enantiomerically pure substituted heterocycle fused gamma-carbolines.

The preparation of substituted heterocycle fused gamma-carbolines in free or pharmaceutically acceptable salt forms, intermediates used in their preparation, for example enantiomerically pure 2,3,4,4a,5,9b-hexahydro-1H-pyrido[4,3-b]indole type intermediates, and methods for producing said intermediates and said substituted heterocycle fused gamma-carbolines are disclosed in U.S. Pat. Nos. 7,183,282, 8,309,722, 8,779,139, 9,315,504, and 9,751,883, the entire contents of each of which are hereby incorporated by reference.

SUMMARY OF THE INVENTION

The present invention provides improved methods for the preparation of substituted heterocycle fused gamma-carbolines in free or pharmaceutically acceptable salt forms, intermediates used in their preparation, for example enantiomerically pure 2,3,4,4a,5,9b-hexahydro-1H-pyrido[4,3-b]indole type intermediates, and methods for producing said intermediates and said substituted heterocycle fused gamma-carbolines are disclosed in the present invention. Substituted heterocycle fused gamma-carbolines and their pharmaceutically acceptable salts produced by the present invention are represented by the core structures shown in Formula 1J and 2J:

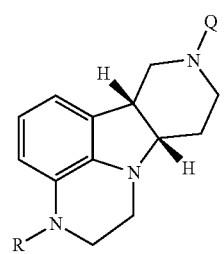

1J

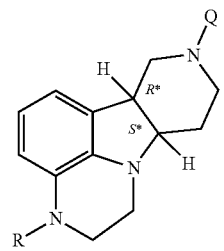

2J wherein R is selected from H and $C_{1-4}$ alkyl, and Q is selected from 4-(4-fluorophenyl)-4-oxobutyl and 3-(4-fluorophenoxy)propyl. It is understood that in the compound of Formula 1J (and like formula 1's herein throughout) the stereochemistry shown is absolute stereochemistry, which, for example, corresponds to the 4aS, 9bR configuration in the compound of Formula 1I, and the 6bR, 10aS configuration in the compound of Formula 1J. In contrasts, it is understood that in the compound of Formula 2J (and like formula 2's herein throughout) the stereochemistry shown is relative stereochemistry for the two adjacent stereocenters. Thus, for example, in the compound of Formula 2J shown above, the formula represents both compounds having the 6bR, 4aS configuration and compounds having the 6bS, 4aR configuration, or combinations thereof.

Other exemplary representations of compounds of or related to the invention are described in U.S. Pat. Nos. 6,552,017; 6,548,493; 6,713, 471; and U.S. Pat. Nos. 6,849, 619, 7,071,186, 7,081,455, and U.S. Reissued Pat. No. 39,680 and 38,679, the contents of each of which are incorporated herein by reference in their entireties. These compounds have been found to be useful as 5-HT2 receptor agonists and antagonists, as serotonin transporter antagonists, and as modulators of dopamine D1 and/or D2 receptor functioning. These compounds may be used in treating disorders of the central nervous system, including obesity, anxiety, depression, psychosis, schizophrenia, sleep disorders, sexual disorders, migraine, conditions associated with cephalic pain, social phobias, and gastrointestinal disorders such as dysfunction of the gastrointestinal tract motility.

These compounds have also been recently shown to have unique pharmacological properties related to indirect enhancement of AMPA and NMDA signalling via the D1 receptor pathway, and enhancement of mTOR signalling. Such properties are more fully described in U.S. provisional applications 62/644,355, 62/682,582, and 62/780,004, and international application PCT/US2019/022480, the contents of each of which are hereby incorporated by reference in their entireties.

In some embodiments, the present invention provides compounds of Formula 1I, as shown below, in free or salt form, which are useful, e.g., as intermediates for the production of compounds of Formula 1J:

Compounds of Formula 1I:

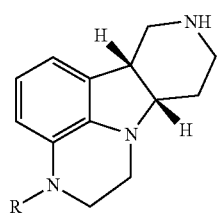

1I wherein:

R is H or $C_{1-4}$ alkyl (e.g., methyl);

in free or salt form, e.g., in acid addition salt form, optionally in solid form.

The invention further provides compounds of the following formulae:

1.1 Formula 1I, wherein R is $C_1$-$C_4$ alkyl.

1.2 Formula 1I, wherein R is methyl.

1.3 Formula 1I, 1.1 or 1.2, wherein the compound is in free base form.

1.4 Formula 1I, 1.1 or 1.2, wherein the compound is in acid addition salt form.

1.5 Formula 1.4, wherein the acid addition salt form is a hydrohalide salt form (e.g., hydrochloride, hydrobromide, hydroiodide or hydrofluoride, e.g. in a base to acid molar ratio of 1:1 to 3:1).

1.6 Formula 1.5, wherein the acid addition salt form is a hydrochloride salt.

1.7 Any of the preceding formulae, wherein said compound is in solid form, e.g., solid amorphous form or solid crystalline form.

1.8 Any of the preceding formulae wherein said compounds are at least 70%, preferably at least 80%, more preferably at least 90%, most preferably greater than 95%, and up to 100%, cis stereoisomer relative to all other stereoisomers and/or wherein said compounds have an enantiomeric excess (i.e.) of at least 70%, preferably at least 80%, more preferably at least 90%, most preferably greater than 95% or greater than 97% or greater than 99%, or greater than 99.5%, or greater than 99.9%, and up to 100% (i.e., for the 4aS, 9bR enantiomer shown above).

In some embodiments, the present invention provides compounds of Formula 2I, as shown below, in free or salt form, which are useful, e.g., as intermediates for the production of compounds of Formula 2J:

Compounds of Formula 2I:

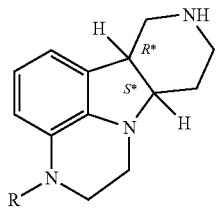

2I wherein:

R is H or $C_{1-4}$ alkyl (e.g., methyl);

in free or salt form, e.g., in acid addition salt form, optionally in solid form.

The invention further provides compounds of the following formulae:

2.1 Formula 2I, wherein R is $C_1$-$C_4$ alkyl.

2.2 Formula 2I, wherein R is methyl.

2.3 Formula 2I, 2.1 or 2.2, wherein the compound is in free base form.

2.4 Formula 2I, 2.1 or 2.2, wherein the compound is in acid addition salt form.

2.5 Formula 2.4, wherein the acid addition salt form is a hydrohalide salt form (e.g., hydrochloride, hydrobromide, hydroiodide or hydrofluoride, e.g. in a base to acid molar ratio of 1:1 to 3:1).

2.6 Formula 2.5, wherein the acid addition salt form is a hydrochloride salt.

2.7 Any of the preceding formulae, wherein said compound is in solid form, e.g., solid amorphous form or solid crystalline form.

2.8 Any of the preceding formulae wherein said compounds are at least 70%, preferably at least 80%, more preferably at least 90%, most preferably greater than 95%, and up to 100%, cis stereoisomer relative to all other stereoisomers.

The present invention further provides the following compounds, which may be formed as impurities in the processes for making the compounds of Formula 1J:

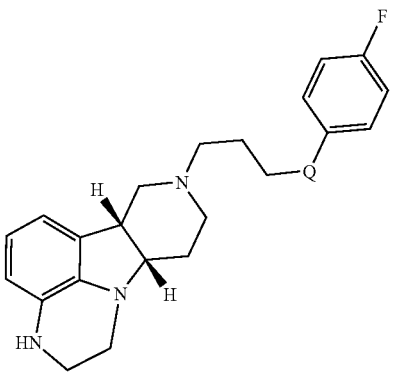

1K

;

1L
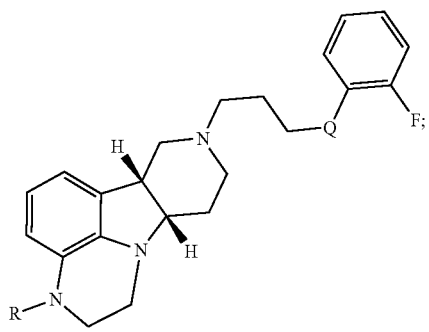
1M
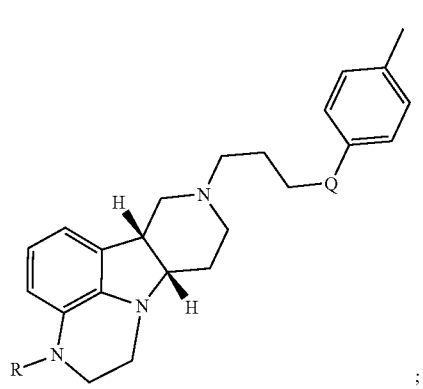
1N
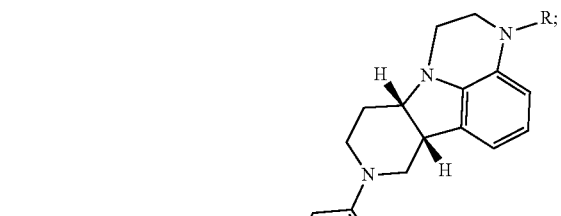
1O
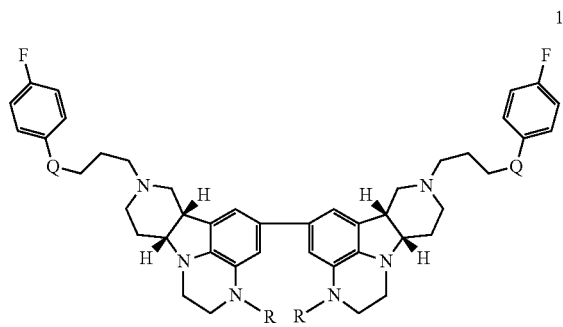
1P
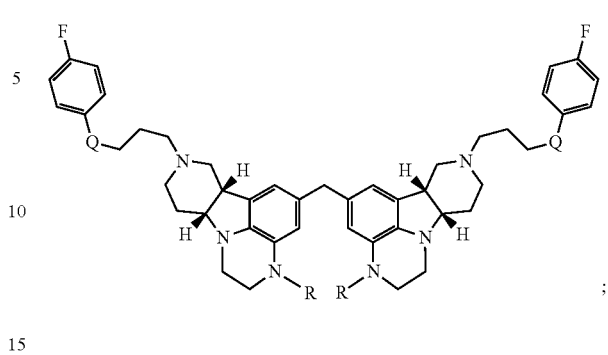
1Q
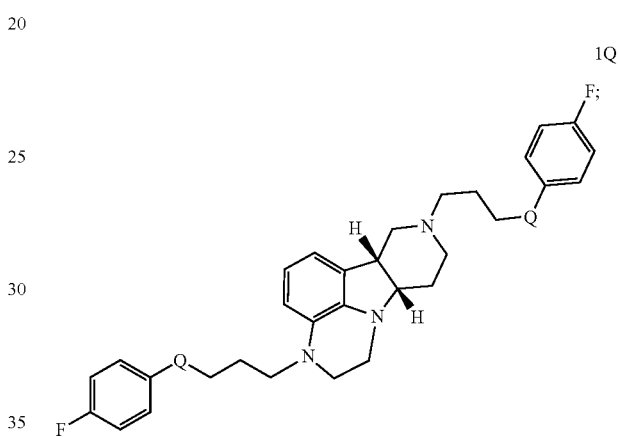
wherein, in each of said compounds 1K, 1L, 1M, 1N, 1O, 1P, 1Q, the group R is selected from H and $C_{1-4}$ alkyl (e.g., methyl), and the group Q is selected from —O— and —(C=O)—.
The present invention further provides the following compounds, which may be formed as impurities in the processes for making the compounds of Formula 2J:
2K
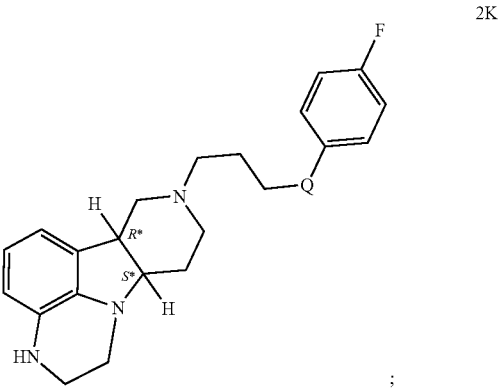

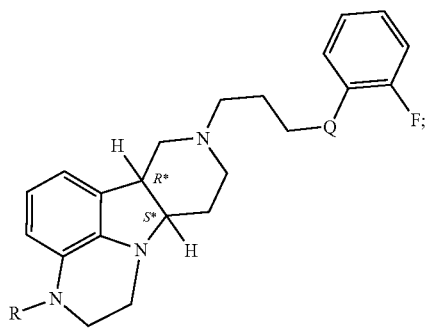
2L
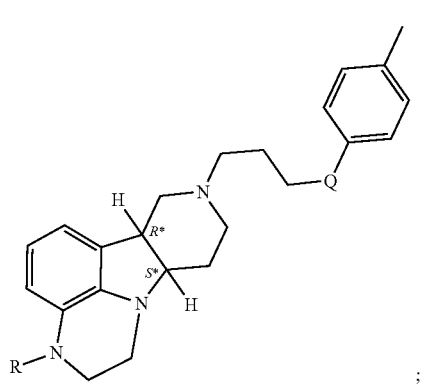
2M
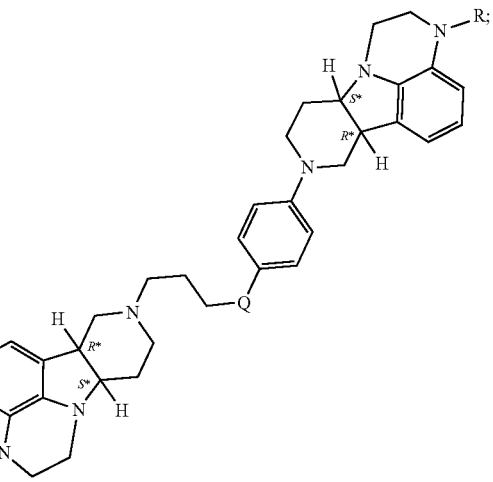
2N
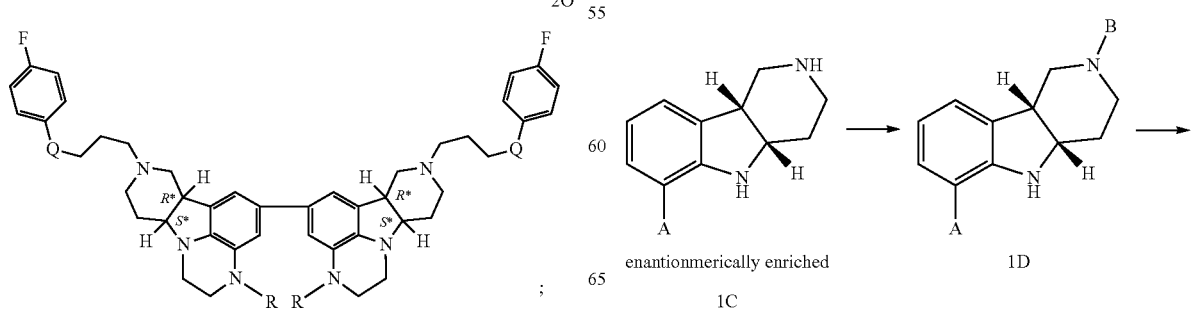
2O
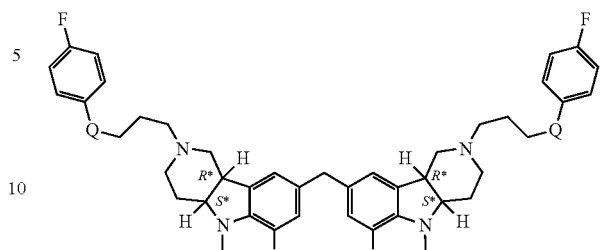
2P
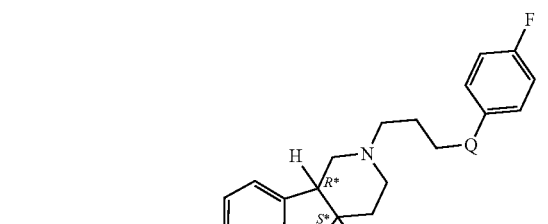
2Q
wherein, in each of said compounds 2K, 2L, 2M, 2N, 2P and 2Q, the group R is selected from H and $C_{1-4}$ alkyl (e.g., methyl), and the group Q is selected from —O— and —(C=O)—.
METHODS
In some embodiments, the present invention pertains to a method for preparing the compound of Formula 1J, as shown in the following scheme:
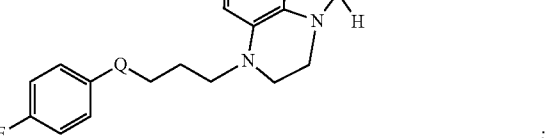
1A        racemic cis
                       1B
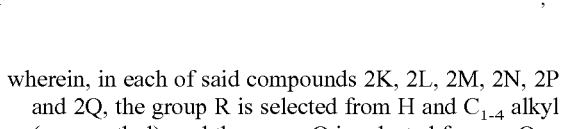
enantiomerically enriched     1D
1C -continued

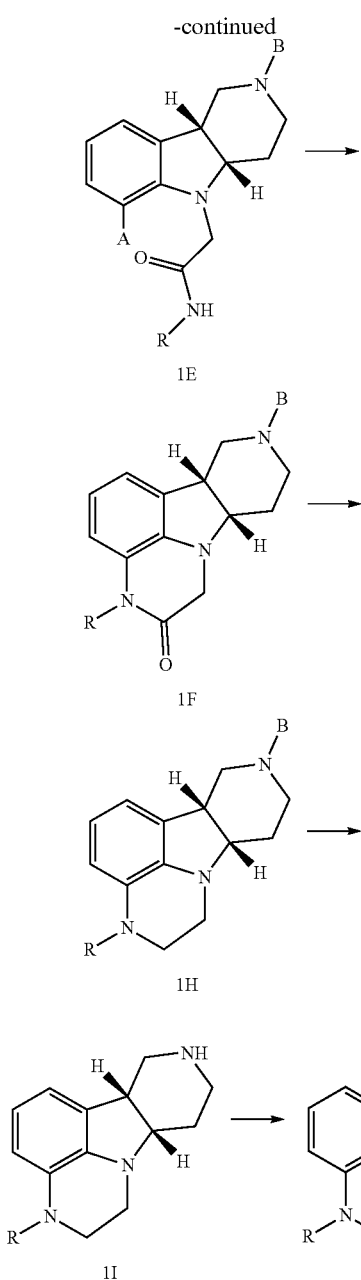

wherein for each of compounds 1A through 1J, independently:
(i) A is selected from Br, Cl and I;
(ii) R is selected from H and $C_{1-4}$ alkyl (e.g. methyl);
(iii) B is a protecting group, as defined herein; and
(iv) Q is selected from 4-(4-fluorophenyl)-4-oxobutyl and 3-(4-fluorophenoxy)propyl;

wherein each of compounds 1A, 1B, 1C, 1D, 1E, 1F, 1H, 1I and 1J are independently in free base or salt form (e.g., acid addition salt form). It is understood that the compound 1B is substantially, essentially, or completely the racemic cis isomers, i.e., containing approximately equal amounts of the two cis enantiomers to the substantial or complete exclusion of any trans isomers. It is further understood that the compound 1C is substantially, essentially, or completely a single cis enantiomer, specifically the 4aS, 9bR enantiomer (as drawn above), to the substantial or complete exclusion of the opposite cis enantiomer or any trans stereoisomer.

In some embodiments, the present invention pertains to a method for preparing the compound of formula 2J, as shown in the following scheme:

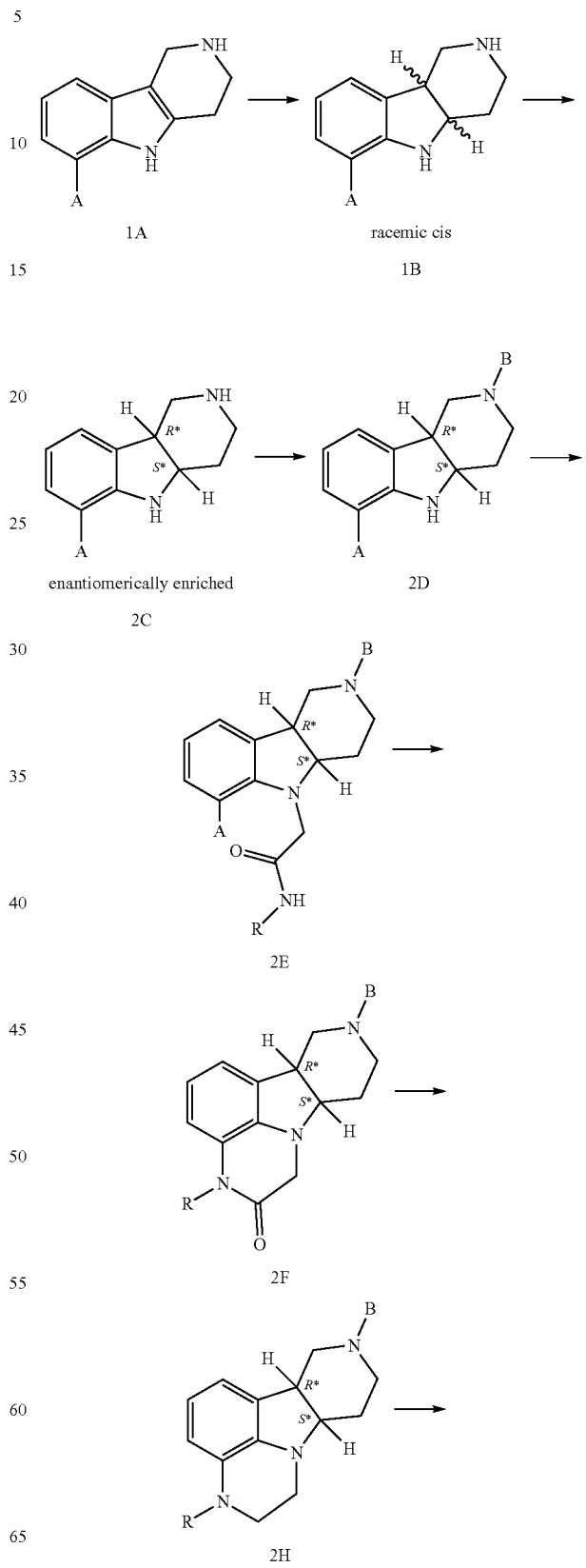

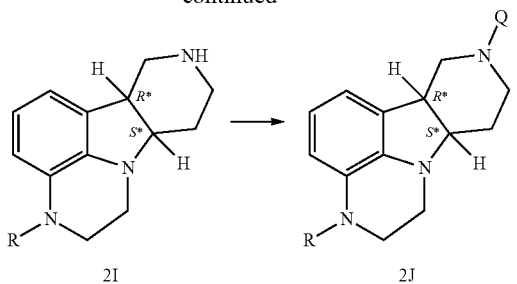

wherein for each of compounds 2A through 2J, independently:
(i) A is selected from Br, Cl and I;
(ii) R is selected from H and $C_{1-4}$ alkyl (e.g. methyl);
(iii) B is a protecting group, as defined herein; and
(iv) Q is selected from 4-(4-fluorophenyl)-4-oxobutyl and 3-(4-fluorophenoxy)propyl;

wherein each of compounds 1A, 1B, 2C, 2D, 2E, 2F, 2H, 2I and 2J are independently in free base or salt form (e.g., acid addition salt form). It is understood that the compound 1B is substantially, essentially, or completely the racemic cis isomers, i.e., containing approximately equal amounts of the two cis enantiomers to the substantial or complete exclusion of any trans isomers. It is further understood that the compound 2C is substantially, essentially, or completely a single cis enantiomer, to the substantial or complete exclusion of the opposite cis enantiomer or any trans stereoisomer.

In some embodiments, the present invention pertains to methods for preparing the compound of Formula 1J, as shown above, in free or salt form, as follows:

3.1 Formula 1J, wherein R is H.
3.2 Formula 1J, wherein R is $C_{1-4}$ alkyl.
3.3 Formula 1J, wherein R is methyl.
3.4 Formula 1J or any of 3.1-3.3, wherein Q is 4-(4-fluorophenyl)-4-oxobutyl.
3.5 Formula 1J or any of 3.1-3.3, wherein Q is 3-(4-fluorophenoxy)propyl.
3.6 Formula 1J, or any of 3.1-3.4, wherein R is methyl and Q is 4-(4-fluorophenyl)-4-oxobutyl.
3.7 Formula 1J, or any of 3.1-3.6, wherein the compound of Formula 1J is in free base form.
3.8 Formula 1J, or any of 3.1-3.6, wherein the compound of Formula 1J is in salt form.
3.9 Formula 1J, or any of 3.1-3.6, wherein the compound of Formula 1J is in acid addition salt form.
3.10 Formula 1J, or any of 3.1-3.6, wherein the compound of Formula 1J is in tosylate or hydrochloride salt form, e.g., in a 1:1 to 1:3 ratio of free base to acid.
3.11 Formula 1J, or any of 3.1-3.10, wherein the compound of Formula 1J is in solid form (e.g., solid amorphous form or solid crystal form).
3.12 Formula 1J, or any of 3.1-3.10, wherein the compound of Formula 1J is in solid crystal form, e.g., in solid crystal free base form or in solid crystal salt form.
3.13 Formula 3.12, wherein the compound of Formula 1J is in solid crystalline tosylate salt form (mono-tosylate, di-tosylate, or tri-tosylate, or any combination thereof), e.g., as described in any of U.S. Pat. Nos. 8,648,077, 9,199,995, and 9,586,960 (or its pending reissue application, Ser. No. 16/294,607), the contents of each of which are incorporated by reference herein in their entireties.
3.14 Formula 1J, or any of 3.1-3.13, wherein the compound of Formula 1J is in at least 70%, preferably at least 80%, more preferably at least 90%, most preferably greater than 95%, up to 100%, cis stereoisomer relative to all other stereoisomers.
3.15 Formula 1J, or any of 3.1-3.14, wherein the compound of Formula 1J is in substantially enantiomerically pure form, e.g., in at least 90% e.e., preferably in at least 95% e.e., or in at least 97% e.e., or in at least 99% e.e., or at least 99.5% e.e., or in at least 99.9% e.e., up to 100% e.e.

In some embodiments, the present invention pertains to methods for preparing the compound of Formula 2J, as shown above, in free or salt form, as follows:

4.1 Formula 2J, wherein R is H.
4.2 Formula 2J, wherein R is $C_{1-4}$ alkyl.
4.3 Formula 2J, wherein R is methyl.
4.4 Formula 2J or any of 4.1-4.3, wherein Q is 4-(4-fluorophenyl)-4-oxobutyl.
4.5 Formula 2J or any of 4.1-4.3, wherein Q is 3-(4-fluorophenoxy)propyl.
4.6 Formula 2J, or any of 4.1-4.4, wherein R is methyl and Q is 4-(4-fluorophenyl)-4-oxobutyl.
4.7 Formula 2J, or any of 4.1-4.6, wherein the compound of Formula 2J is in free base form.
4.8 Formula 2J, or any of 4.1-4.6, wherein the compound of Formula 2J is in salt form.
4.9 Formula 2J, or any of 4.1-4.6, wherein the compound of Formula 2J is in acid addition salt form.
4.10 Formula 2J, or any of 4.1-4.6, wherein the compound of Formula 2J is in tosylate or hydrochloride salt form, e.g., in a 1:1 to 1:3 ratio of free base to acid.
4.11 Formula 2J, or any of 4.1-4.10, wherein the compound of Formula 2J is in solid form (e.g., solid amorphous form or solid crystal form).
4.12 Formula 2J, or any of 4.1-4.10, wherein the compound of Formula 2J is in solid crystal form, e.g., in solid crystal free base form or in solid crystal salt form.
4.13 Formula 4.12, wherein the compound of Formula 2J is in solid crystalline tosylate salt form (mono-tosylate, di-tosylate, tri-tosylate, or combinations thereof), e.g., as described in any of U.S. Pat. Nos. 8,648,077, 9,199, 995, and 9,586,960 (or its pending reissue application, Ser. No. 16/294,607), the contents of each which are incorporated by reference herein in their entireties.
4.14 Formula 2J, or any of 4.1-4.13, wherein the compound of Formula 2J is in at least 70%, preferably at least 80%, more preferably at least 90%, most preferably greater than 95%, up to 100%, cis stereoisomer relative to all other stereoisomers.
4.15 Formula 2J, or any of 4.1-4.14, wherein the compound of Formula 2J is in substantially enantiomerically pure form, e.g., in at least 90% e.e., preferably in at least 95% e.e., or in at least 97% e.e, or in at least 99% e.e., or in at least 99.5%, or in at least 99.9% e.e., up to 100% e.e.

In a first aspect, the invention provides a method (Method 1I) for preparing a compound of Formula 1I, or any of 1.1-1.8, in free or salt form, comprising the steps of (a) reacting a compound of Formula 1E, in free or salt form, with (i) a transition metal catalyst selected from the group consisting of Groups 8-11 of the periodic table, (ii) optionally a base, (iii) optionally an alkali metal iodide (e.g. potassium iodide), and (iv) optionally a monodentate or bidentate ligand, to form an intermediate of Formula 1F, in free or salt form; (b) reducing the amide carbonyl of the compound of Formula 1F to yield an intermediate of Formula 1H, in free or salt form; and (c) deprotecting the piperidine nitrogen of the compound of Formula 1H to yield the compound of Formula 1I (or any of 1.1-1.8), in free or salt form.

In another embodiment of the first aspect, the invention provides a method (Method 2I) for preparing a compound of Formula 2I, or any of 2.1-2.8, in free or salt form, comprising the steps of (a) reacting a compound of Formula 2E, in free or salt form, with (i) a transition metal catalyst selected from the group consisting of Groups 8-11 of the periodic table, (ii) optionally a base, (iii) optionally an alkali metal iodide (e.g. potassium iodide), and (iv) optionally a monodentate or bidentate ligand, to form an intermediate of Formula 2F, in free or salt form; (b) reducing the amide carbonyl of the compound of Formula 2F to yield an intermediate of Formula 2H, in free or salt form; and (c) deprotecting the piperidine nitrogen of the compound of Formula 2H to yield the compound of Formula 2I (or any of 2.1-2.8), in free or salt form.

In a second aspect, the invention provides a method (Method 1J) for preparing a compound of Formula 1J, or any of 3.1-3.15, in free or salt form, comprising the steps of (a) reacting a compound of Formula 1E, in free or salt form, with (i) a transition metal catalyst selected from the group consisting of Groups 8-11 of the periodic table, (ii) optionally a base, (iii) optionally an alkali metal iodide (e.g. potassium iodide), and (iv) optionally a monodentate or bidentate ligand, to form an intermediate of Formula 1F, in free or salt form; (b) reducing the amide carbonyl of the compound of Formula 1F to yield an intermediate of Formula 1H, in free or salt form; and (c) deprotecting the piperidine nitrogen of the compound of Formula 1H to yield the compound of Formula 1I (or any of 1.1-1.8), in free or salt form; and (d) alkylating the piperidine nitrogen of the compound of Formula 1I with a suitable alkylating agent to yield the compound of Formula 1J (or any of 3.1-3.15) in free or salt form; and optionally (e) converting the compound of Formula 1J in free form to a compound of Formula 1J (or any of 3.1-3.15) in salt form, e.g., acid addition salt form (e.g., tosylate salt form).

In another embodiment of the second aspect, the invention provides a method (Method 2J) for preparing a compound of Formula 2J, or any of 4.1-4.15, in free or salt form, comprising the steps of (a) reacting a compound of Formula 2E, in free or salt form, with (i) a transition metal catalyst selected from the group consisting of Groups 8-11 of the periodic table, (ii) optionally a base, (iii) optionally an alkali metal iodide (e.g. potassium iodide), and (iv) optionally a monodentate or bidentate ligand, to form an intermediate of Formula 2F, in free or salt form; (b) reducing the amide carbonyl of the compound of Formula 2F to yield an intermediate of Formula 2H, in free or salt form; and (c) deprotecting the piperidine nitrogen of the compound of Formula 2H to yield the compound of Formula 2I (or any of 2.1-2.8), in free or salt form; and (d) alkylating the piperidine nitrogen of the compound of Formula 1I with a suitable alkylating agent to yield the compound of Formula 2J (or any of 4.1-4.15) in free or salt form; and optionally (e) converting the compound of Formula 2J in free form to a compound of Formula 2J (or any of 4.1-4.15) in salt form, e.g., acid addition salt form (e.g., tosylate salt form).

In another aspect, the present disclosure provides for the use of the Compound of Formula 1I, or any of 1.1 et seq., in a process for the manufacture of a compound of Formula 1J, or any of 3.1-3.15.

In another aspect, the present disclosure provides for the use of the Compound of Formula 2I, or any of 2.1 et seq., in a process for the manufacture of a compound of Formula 2J, or any of 4.1-4.15.

In another aspect, the present disclosure provides an active pharmaceutical composition comprising the compound of Formula 1J or 2J, or any of 3.1-3.15 or 4.1-4.15, in substantially pure form.

DETAILED DESCRIPTION OF THE INVENTION

Figure 1:
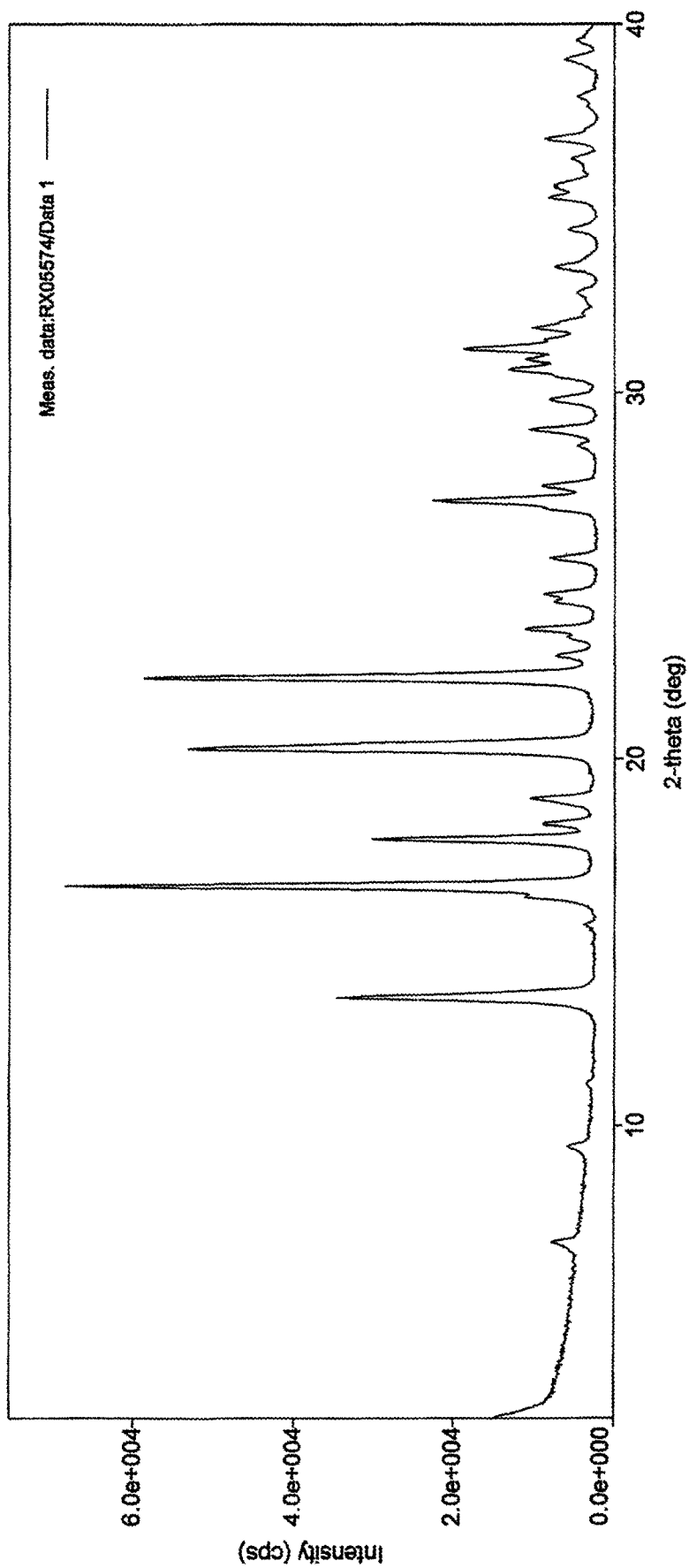
FIG. 1 shows the XRPD Pattern of 4-((6bR,10aS)-3-methyl-2,3,6b,7,8,9,10,10a-octahydro-1H-pyrido-[3',4':4,5]-pyrrolo[1,2,3-de]quinoxaline mono-hydrochloride salt as obtained according to Example 14.

In a first aspect, the invention provides a method (Method 1I) for preparing a compound of Formula 1I, or any of 1.1-1.8, in free or salt form, comprising the steps of (a) reacting a compound of Formula 1E, in free or salt form, with (i) a transition metal catalyst selected from the group consisting of Groups 8-11 of the periodic table, (ii) optionally a base, (iii) optionally an alkali metal iodide (e.g. potassium iodide), and (iv) optionally a monodentate or bidentate ligand, to form an intermediate of Formula 1F, in free or salt form; (b) reducing the amide carbonyl of the compound of Formula 1F to yield an intermediate of Formula 1H, in free or salt form; and (c) deprotecting the piperidine nitrogen of the compound of Formula 1H to yield the compound of Formula 1I (or any of 1.1-1.8), in free or salt form.

Preferably, steps (a), (b), and (c) take place without isolation or without purification of the intermediates of the Formulas 1F and 1H. In some embodiments, the steps (a), (b), and (c) take place sequentially in a single reaction vessel or a set of connected reaction vessels.

In another embodiment of the first aspect, the invention provides a method (Method 2I) for preparing a compound of Formula 2I, or any of 2.1-2.8, in free or salt form, comprising the steps of (a) reacting a compound of Formula 2E, in free or salt form, with (i) a transition metal catalyst selected from the group consisting of Groups 8-11 of the periodic table, (ii) optionally a base, (iii) optionally an alkali metal iodide (e.g. potassium iodide), and (iv) optionally a monodentate or bidentate ligand, to form an intermediate of Formula 2F, in free or salt form; (b) reducing the amide carbonyl of the compound of Formula 2F to yield an intermediate of Formula 2H, in free or salt form; and (c) deprotecting the piperidine nitrogen of the compound of Formula 2H to yield the compound of Formula 2I (or any of 2.1-2.8), in free or salt form.

Preferably, steps (a), (b), and (c) take place without isolation or without purification of the intermediates of the Formulas 2F and 2H. In some embodiments, the steps (a), (b), and (c) take place sequentially in a single reaction vessel or a set of connected reaction vessels.

The transition metal catalyst of step (a) of Method 1I or 2I may be an atom, ion, salt or complex of transition metals selected from Groups 8-11 of the periodic table (e.g., palladium, copper, nickel, platinum, ruthenium, or rhodium).

Examples of such transition metal catalyst include, but are not limited to, copper catalysts such as CuI, CuCl, CuBr, $CuBr_2$, Cu(II) acetate, $Cu_2Cl_2$, $Cu_2O$, Cu, $CuSO_4$, $Cu_2SO_4$, or palladium or nickel catalysts such as Pd/C, $PdCl_2$, $Pd(OAc)_2$, $(CH_3CN)_2PdCl_2$, $Pd[P(C_6H_5)_3]_4$, bis(dibenzylideneacetone)palladium $[Pd(dba)_2]$, tris(dibenzylideneacetone)dipalladium $[Pd_2(dba)_3]$, $Ni(acetylacetonate)_2$, $NiCl_2[P(C_6H_5)]_2$ and $Ni(1,5-cyclooctadiene)_2$ as described in U.S. Pat. Nos. 6,759,554 B2, 6,395,916 B1, and 6,307,087 B1, each of which are herein incorporated by reference in their entirety. In a preferred embodiment, the transition metal catalyst is copper catalyst. In an especially preferred embodiment, said catalyst is CuI.

The base useful for step (a) of Method 1I or 2I may be a Bronsted base or a Lewis base, including by way of example only, amine bases (e.g. triethylamine, trimethylamine, N,N'-diisopropylethylamine, 1,8-diazabicyclo[5.4.0]undec-7-ene (DBU) or 1,4-diazabicyclo[2.2.2]octane (DABCO)), hydrides (e.g. sodium, lithium or potassium hydride), alkoxides (e.g., sodium or potassium tert-butoxide), carbonates (e.g., sodium carbonate or bicarbonate, potassium or cesium carbonate) or phosphates (e.g., potassium phosphate). In a preferred embodiment, the base is a carbonate of an alkali or alkali earth metal (e.g., sodium, potassium, cesium, barium, etc.). In an especially preferred embodiment, said base is potassium carbonate.

In some embodiments, the base for step (a) may be eliminated by using a ligand for step (a) which it itself basic, such as an amine ligand (e.g. DBU, DBN or a 1,2-diamine), as described below. In such embodiments, step (a) may comprise the ligand (iv) without a base (ii).

The optional mono- or bi-dentate ligands useful in step (a) of Method 1I or 2I are those ligands known to ligate with transition metal catalysts. Examples of such ligands include, but are not limited to phenolic or amine ligands, such as optionally substituted aryl alcohol, 1,2-diamine, 1,2-aminoalcohol, 1,8-diazabicyclo[5.4.0]undec-7-ene (DBU), 1,5-diazabicyclo[4.3.0]non-5-ene (DBN), 1,4-diazabicyclo[2.2.2]octane (DABCO), imidazolium carbene, 4-(dimethylamino)pyridine, 2-(aminomethyl)pyridine, 4,7-diphenyl-1,10-phenanthroline, 4,7-dimethyl-1,10-phenanthroline, 5-methyl-1,10-phenanthroline, 5-chloro-1,10-phenanthroline, and 5-nitro-1,10-phenanthroline. For examples of phenolic or amine ligands include, but are not limited to, 2-phenylphenol, 2,6-dimethylphenol, 2-isopropylphenol, 1-naphthol, 8-hydroxyquinoline, 8-aminoquinoline, DBU, DBN, DABCO, 2-(dimethylamino)ethanol, N,N-diethylsalicylamide, 2-(dimethylamino)glycine, N,N,N',N'-tetramethyl-1,2-diaminoethane, 4,7-diphenyl-1,10-phenanthroline, 4,7-dimethyl-1,10-phenanthroline, 5-methyl-1,10-phenanthroline, 5-chloro-1,10-phenanthroline, 5-nitro-1,10-phenanthroline, 4-(dimethylamino)pyridine, 2-(aminomethyl)pyridine, (methylimino)diacetic acid, cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, cis-N-tolyl-1,2-diaminocyclohexane, trans-N-tolyl-1,2-diaminocyclohexane, a mixture of cis- and trans-N-tolyl-1,2-diaminocyclohexane, ethanolamine, 1,2-diaminoethane, N,N'-dimethyl-1,2-diaminoethane, N,N-dimethyl-2-hydroxybenzamide, N,N-diethyl-2-hydroxybenzamide, fluoro-N,N-diethyl-2-hydroxybenzamide, chloro-N,N'-diethyl-2-hydroxybenzamide, (2-hydroxyphenyl)(pyrrolidin-1-yl) methanone, biphenyl-2-ol, 2-pyridylphenol, 1,2-benzenediamine, ammonia, N,N-dimethylformamide, dimethylsulfoxide and 1-methyl-2-pyrrolidinone, as described in U.S. Pat. Nos. 6,759,554B2; 6,395,916B1; 6,307,087B1, Klapars, A. et al., *J. Am. Chem. Soc.* (2002) 124, 7421-7428; Kang, S., et al., Synlett, 3, 427-430 (2002); Sugahara, M. and Ukita, T., *Chem. Pharm. Bull.* (1997) 45, 719-721, each of which is hereby incorporated by reference in their entireties. In an especially preferred embodiment, said ligand is DBU, DBN, N,N'-dimethyl-1,2-diaminoethane, trans-N,N'-dimethyl-1,2-diaminocyclohexane, or N-butylethylenediamine. Without being bound to any theory, it is believed that the ligands facilitate the reaction by stabilizing and solubilizing the metal catalyst.

Other mono- or bi-dentate ligands useful in step (a) of Method 1I or 2I include phosphine ligands (including phosphine oxide ligands), such as those commonly referred to as Buchwald ligands. Such ligands include, but are not limited to: triphenyl phosphine, trimethyl phosphine, triethyl phosphine, tri-n-butyl phosphine, tri-t-butyl phosphine, tri-n-octyl phosphine, tricyclohexyl phosphine, tri-o-tolyl phosphine, dimethyl phenyl phosphine, diphenyl methyl phosphine, tri-2-furyl phosphine, APhos (di-t-butyl-4'(N,N-dimethylphenyl)-phosphine), diphenyl-2-pyridylphosphine, tris(hydroxymethyl)phosphine, dicyclohexyl phosphine, diphenyl phosphine, diisopropyl phosphine, dichloro phenyl phosphine ($PhPCl_2$), chloro diphenyl phosphine ($Ph_2PCl$), chloro di-ethyl phosphine, di-t-butyl phosphine, chloro di-t-butyl phosphine, chloro di-cyclohexyl phosphine, trimethoxy phosphine, triethoxy phosphine, triphenoxy phosphine, 2-chloro-4,4,5,5-tetramethyl-1,3,2-dioxaphospholane, di-t-butyl-N,N-diisopropyl phosphoramidite, bis(diisopropylamino)chloro phosphine, HMPT (hexamethyl phosphine triamine), tris(diethylamino)phosphine, tris(trimethylsilyl)phosphine, TriPhos, BippyPhos, QPhos, PTA, Bis-(p-sulfonatophenyl)phenyl phosphine dihydrate dipotassium salt, 6-DPPon, Xantphos, Xanphos, DPEPhos, BINAP (racemic, (+) or (−)), SEGPHOS (racemic, (S) or (R)), DPPBenz, DPPF, DMPE, DPPM, DPPE, DPPP, DPPB, 1,2-bis(dichlorophosphino)ethane, DCPE, D-t-BPF, DNPF, Cyclohexyl JohnPhos, DavePhos, XPhos, SPhos, MePhos, RuPhos, BrettPhos, s-SPhos, PhDavePhos, tBuXPhos, JohnPhos, Tetramethyl di-t-Bu-XPhos, t-BuMePhos, t-BuBrettPhos, t-BuDavePhos, JackiePhos, cataCXium ligands (e.g., di-adamantylalkylphosphine and analogs thereof), MeDalPhos, Mor-DalPhos, di(1-adamantyl)-1-piperidnyl-phenyl phosphine, and any P-oxide of the foregoing, for example, triphenyl phosphine oxide, TOPO (tri-n-octyl-phosphine oxide), diphenyl phosphine oxide, chloro diphenyl phosphine oxide, dichloro phenyl phosphine oxide, etc., and any other analogs thereof. Such ligands are known to those skilled in the art and exemplified, for example, in the Sigma Aldrich Phosphine Ligand Application Guide (Sigma Aldrich, 2013). In particular embodiments, the ligands may be selected from the bi-dentate bi-aryl phosphine ligand family, e.g., XantPhos, Xanphos, BINAP, SEGPHOS, Cyclohexyl JohnPhos, DavePhos, XPhos, SPhos, MePhos, RuPhos, BrettPhos, s-SPhos, PhDavePhos, tBuXPhos, JohnPhos, Tetramethyl di-t-Bu-XPhos, t-BuMePhos, t-BuBrettPhos, t-BuDavePhos, JackiePhos, for example, XantPhos, XanPhos, BINAP, XPhos, SPhos, RuPhos, or BrettPhos.

Step (a) of Method 1I or 2I may be carried out in any suitable organic solvent, for example, dioxane, dimethoxyethane, toluene, xylene, chlorobenzene, or the like.

The reduction of step (b) of Method 1I or 2I may be accomplished through the use of any suitable reducing agent, for example, a reducing agent selected from: metal hydrides (e.g., diisobutyl aluminum hydride (DIBAL), sodium bis(2-methoxyethoxy)aluminum hydride (Red-Al)

or sodium cyanoborohydride); boranes (e.g., borane-THF, borane-dimethylsulfide, diborane, borane-ammonia); or organoboranes (e.g. bis(benzyloxy)borane, BBN, trialkylboranes). Alternatively, such conversion may also be accomplished through catalytic hydrogenation by using hydrogen in the presence of a catalyst, e.g., a noble transition metal catalyst such as a nickel, platinum, palladium, rhodium, or ruthenium catalyst (e.g. palladium on carbon, platinum oxide, Raney nickel, etc.); Wolff-Kishner reduction by heating the ketone with hydrazine hydrate in the presence of a base such as sodium or potassium hydroxide (See Todd, *Org. React.* 4, 378-422 (1948)); or Clemmensen reduction by heating the ketone with zinc amalgam and an aqueous mineral acid such as hydrochloric acid (See Vedejs, *Org. React.* 22, 401-422 (1975)). Other reagents that may also accomplish such reduction include triisopropyl phosphate, copper in the presence of sulfuric acid, and tin in the presence of hydrochloric acid.

In preferred embodiments, said reduction is carried out using a borane or organoborane reducing agent, such as borane-THF complex, borane-dimethylsulfide complex, diborane, borane-ammonia complex, trialkyl boranes (such as trimethylborane, triethylborane, or tri-isopropylborane), bis(benzyloxy)borane or 9-borabicyclo[3.3.1]nonane (9-BBN). Suitable solvents include ethereal solvents such as tetrahydrofuran (THF), 1,4-dioxane, diethyl ether, diisopropyl ether, and tert-butyl methyl ether.

The conditions for the deprotection step (c) of Method 1I or 2I necessarily varies with the choice of the protecting group B and may involve, for example, acid or base catalysis or catalytic hydrogenation. Thus, for example, wherein the protecting agent is an acyl group such as an alkanoyl or alkoxycarbonyl group (e.g., ethoxycarbonyl) or an aroyl group, deprotection may be accomplished, for example, by hydrolysis with a base such as an alkali metal hydroxide, for example lithium, potassium or sodium hydroxide. Alternatively, an acyl protecting agent such as a t-butoxycarbonyl group may be removed, for example, by treatment with a suitable acid, such as hydrochloric, sulfuric or phosphoric acid or trifluoroacetic acid. An arylmethoxycarbonyl protecting agent such as a benzyloxycarbonyl group may be removed, for example, by hydrogenation over a catalyst such as platinum or palladium-on-carbon, or by treatment with a Lewis acid such as boron tris(trifluoroacetate). For further examples of reagents useful for said deprotection step, see "Protective Groups in Organic Synthesis" by Theodora Green (publisher: John Wiley & Sons).

In a preferred embodiment, the protecting group B is a carbamate protecting group, for example, methoxycarbonyl, ethoxycarbonyl, propoxycarbonyl, isopropoxycarbonyl, or t-butoxycarbonyl. In said embodiment, step (c) of Method 1I or 2I may preferably be carried out using an acidic aqueous solution, such as aqueous hydrochloric acid, or using a non-aqueous acidic medium, such as hydrogen chloride in an organic solvent (e.g., methanol, THF, dioxane, diethyl ether, or a mixture thereof) or using a strong organic acid (e.g., neat trifluoroacetic acid (TFA), or TFA in a suitable organic solvent, e.g. dioxane).

In an alternative embodiment, said carbamate protecting group (e.g., ethoxycarbonyl) may be removed under basic conditions, e.g., step (c) of Method 1I or 2I may be carried our using an alkali metal hydroxide (e.g., sodium or potassium hydroxide) in an alcoholic solvent (e.g., methanol, ethanol, isopropanol, n-butanol, t-butanol, or a mixture therefore, optionally, further comprising water).

In another preferred embodiment, the protecting group B is a benzyloxycarbonyl protecting group, and step (c) of Method 1I or 2I is carried out using hydrogen over a palladium or platinum catalyst (e.g., Pd/C or platinum oxide), for example, in an alcoholic solvent (e.g., methanol, ethanol, propanol, butanol, etc.)

In some embodiments, step (c) of Method 1I or 2I is carried out under acidic conditions and the compound of Formula 1I or 2I is obtained in the form of an acid addition salt. For example, the reaction can be carried out using hydrochloric acid, resulting in the compound of Formula 1I or 2I as a hydrochloride salt. In other embodiments, step (c) of Method 1I or 2I is carried out under acidic conditions and the reaction mixture is subjected to neutralization or basification with a suitable base in order to obtain the compound of Formula 1I or 2I in free base form. Suitable bases for carrying out said neutralization or basification include inorganic bases such as hydroxides, oxides, carbonates and bicarbonates (e.g., alkali metal or alkaline earth metal bases, including NaOH, KOH, LiOH, $Ca(OH)_2$, CaO, MgO, $Na_2CO_3$, $K_2CO_3$, $Li_2CO_3$, $NaHCO_3$, $KHCO_3$, $LiHCO_3$, $CaCO_3$, $MgCO_3$, and the like).

In some embodiments, Method 1I or 2I provides the compounds of Formula 1I or 2I, respectively, as a crystalline free base or as a crystalline acid-addition salt, e.g., as a hydrochloride salt. The inventors have unexpectedly found that use of the Method 1I or 2I, or one or more of Methods 5.1-5.52, results in the production of compounds of Formula 1I or 2I with much lower levels of contamination by transition metal impurities (e.g., copper) compared to prior art methods of making these compounds. For example, use of the present methods can result in the production of compounds of Formula 1I or 2I containing less than about 50 ppm of copper, or less than about 10 ppm of copper, or less than about 5 ppm of copper.

In specific embodiments of the first aspect, the present disclosure provides:

5.1 Method 1I or 2I, wherein the compound of Formula 1I or 2I is, respectively, a compound according to any of Formula 1.1-1.8 or 2.1-2.8.

5.2 Method 1I or 2I, wherein the substituent A of the compound of Formula 1E or 2E is selected from Br, Cl and I.

5.3 Method 5.2, wherein A is Br.

5.4 Method 1I or 2I, or any of 5.1 et seq., wherein the substituent R of the compounds of Formulas 1E, 1F, 1H and 1I, or 2E, 2F, 2H and 2I, is $C_{1-4}$ alkyl (e.g., methyl).

5.5 Method 1I or 2I, or any of 5.1 et seq., wherein the substituent R of the compounds of Formulas 1E and 1F, or 2E and 2F, is H.

5.6 Method 1I or 2I, or any of 5.1 et seq., wherein the protecting group B of the compounds of Formulas 1E, 1F and 1H, or 2E, 2F and 2H, is a group of the formula P-Z, wherein P is selected from $CH_2$, C(O), C(O)O and $S(O)_2$, and wherein Z is an optionally substituted alkyl, aryl, alkylaryl or —OR' wherein R' is alkyl, aryl, arylalkyl or heteroarylalkyl.

5.7 Method 5.6, wherein the protecting group B is an acyl group (e.g., an alkanoyl or alkoxycarbonyl group), for example, t-butoxycarbonyl, phenoxycarbonyl, ethoxycarbonyl, or methoxycarbonyl, or an optionally substituted benzyloxycarbonyl (e.g., benzyloxycarbonyl).

5.8 Method 5.7, wherein the protecting group B is ethoxycarbonyl.

5.9 Method 5.6, wherein the protecting group is an optionally substituted benzyl group, e.g., benzyl, 4-methoxybenzyl, or 2,4-dimethoxybenzyl.

5.10 Method 1I or 2I, or any of 5.1 et seq., wherein the transition metal catalyst of step (a) is a copper catalyst.

5.11 Method 5.10, wherein the transition metal catalyst of step (a) is selected from CuI, CuBr, CuCl, Cu(OAc)$_2$, Cu$_2$Cl$_2$, CuBr$_2$, CuSO$_4$, Cu$_2$SO$_4$, and Cu$_2$O.

5.12 Method 5.11, wherein the transition metal catalyst of step (a) is selected from CuI, CuBr and CuCl.

5.13 Method 5.12 wherein the transition metal catalyst is CuI.

5.14 Method 1I or 2I, or any of 5.1 et seq., wherein the transition metal catalyst of step (a) is present in an amount of 0.01 to 0.50 equivalents, e.g., from 0.05 to 0.40 equivalents, or from 0.10 to 0.30 equivalents, or from 0.15 to 0.25 equivalents, or about 0.20 equivalents.

5.15 Method 1I or 2I, or any of 5.1 et seq., wherein the base of step (a) is a Bronsted base, for example, selected from amines, alkoxides, carbonates and phosphates, and mixtures thereof.

5.16 Method 5.15, wherein the base of step (a) is a carbonate base, for example, an alkali or alkaline earth metal carbonate or bicarbonate, or mixtures thereof.

5.17 Method 5.16, wherein the base of step (a) is selected from sodium carbonate, potassium carbonate, sodium bicarbonate, or potassium bicarbonate, or a mixture thereof.

5.18 Method 5.17, wherein the base of step (a) comprises potassium carbonate, optionally in an amount of 1.5 to 3 equivalents, e.g., 2 to 2.5 equivalents, or about 2.2 equivalents.

5.19 Method 1I or 2I, or any of 5.1 et seq., wherein step (a) does not comprise the base (ii), e.g., does not comprise an alkoxide, carbonate, phosphate or other inorganic base.

5.20 Method 1I or 2I, or any of 5.1 et seq., wherein step (a) comprises an alkali metal iodide, e.g., selected from sodium iodide, potassium iodide, and lithium iodide.

5.21 Method 5.20, wherein step (a) comprises potassium iodide.

5.22 Method 1I or 2I, or any of 5.1 et seq., wherein step (a) comprises a mono-dentate or bi-dentate ligand, for example, a ligand selected from phenolic or amine ligands, or phosphine ligands.

5.23 Method 5.22, wherein the ligand is selected from an optionally substituted 1,2-diamine, an optionally substituted 1,2-aminoalcohol, DBU, DBN, or DABCO.

5.24 Method 5.23, wherein the ligand is DBU.

5.25 Method 1I or 2I, or any of 5.1 et seq., wherein the ligand of step (a) is present in an amount of 0.01 to 0.50 equivalents, e.g., from 0.05 to 0.45 equivalents, or from 0.10 to 0.40 equivalents, or from 0.20 to 0.30 equivalents, or about 0.25 equivalents.

5.26 Method 1I or 2I, or any of 5.1 et seq., wherein the solvent for step (a) is toluene or dioxane.

5.27 Method 1I or 2I, or any of 5.1 et seq., wherein the reduction of step (b) is accomplished using a reducing agent selected from metal hydrides, boranes and organoboranes.

5.28 Method 5.27, wherein the reducing agent is selected from boranes, for example, borane (BH$_3$) and borane complexes (e.g., BH$_3$-THF, BH$_3$—Me$_2$S and BH$_3$—NH$_3$).

5.29 Method 5.28, wherein the reducing agent is borane-THF complex.

5.30 Method 1I or 2I, or any of 5.1 et seq., wherein the solvent for step (b) is a mixture of toluene and THF.

5.31 Method 1I or 2I, or any of 5.1 et seq., wherein the reducing agent of step (b) is present in an amount of 1.5 to 5 equivalents, e.g., 2 to 4 equivalents, or 2.5 to 3.5 equivalents, or about 3 equivalents.

5.32 Method 1I or 2I, or any of 5.1 et seq., wherein the deprotection step (c) is an acid- or base-mediated cleavage reaction, a hydrolysis reaction (e.g., acid- or base-catalysed) or hydrogenation reaction.

5.33 Method 5.32, wherein the deprotection step (c) is an aqueous hydrolysis, e.g., an acidic or basic hydrolysis.

5.34 Method 5.33, wherein the aqueous hydrolysis comprises an acidic catalyst, e.g., selected from hydrochloric acid, hydrobromic acid, sulfuric acid, phosphoric acid, and nitric acid.

5.35 Method 5.33, wherein the aqueous hydrolysis comprises aqueous hydrochloric acid.

5.36 Method 5.33, wherein the aqueous hydrolysis comprises a basic catalyst, e.g., selected from an alkali metal or alkaline earth metal hydroxide, such as sodium hydroxide or potassium hydroxide.

5.37 Method 5.32, wherein the deprotection step (c) is an acid-mediated cleavage, e.g., comprising a strong acid (e.g., hydrochloric acid, trifluoroacetic acid or methanesulfonic acid) optionally neat or with an organic solvent.

5.38 Method 5.32, wherein the deprotection step (c) is a base-mediated cleavage, e.g., comprising an organic base (e.g. piperidine) in an organic solvent.

5.39 Method 5.32, wherein the deprotection step (c) is a hydrogenation reaction, e.g., a catalytic hydrogen comprising a transition metal catalyst (e.g., platinum or palladium) and hydrogen.

5.40 Method 1I or 2I, or any of 5.1 et seq., wherein the compound of Formula 1I or 2I (e.g., the compound of any of 1.1-1.8 or 2.1-2.8) is obtained as a solid, e.g., as an amorphous or crystalline solid.

5.41 Method 1I or 2I, or any of 5.1 et seq., wherein the compound of Formula 1I or 2I (e.g., the compound of any of 1.1-1.8 or 2.1-2.8) is obtained in substantially pure form, e.g., greater than 90 wt % pure, or, e.g., greater than 95 wt % pure, up to 100 wt % pure.

5.42 Method 1I or 2I, or any of 5.1 et seq., wherein the compound of Formula 1I or 2I (e.g., the compound of any of 1.1-1.8 or 2.1-2.8) is obtained in free form (i.e., free base form), optionally as a crystalline solid.

5.43 Method 1I or 2I, or any of 5.1 et seq., wherein the compound of Formula 1I or 2I (e.g., the compound of any of 1.1-1.8 or 2.1-2.8) is obtained in salt form, e.g., acid addition salt form.

5.44 Method 5.43, wherein the compound of Formula 1I or 2I (e.g., the compound of any of 1.1-1.8 or 2.1-2.8) is obtained as an addition salt selected from a hydrochloride, hydrobromide, hydroiodide, formate, acetate, trifluoroacetate or methanesulfonate, e.g. in a base to acid molar ratio of 1:1 to 3:1.

5.45 Method 5.44, wherein the compound of Formula 1I or 2I (e.g., the compound of any of 1.1-1.8 or 2.1-2.8) is obtained as a hydrochloride salt, e.g., as a solid hydrochloride salt or crystalline solid hydrochloride salt (e.g., as a mono-hydrochloride salt, di-hydrochloride salt, and/or tri-hydrochloride salt).

5.46 Method 1I or 2I, or any of 5.1 et seq., wherein the method takes place without isolation or without purification of the intermediates of the Formulas 1F and 1H, or 2F and 2H.

5.47 Method 1I or 2I, or any of 5.1 et seq., wherein steps (a), (b) and (c) take place sequentially in a single reaction vessel or set of connected reaction vessels.

5.48 Method 1I or 2I, or any of 5.1 et seq., wherein the compound of Formula 1I or 2I (e.g., the compound of any of 1.1-1.8 or 2.1-2.8) is obtained in a form having less than about 50 ppm of copper, or less than about 10 ppm of copper, or less than about 5 ppm of copper.

5.49 Method 1I or 2I, or any of 5.1 et seq., wherein the method further comprises a step (d) of alkylating the piperidine nitrogen of the compound of Formula 1I or 2I with a suitable alkylating agent, as herein described, to yield a compound of Formula 1J or 2J, in free or salt form.

5.50 Method 5.49, wherein the compound of Formula 1J or 2J is obtained in free base form from step (d), and wherein the method further comprises a step (e) of converting said compound of Formula 1J or 2J in free base form into a compound of Formula 1J or 2J in salt form, e.g., acid addition salt form (e.g., tosylate salt form).

5.51 Method 5.49 or 5.50 wherein the method provides a compound of Formula 1J or 2J as described by Formulas 3.1-3.15 or 4.1-4.15, respectively.

5.52 Method 1I or 2I, or any of 5.1 to 5.51, further comprising any or all of the following steps as described in any embodiments thereof herein throughout:
 a. Preparing the compound of Formula 1A by reacting 2-bromophenylhydrazine, in free or salt form, with 4-piperidinone, in free or salt form, optionally in hydrate form, optionally in acetic acid solvent;
 b. Preparing the compound of Formula 1C or 2C, in free or salt form, by (a) reducing the compound of Formula 1A to a compound of Formula 1B, optionally wherein the reduction comprises reaction of the compound of Formula 1A with triethylsilane and methanesulfonic acid, and (b) separating the stereoisomers of Formula 1B by chiral salt resolution or chiral chromatography to yield the compound of Formula 1C or 2C, optionally wherein the chiral salt resolution is performed in a single resolution step using S-mandelic acid;
 c. Preparing the compound of Formula 1D or 2D, in free or salt form, by protecting the piperidine amine of the compound of Formula 1C or 2C with a protecting agent in the presence of a base;
 d. Preparing the compound of Formula 1E or 2E, in free or salt form, by N-alkylating a compound of Formula 1D or 2D with (a) a nucleophilic alkyl halide, and (b) a base.

In a second aspect, the invention provides a method (Method 1J) for preparing a compound of Formula 1J, or any of 3.1-3.15, in free or salt form, comprising the steps of (a) reacting a compound of Formula 1E, in free or salt form, with (i) a transition metal catalyst selected from the group consisting of Groups 8-11 of the periodic table, (ii) optionally a base, (iii) optionally an alkali metal iodide (e.g. potassium iodide), and (iv) optionally a monodentate or bidentate ligand, to form an intermediate of Formula 1F, in free or salt form; (b) reducing the amide carbonyl of the compound of Formula 1F to yield an intermediate of Formula 1H, in free or salt form; (c) deprotecting the piperidine nitrogen of the compound of Formula 1H to yield the compound of Formula 1I (or any of 1.1-1.8), in free or salt form; and (d) alkylating the piperidine nitrogen of the compound of Formula 1I with a suitable alkylating agent to yield the compound of Formula 1J (or any of 3.1-3.15) in free or salt form; and optionally (e) converting the compound of Formula 1J in free form to a compound of Formula 1J (or any of 3.1-3.15) in salt form, e.g., pharmaceutically acceptable salt form, such as acid addition salt form (e.g., tosylate salt form).

In another embodiment of the second aspect, the invention provides a method (Method 2J) for preparing a compound of Formula 2J, or any of 4.1-4.15, in free or salt form, comprising the steps of (a) reacting a compound of Formula 2E, in free or salt form, with (i) a transition metal catalyst selected from the group consisting of Groups 8-11 of the periodic table, (ii) optionally a base, (iii) optionally an alkali metal iodide (e.g. potassium iodide), and (iv) optionally a monodentate or bidentate ligand, to form an intermediate of Formula 2F, in free or salt form; (b) reducing the amide carbonyl of the compound of Formula 2F to yield an intermediate of Formula 2H, in free or salt form; (c) deprotecting the piperidine nitrogen of the compound of Formula 2H to yield the compound of Formula 2I (or any of 2.1-2.8), in free or salt form; and (d) alkylating the piperidine nitrogen of the compound of Formula 1I with a suitable alkylating agent to yield the compound of Formula 2J (or any of 4.1-4.15) in free or salt form; and optionally (e) converting the compound of Formula 2J in free form to a compound of Formula 2J (or any of 4.1-4.15) in salt form, e.g., pharmaceutically acceptable salt form, such as acid addition salt form (e.g., tosylate salt form).

In all respects, steps (a), (b), and (c) of Method 1J and 2J may be carried out according to the description above for Method 1I and 2I, respectively, including any of Methods 5.1-5.52.

Alkylating agents suitable for step (d) of Method 1J or 2J (or Methods 1I or 2I which further comprise step (d)) include compounds of the general formula Q-X, wherein Q is selected from 4-(4-fluorophenyl)-4-oxobutyl and 3-(4-fluorophenoxy)propyl, and wherein X is any suitable leaving group. Leaving groups are entities known in the art to be amenable to nucleophilic substitution reactions. In some embodiments, X is selected from chloro, bromo, iodo, $C_{1-4}$ alkylsulfonyloxy (e.g. methanesulfonyloxy) and optionally substituted arylsulfonyloxy (e.g., benzenesulfonyloxy, 4-nitrobenzenesulfonyloxy, 4-halosulfonyloxy, and the like).

In some embodiments, step (d) of Method 1J or 2J, may further comprise a suitable base. Suitable bases include, but are not limited to, organic bases such as amine bases (e.g., ammonia, triethylamine, N,N'-diisopropylethylamine or 4-(dimethylamino)pyridine (DMAP), 1,5-diazabicycl[4.3.0]-non-5-ene (DBN), 1,5-diazabicyclo[5.4.0]undec-5-ene (DBU)); or inorganic bases such as hydrides (e.g. sodium, lithium or potassium hydride), alkoxides (e.g. sodium, potassium or lithium t-butoxide), aryloxides (e.g., lithium, sodium or potassium phenoxide), or carbonates, bicarbonates, phosphates or hydroxides of alkali or alkaline earth metals (e.g. sodium, magnesium, calcium, potassium, cesium or barium carbonate, bicarbonate, hydroxide or phosphate). Optionally, step (d) may further comprise an inorganic iodide salt, such as potassium iodide or sodium iodide, preferably potassium iodide. Suitable solvents include polar protic and/or polar aprotic solvents, such as, acetonitrile, dioxane, dimethylformamide, dimethylacetamide, dimethylsulfoxide, methanol, ethanol, isopropanol, and mixtures thereof. In a preferred embodiment, step (d) comprises reaction of the compound of Formula 1I or 2I with the alkylating agent 4-chloro-4'-fluoro-butyrophenone, and a base selected from triethylamine, diisopropylethylamine, potassium carbonate and sodium carbonate. Where a base is used, the amount of base can be any amount from a catalytic amount (e.g., 0.01 equivalents) to an excess amount (e.g., 10 or more equivalents). In some embodiments, the reaction is performed with from 1.0 to 5.0 equivalents of base, e.g., 1.0 to 3.0 or 1.0 to 2.0 equivalents of base.

The compound of Formula 1J or 2J, which results from step (d) of Method 1J or 2J, may be obtained as a free base or as a salt. Suitable salt forms include acid addition salts, such as phosphates, sulfates, hydrohalides (e.g., hydrochloride), and carboxylates (e.g., acetate or formate). Either the free base form or a salt form of the compound of Formula 1J or 2J may be obtained, e.g., isolated or purified, by any suitable method, such as by crystallization. In some embodiments, the reaction of step (d) is performed in the presence of an excess of base, and this may permit the isolation of the free base of the compound of Formula 1J or 2J from the reaction mixture (e.g., by aqueous/organic extraction, and/or by chromatography, and/or by crystallization from a suitable solvent, and/or by evaporation of the reaction solvent). In some embodiments, the reaction of step (d) is performed in the absence of base or in the presence of less than one equivalent of base (e.g., 0.5 equivalent or less, or a catalytic amount). Particularly when performed in the absence of base, step (d) may yield an acid addition salt of the compound of Formula 1J or 2J, wherein the acid component of the salt is derived from the alkylating agent. For example, if the compound of Formula 1I or 2I is treated with an alkylating agent Q-X, as defined above, and in the absence of an added base, the resulting compound of Formula 1J or 2J may be obtained as the acid addition salt corresponding to the group X (e.g., if X is chloro, then the compound of Formula 1J or 2J may be obtained in the form of a hydrochloride acid addition salt). In some embodiments, an equimolar or only moderate excess of base is used during the reaction of step (d), but prior to or during purification, an excess of acid (e.g., hydrochloric acid) is added, resulting in obtainment of the compound of Formula 1J or 2J as an acid addition salt (e.g. hydrochloride).

In some embodiments, step (d) of Method 1J or 2J yields the compound of Formula 1J or 2J in free form (i.e., free base form), and this form is isolated and/or purified, and then, optionally, step (e) is performed to convert the free base form of said compound of Formula 1J or 2J into a salt form of said compound of Formula 1J or 2J, for example, a pharmaceutically acceptable salt form (e.g., an acid addition salt). In some embodiments, this acid addition salt form of said compound of Formula 1J or 2J is further isolated and/or purified. Without being bound by theory, it is believed that the initial isolation of the compound of Formula 1J or 2J in free form, followed by subsequent conversion of this compound into salt form (e.g., acid addition salt form) results in a final product (compound of Formula 1J or 2J) of higher purity and/or workability.

Step (e) of Method 1J or 2J may be carried out by reacting the free base form of the compound of Formula 1J or 2J with an appropriate acid, in water or in an organic solvent, or in a mixture of the two, to give, for example, a pharmaceutically acceptable acid addition salt of Formula 1J or 2J of the present invention; generally, non-aqueous media such as ether, ethyl acetate, ethanol, isopropanol, isopropyl acetate or acetonitrile are preferred. Appropriate acids may be, for example, hydrochloric, hydrobromic, sulfuric, sulfamic, phosphoric, nitric, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. When a monovalent acid is used (e.g., hydrochloric acid or toluenesulfonic acid), step (e) may result in a mono-addition salt, di-addition salt, or tri-addition salt, or a mixture thereof, depending on the molar equivalent of acid to free base used (e.g., from 1:1 free base to acid to 1:3 free base to acid). Thus, the salt of Formula 1J or 2J may be a mono-tosylate salt, a di-tosylate salt, a tri-tosylate salt or some combination thereof.

In further embodiments of the second aspect, step (e) may result in a particular salt, which salt is isolated and purified, and in an additional step (f), said is converted to a different salt. For example, in some embodiments, step (e) may produce a mono-tosylate salt of the compound of Formula 1J or 2J, which salt is isolated and/or purified, and optionally characterized, e.g., by mass spectrometry, nuclear magnetic resonance spectroscopy, infrared spectroscopy and/or X-ray powder diffraction. Said mono-tosylate salt, for example, may then be combined with an additional amount (e.g., 1 equivalent or slightly more than 1 equivalent) of additional toluenesulfonic acid, in order to yield the di-tosylate salt. Such additional acid may be added as part of the formulation of the compound of Formula 1J or 2J into a pharmaceutical composition, and therefore such step (f) may occurs in the absence of solvent (e.g., in dry blending) or in the presence of solvent (e.g., wet blending).

In specific embodiments of the second aspect, the present disclosure provides:

6.1 Method 1J or 2J, wherein the compound of Formula 1I or 2I is, respectively, a compound according to any of Formula 1.1-1.8 or 2.1-2.8.

6.2 Method 1J or 2J, wherein the substituent A of the compound of Formula 1E or 2E is selected from Br, Cl and I.

6.3 Method 6.2, wherein A is Br.

6.4 Method 1J or 2J, or any of 6.1 et seq., wherein the substituent R of the compounds of Formulas 1E, 1F, 1H and 1I, or 2E, 2F, 2H and 21, is $C_{1-4}$ alkyl (e.g., methyl).

6.5 Method 1J or 2J, or any of 6.1 et seq., wherein the substituent R of the compounds of Formulas 1E and 1F, or 2E and 2F, is H.

6.6 Method 1J or 2J, or any of 6.1 et seq., wherein the protecting group B of the compounds of Formulas 1E, 1F and 1H, or 2E, 2F and 2H, is a group of the formula P-Z, wherein P is selected from $CH_2$, $C(O)$, $C(O)O$ and $S(O)_2$, and wherein Z is an optionally substituted alkyl, aryl, alkylaryl or —OR' wherein R' is alkyl, aryl, arylalkyl or heteroarylalkyl.

6.7 Method 6.6, wherein the protecting group B is an acyl group (e.g., an alkanoyl or alkoxycarbonyl group), for example, t-butoxycarbonyl, phenoxycarbonyl, ethoxycarbonyl, or methoxycarbonyl, or an optionally substituted benzyloxycarbonyl.

6.8 Method 6.7, wherein the protecting group B is ethoxycarbonyl.

6.9 Method 6.6, wherein the protecting group is an optionally substituted benzyl group, e.g., benzyl, 4-methoxybenzyl, or 2,4-dimethoxybenzyl. 6.10 Method 1J or 2J, or any of 6.1 et seq., wherein the transition metal catalyst of step (a) is a copper catalyst.

6.11 Method 6.10, wherein the transition metal catalyst of step (a) is selected from CuI, CuBr, CuCl, $Cu(OAc)_2$, $Cu_2Cl_2$, $CuBr_2$, $CuSO_4$, $Cu_2SO_4$, and $Cu_2O$.

6.12 Method 6.11, wherein the transition metal catalyst of step (a) is selected from CuI, CuBr and CuCl, optionally, where the catalyst is CuI.

6.13 Method 6.12 wherein the transition metal catalyst is CuI.

6.14 Method 1J or 2J, or any of 6.1 et seq., wherein the transition metal catalyst of step (a) is present in an amount of 0.01 to 0.50 equivalents, e.g., from 0.05 to 0.40 equivalents, or from 0.10 to 0.30 equivalents, or from 0.15 to 0.25 equivalents, or about 0.20 equivalents.

6.15 Method 1J or 2J, or any of 6.1 et seq., wherein the base of step (a) is a Bronsted base, for example, selected from amine bases, alkoxides, carbonates and phosphates, and mixtures thereof.

6.16 Method 6.15, wherein the base of step (a) is a carbonate base, for example, an alkali or alkaline earth metal carbonate or bicarbonate, or mixtures thereof.

6.17 Method 6.16, wherein the base of step (a) is selected from sodium carbonate, potassium carbonate, sodium bicarbonate, or potassium bicarbonate, or a mixture thereof.

6.18 Method 6.17, wherein the base of step (a) comprises potassium carbonate, optionally in an amount of 1.5 to 3 equivalents, e.g., 2 to 2.5 equivalents, or about 2.2 equivalents.

6.19 Method 1J or 2J, or any of 6.1 et seq., wherein step (a) does not comprise the base (ii), e.g., does not comprise an alkoxide, carbonate, phosphate or other inorganic base.

6.20 Method 1J or 2J, or any of 6.1 et seq., wherein step (a) comprises an alkali metal iodide, e.g., selected from sodium iodide, potassium iodide, and lithium iodide 6.21 Method 6.20, wherein step (a) comprises potassium iodide.

6.22 Method 1J or 2J, or any of 6.1 et seq., wherein step (a) comprises a mono-dentate or bi-dentate ligand, for example, a ligand selected from phenolic or amine ligands.

6.23 Method 6.22, wherein the ligand is selected from an optionally substituted 1,2-diamine, an optionally substituted 1,2-aminoalcohol, DBU, DBN, or DABCO.

6.24 Method 6.23, wherein the ligand is DBU.

6.25 Method 1J or 2J, or any of 6.1 et seq., wherein the ligand of step (a) is present in an amount of 0.01 to 0.50 equivalents, e.g., from 0.05 to 0.45 equivalents, or from 0.10 to 0.40 equivalents, or from 0.20 to 0.30 equivalents, or about 0.25 equivalents.

6.26 Method 1J or 2J, or any of 6.1 et seq., wherein the solvent for step (a) is toluene or dioxane.

6.27 Method 1J or 2J, or any of 6.1 et seq., wherein the reduction of step (b) is accomplished using a reducing agent selected from metal hydrides, boranes and organoboranes.

6.28 Method 6.27, wherein the reducing agent is selected from boranes, for example, borane ($BH_3$) and borane complexes (e.g., $BH_3$-THF, $BH_3$—$Me_2S$ and $BH_3$—$NH_3$).

6.29 Method 6.28, wherein the reducing agent is borane-THF complex.

6.30 Method 1J or 2J, or any of 6.1 et seq., wherein the solvent for step (b) is a mixture of toluene and THF.

6.31 Method 1J or 2J, or any of 6.1 et seq., wherein the reducing agent of step (b) is present in an amount of 1.5 to 5 equivalents, e.g., 2 to 4 equivalents, or 2.5 to 3.5 equivalents, or about 3 equivalents.

6.32 Method 1J or 2J, or any of 6.1 et seq., wherein the deprotection step (c) is an acid- or base-mediated cleavage reaction, a hydrolysis reaction (e.g., acid- or base-catalysed) or hydrogenation reaction.

6.33 Method 6.32, wherein the deprotection step (c) is an aqueous hydrolysis, e.g., an acidic or basic hydrolysis.

6.34 Method 6.33, wherein the aqueous hydrolysis comprises an acidic catalyst, e.g., selected from hydrochloric acid, hydrobromic acid, sulfuric acid, phosphoric acid, and nitric acid.

6.35 Method 6.33, wherein the aqueous hydrolysis comprises aqueous hydrochloric acid.

6.36 Method 6.33, wherein the aqueous hydrolysis comprises a basic catalyst, e.g., selected from an alkali metal or alkaline earth metal hydroxide, such as sodium hydroxide or potassium hydroxide.

6.37 Method 6.32, wherein the deprotection step (c) is an acid-mediated cleavage, e.g., comprising a strong acid (e.g., hydrochloric acid, trifluoroacetic acid or methanesulfonic acid) optionally neat or in an organic solvent.

6.38 Method 6.32, wherein the deprotection step (c) is a base-mediated cleavage, e.g., comprising an organic base (e.g. piperidine) in an organic solvent.

6.39 Method 6.32, wherein the deprotection step (c) is a hydrogenation reaction, e.g., a catalytic hydrogen comprising a transition metal catalyst (e.g., platinum or palladium) and hydrogen.

6.40 Method 1J or 2J, or any of 6.1 et seq., wherein the compound of Formula 1I or 2I (e.g., the compound of any of 1.1-1.8 or 2.1-2.8) is obtained as a solid, e.g., as an amorphous or crystalline solid.

6.41 Method 1J or 2J, or any of 6.1 et seq., wherein the compound of Formula 1I or 2I (e.g., the compound of any of 1.1-1.8 or 2.1-2.8) is obtained in substantially pure form, e.g., greater than 90 wt % pure, or, e.g., greater than 95 wt % pure, greater than 98.5% pure, up to 100 wt % pure.

6.42 Method 1J or 2J, or any of 6.1 et seq., wherein the compound of Formula 1I or 2I (e.g., the compound of any of 1.1-1.8 or 2.1-2.8) is obtained in free form (i.e., free base form), optionally as a crystalline solid.

6.43 Method 1J or 2J, or any of 6.1 et seq., wherein the compound of Formula 1I or 2I (e.g., the compound of any of 1.1-1.8 or 2.1-2.8) is obtained in salt form, e.g., acid addition salt form.

6.44 Method 6.43, wherein the compound of Formula 1I or 2I (e.g., the compound of any of 1.1-1.8 or 2.1-2.8) is obtained as an addition salt selected from a hydrochloride, hydrobromide, hydroiodide, formate, acetate, trifluoroacetate or methanesulfonate, e.g. in a base to acid molar ratio of 1:1 to 3:1.

6.45 Method 6.44, wherein the compound of Formula 1I or 2I (e.g., the compound of any of 1.1-1.8 or 2.1-2.8) is obtained as a hydrochloride salt, e.g., as a solid hydrochloride salt or crystalline solid hydrochloride salt (e.g., as a mono-hydrochloride salt, di-hydrochloride salt, and/or tri-hydrochloride salt).

6.46 Method 1J or 2J, or any of 6.1 et seq., wherein the method takes place without isolation or without purification of the intermediates of the Formulas 1F and 1H, or 2F and 2H.

6.47 Method 1J or 2J, or any of 6.1 et seq., wherein steps (a), (b) and (c) take place sequentially in a single reaction vessel or set of connected reaction vessels.

6.48 Method 1J or 2J, or any of 6.1 et seq., wherein the compound of Formula 1I or 2I (e.g., the compound of any of 1.1-1.8 or 2.1-2.8) is obtained in a form having less than about 50 ppm of copper, or less than about 10 ppm of copper, or less than about 5 ppm of copper.

6.49 Method 1J or 2J, or any of 6.1 et seq., wherein the compound of Formula 1J or 2J is, respectively, a compound of Formula 3.1-3.15 or 4.1-4.15.

6.50 Method 1J or 2J, or any of 6.1 et seq., wherein the suitable alkylating agent of step (d) is a compound of the general formula Q-X, wherein Q is selected from 4-(4-fluorophenyl)-4-oxobutyl and 3-(4-fluorophenoxy)propyl, and wherein X is any suitable leaving group (e.g., a functional group known in the art to be amenable to nucleophilic substitution reactions).

6.51 Method 6.50, wherein the group X is selected from chloro, bromo, iodo, $C_{1-4}$ alkylsulfonyloxy (e.g. methanesulfonyloxy) and optionally substituted arylsulfonyloxy (e.g., benzenesulfonyloxy, 4-nitrobenzenesulfonyloxy, 4-halosulfonyloxy, and the like).

6.52 Method 1J or 2J, or any of 6.1 et seq., wherein the group Q of the compound of Formula 1J or 2J is 4-(4-fluorophenyl)-4-oxobutyl.

6.53 Method 1J or 2J, or any of 6.1 et seq., wherein the group Q of the compound of Formula 1J or 2J is 3-(4-fluorophenoxy)propyl.

6.54 Method 1J or 2J, or any of 6.1 et seq., wherein the alkylating agent is 4-chloro-4'-fluorobutyrophenone or 1-chloro-3-(4-fluorophenoxy)propane.

6.55 Method 1J or 2J, or any of 6.1 et seq., wherein step (d) comprises the alkylating agent (e.g., 4-chloro-4'-fluorobutyrophenone) in an amount of 1 to 3 equivalents, e.g., 1 to 2 equivalents, or 1.25 to 1.75 equivalents or about 1.5 equivalents, for example, 1.35 to 1.65 equivalents.

6.56 Method 1J or 2J, or any of 6.1 et seq., wherein step (d) further comprises a suitable base, e.g., an organic base (e.g. an amine base) or an inorganic base (e.g., a hydride, alkoxide, aryloxide, carbonate, bicarbonate, phosphate or hydroxide base).

6.57 Method 6.56, wherein the base of step (d) is selected from triethylamine, diisopropylethylamine, sodium carbonate and potassium carbonate.

6.58 Method 6.57, wherein the base of step (d) is sodium carbonate or potassium carbonate.

6.59 Method 6.58, wherein the sodium or potassium carbonate is present in an amount of 1 to 5 equivalents, e.g., 2 to 4 equivalents, or 2.5 to 3.5 equivalents, or about 3 equivalents, for example, 2.7-3.3 equivalents.

6.60 Method 1J or 2J, or any of 6.1 et seq., wherein step (d) further comprises an inorganic iodide salt (e.g., potassium iodide or sodium iodide), optionally, in an amount of 0.75 to 1.5 equivalents, or 1 to 1.25 equivalents, or about 1 equivalent, for example, 0.9-1.1 equivalents.

6.61 Method 1J or 2J, or any of 6.1 et seq., wherein the solvent for step (d) is 3-pentanone.

6.62 Method 1J or 2J, or any of 6.1 et seq., wherein the compound of Formula 1J or 2J is obtained in free base form from step (d).

6.63 Method 1J or 2J, or any of 6.1 et seq., wherein the compound of Formula 1J or 2J is obtained in the form of a salt from step (d), e.g., an acid addition salt (e.g., a hydrochloride salt).

6.64 Method 6.62, wherein the compound of Formula 1J or 2J is obtained in free base form from step (d), and wherein the method further comprises a step (e) of converting said compound of Formula 1J or 2J in free base form into a compound of Formula 1J or 2J in salt form, e.g., acid addition salt form (e.g., a tosylate salt form, mono-tosylate and/or di-tosylate salt form).

6.65 Method 6.64, wherein step (e) is performed by reacting the free base form of the compound of Formula 1J or 2J from step (d) with an appropriate acid in one or more organic solvents, or in water, or in a mixture thereof.

6.66 Method 6.64 or 6.65, wherein the acid of step (e) is toluenesulfonic acid.

6.67 Method 6.66, wherein the amount of toluenesulfonic acid is from 0.9 to 3.2 equivalents, 0.9 to 2.2 equivalents, 0.9 to 1.2 equivalents, e.g., 0.95 to 1.10 equivalents, or 0.95 to 1.05 equivalents, or about 1.0 equivalents, for example, 0.89 to 1.1 equivalents.

6.68 Method 6.66 or 6.67, wherein the solvent for step (e) comprises ethanol, isopropanol, water, methyl tert-butyl ether, or a mixture thereof.

6.69 Method 6.68, wherein the solvent for step (e) substantially comprises isopropanol, e.g., at least 70% by volume isopropanol, or at least 80% by volume isopropanol, or at least 90% by volume isopropanol.

6.70 Method 6.69, wherein the solvent for step (e) consists essentially of isopropanol and methyl tert-butyl ether, e.g., at least 70%, 80% or 90% isopropanol by volume and the balance essentially methyl tert-butyl ether.

6.71 Method 1J or 2J, or any of 6.1 et seq., wherein the method provides the compound of Formula 1J or 2J in free base form.

6.72 Method 1J or 2J, or any of 6.1 et seq., wherein the method provides the compound of Formula 1J or 2J in acid addition salt form.

6.73 Method 6.72, wherein the acid addition salt form is a tosylate salt form (e.g., mono-tosylate, di-tosylate, or tri-tosylate salt form, or a mixture thereof).

6.74 Method 1J or 2J, or any of 6.1 et seq., wherein the method further comprises, after step (e), or if there is no step (e) after step (d), the crystallization and/or recrystallization from a suitable solvent of the initially formed compound of Formula 1J or 2J in salt form, to yield a crystallized or recrystallized compound of Formula 1J or 2J in the same salt form (e.g., either one or two, or more, rounds of crystallization may be used to achieve higher purity).

6.75 Method 6.74, wherein the suitable crystallization solvent for any one or more crystallizations comprises ethanol, isopropanol, water, methyl tert-butyl ether, or a mixture thereof, for example, a first crystallization from isopropanol and a second recrystallization from isopropanol/water.

6.76 Method 6.75, wherein the suitable crystallization solvent for any one or more crystallizations comprises isopropanol and water, optionally in a ratio by volume of 90:10 to 99:1, e.g., from 95:5 to 99:1, or from 97:3 to 99:1 or about 98:2.

6.77 Any of methods 6.74 to 6.76, wherein the recrystallization comprises the addition of a seed crystal (e.g., a seed crystal of the product of the method).

6.78 Method 1J or 2J, or any of 6.1 et seq., wherein the method further comprises a step (f) of converting the initial salt form of the compound of Formula 1J or 2J obtained from step (e) into a different salt form of the compound of Formula 1J or 2J.

6.79 Method 6.78, wherein the new salt form and initial salt form are both acid addition salts.

6.80 Method 6.79, wherein the new salt form is a di- or tri-acid addition salt and the initial salt form is a mono-acid addition salt of the same salt.

6.81 Method 6.80, wherein the new salt form is the bi-tosylate or tri-tosylate salt form and the initial salt form is the mono-tosylate salt form.

6.82 Any of methods 6.79 to 6.81, wherein step (f) comprises the dissolution or suspension of the initial salt form in a suitable solvent followed by the addition of 0.9 to 1.5 equivalents of the appropriate acid (e.g., toluenesulfonic acid), e.g., 0.95 to 1.25 equivalents, or 1.0 to 1.15 equivalents.

6.83 Method 6.82, wherein the suitable solvent is selected from ethanol, isopropanol, water, methyl tert-butyl ether, or a mixture thereof.

6.84 Any of methods 6.78 to 6.83, wherein the initial salt formed in step (e) is isolated and/or purified and/or characterized prior to step (f).

6.85 Method 1J or 2J, or any of 6.1 et seq., wherein the method provides the compound of Formula 1J or 2J in solid form, e.g., solid amorphous form or solid crystalline form.

6.86 Method 1J or 2J, or any of 6.1 et seq., wherein the method provides the compound of Formula 1J or 2J in stable, crystalline salt form, e.g., in a stable crystalline tosylate salt form (e.g., in mono-tosylate, di-tosylate, or tri-tosylate salt form).

6.87 Method 1J or 2J, or any of 6.1 et seq., wherein the method provides the compound of Formula 1J or 2J in at least 70%, preferably at least 80%, more preferably at least 90%, most preferably greater than 95%, up to 100%, cis stereoisomer relative to all other stereoisomers.

6.88 Method 1J or 2J, or any of 6.1 et seq., wherein the method provides the compound of Formula 1J or 2J in substantially enantiomerically pure form, e.g., in at least 90% e.e., preferably in at least 95% e.e., or in at least 97% e.e, or in at least 99% e.e., or at least 99.5% e.e., or in at least 99.9% e.e., up to 100% e.e.

6.89 Method 1J or 2J, or any of 6.1 et seq., wherein the method provides the compound of Formula 1J or 2J in substantially pure form, e.g., as measured by HPLC, for example greater than 95% pure form, or greater than 97%, greater than 98%, greater than 98.5%, greater than 99%, greater than 99.5% or greater than 99.9% pure form, up to 100% pure form.

6.90 Method 1J or 2J, or any of 6.1 et seq., wherein the method provides the compound of Formula 1J or 2J in a form having less than about 50 ppm of copper, or less than about 10 ppm of copper, or less than about 5 ppm of copper.

6.91 Method 1J or 2J, or any of 6.1 to 6.90, wherein the method provides the compound of Formula 1J or 2J in admixture with at least 0.001% by weight and less than 1% by weight of at least one compound selected from the compound of Formula 1K or 2K, 1L or 2L, 1M or 2M, 1N or 2N, 1O or 2O, 1P or 2P, and 1Q or 2Q.

6.92 Method 6.91, wherein the method provides the compound of Formula 1J or 2J in admixture with at least 0.01% by weight and less than 0.5% by weight of at least one compound selected from the compound of Formula 1K or 2K, 1L or 2L, 1M or 2M, 1N or 2N, 1O or 2O, 1P or 2P, and 1Q or 2Q.

6.93 Method 6.91, wherein the method provides the compound of Formula 1J or 2J in admixture with at least 0.01% by weight and less than 0.5% by weight of at least two or at least three or at least four compounds selected from the compound of Formula 1K or 2K, 1L or 2L, 1M or 2M, 1N or 2N, 1O or 2O, 1P or 2P, and 1Q or 2Q.

6.94 Method 6.91, wherein the method provides the compound of Formula 1J in admixture with at least 0.001% by weight and less than 1% by weight of each of the compounds of Formula 1K, 1L, 1M, 1N, 1O, 1P, and 2Q, e.g., at least 0.01% and less than 0.5% by weight of each of said compounds.

6.95 Method 6.91, wherein the method provides the compound of Formula 2J in admixture with at least 0.001% by weight and less than 1% by weight of each of the compounds of Formula 2K, 2L, 2M, 2N, 2O, 2P, and 2Q, e.g., at least 0.0005% and less than 0.5% by weight of each of said compounds.

6.96 Method 6.91, wherein the method provides the compound of Formula 1J in admixture with about 0.01-0.80% by weight of the compound of Formula 1K, and/or about 0.005-0.40% by weight of the compound of Formula 1L, and/or about 0.005-0.30% by weight of the compound of Formula 1M, and/or about 0.01-0.60% by weight of the compound of Formula 1N, and/or about 0.005-0.40% by weight of the compound of Formula 1O, and/or about 0.005-0.45% by weight of the compound of Formula 1P, and/or about 0.0005-0.30% by weight of the compound of Formula 1Q.

6.97 Method 6.91, wherein the method provides the compound of Formula 2J in admixture with about 0.01-0.80% by weight of the compound of Formula 2K, and/or about 0.005-0.40% by weight of the compound of Formula 2L, and/or about 0.005-0.30% by weight of the compound of Formula 2M, and/or about 0.01-0.60% by weight of the compound of Formula 2N, and/or about 0.005-0.40% by weight of the compound of Formula 2O, and/or about 0.005-0.45% by weight of the compound of Formula 2P, and/or about 0.005-0.30% by weight of the compound of Formula 2Q.

6.98 Any of methods 6.91-6.97, wherein in the compound of Formula 1K or 2K, 1L or 2L, 1M or 2M, 1N or 2N, 1O or 2O, 1P or 2P, and 1Q or 2Q, the group R is methyl and the group Q is —(C=O)—.

6.99 Method 1J or 2J, or any of 6.1 to 6.98, wherein the method comprises the isolation and/or purification of the compound of Formula 1J or 2J in mono-tosylate salt form, e.g., in solid crystalline mono-tosylate salt form, and wherein the method further comprises combining the compound of Formula 1J or 2J with at least one molar equivalent of toluenesulfonic acid.

6.100 Method 6.99, wherein the solvent is water and/or an alcoholic solvent (e.g., methanol, ethanol, propanol, butanol) and/or a ketone solvent (e.g., acetone, 2-butanone, 2-pentanone, 3-pentanone, cyclohexanone, cyclopentanone) and/or an ether solvent (e.g., diethyl ether, diisopropyl ether, tetrahydrofuran, 1,4-dioxane, methyl tert-butyl ether), and/or a hydrocarbon solvent (e.g., hexane, pentane, cyclohexane, cyclopentane) or any combination thereof.

6.101 Method 6.99 or 6.100, wherein the mono-tosylate salt of the compound of Formula 1J or 2J is converted, in whole or in part, to a bis-tosylate salt of the compound of Formula 1J or 2J.

6.102 Method 1J or 2J, or any of 6.1 to 6.94, further comprising any or all of the following steps as described in any embodiments thereof herein throughout:

a. Preparing the compound of Formula 1A by reacting 2-bromophenylhydrazine, in free or salt form, with 4-piperidinone, in free or salt form, optionally in hydrate form, optionally in acetic acid solvent;

b. Preparing the compound of Formula 1C or 2C, in free or salt form, by (a) reducing the compound of Formula 1A to a compound of Formula 1B, optionally wherein the reduction comprises reaction of the compound of Formula 1A with triethylsilane and methanesulfonic acid, and (b) separating the stereoisomers of Formula 1B by chiral salt resolution or chiral chromatography to yield the compound of Formula 1C or 2C, optionally wherein the chiral salt resolution is performed in a single resolution step using S-mandelic acid;

c. Preparing the compound of Formula 1D or 2D, in free or salt form, by protecting the piperidine amine of the compound of Formula 1C or 2C with a protecting agent in the presence of a base;

d. Preparing the compound of Formula 1E or 2E, in free or salt form, by N-alkylating a compound of Formula 1D or 2D with (a) a nucleophilic alkyl halide, and (b) a base.

In some embodiments, any of Methods 1I, 2I, 1J, 2J, or 5.1-5.52 or 6.1-6.102, may further comprise the step of preparing a compound of Formula 1C or 2C:

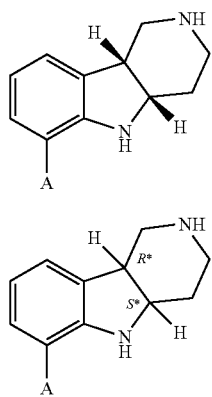

1C

2C in free or salt form, comprises the sub-steps of:
a) reducing a compound of Formula 1A:

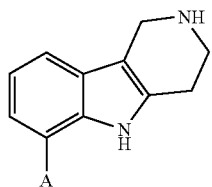

1A to a compound of Formula 1B; and

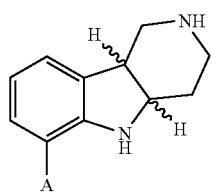

1B wherein substituent A of the compounds of Formulas 1A, 1B, 1C and/or 2C is selected from Br, Cl and I; and
b) separating the stereoisomers (e.g., enantiomers) of compounds of Formula 1B by chiral acid resolution or chiral chromatography to yield the compound of Formula 1C or 2C; optionally wherein the compound of Formula 1C or 2C is at least 70%, preferably at least 80%, more preferably at least 90%, most preferably greater than 95%, and up to 100%, cis stereoisomer relative to all other stereoisomers; and/or wherein the compound of Formula 1C or 2C has an enantiomeric excess (e.e.) (e.g., of the 4aS, 9bR enantiomer, or of the 4aR, 9bS enantiomer) of at least 70%, preferably at least 80%, more preferably at least 90%, most preferably greater than 95% or greater than 97% or greater than 99% or greater than 99.9%, and up to 100%.

The reduction of Compounds of Formula 1A to Compounds of Formula 1B may be accomplished through the use of a reducing agent including, but not limited to: silanes in the presence of an acid (e.g., acetic, methanesulfonic acid or trifluoroacetic acid); metal (e.g., zinc) and mineral acid (e.g. hydrochloric acid); sodium and liquid ammonia; sodium in ethanol; or through the use of borane-amine complexes (e.g. borane-triethylamine in tetrahydrofuran); sodium triacetoxyborohydride; or sodium cyanoborohydride. The conversion of the Compound of Formula 1A to a Compound of Formula 1B may also be accomplished through catalytic hydrogenation, in which the Compound of Formula 1A is treated with hydrogen in the presence of a catalyst such as palladium oxide, palladium on carbon or platinum oxide (See Hudlicky, M., "Reductions in Organic Chemistry", Ellis Horwood, Ltd., Chichester, UK, 1984). The reduction of the Compound of Formula 2A to the Compound of Formula 2B may be accomplished through the use of similar agents as described for the reduction of Compounds of Formula 1A to 1B, for example silanes (e.g., triethylsilane) in the presence of an acid (e.g., acetic, methanesulfonic or trifluoroacetic acid); metal (e.g., zinc) and mineral acid (e.g. hydrochloric acid); sodium and liquid ammonia; sodium in ethanol; or through the use of borane-amine complexes (e.g. borane-triethylamine in tetrahydrofuran); sodium triacetoxyborohydride; or sodium cyanoborohydride. The conversion of the Compound of Formula 2A to the Compound of Formula 2B may also be accomplished through catalytic hydrogenation, in which the Compound of Formula 2A is treated with hydrogen in the presence of a catalyst such as palladium oxide, palladium on carbon or platinum oxide. In an especially preferred embodiment for the reduction of Compounds of Formula 1A or 2A, the reduction is accomplished through the use of triethylsilane in the presence of trifluoroacetic acid, or triethylsilane in the presence of methanesulfonic acid. In particular, it was unexpectedly found that substituting methanesulfonic acid for trifluoroacetic acid significantly improves yield, reaction time and cost efficiency. For example, using 4 volumes of methanesulfonic acid instead of 10 volumes of trifluoroacetic acid permits a significant reduction in need for the costly triethylsilane reagent (From 7 volumes to 1.3 volumes) and reduces reaction time from 45 hours to 2-5 hours, while increasing yield for the step.

In some embodiments, enantiomeric enrichment (or separation) of the isomers of the Compounds of Formula 1B to produce the Compounds of Formula 1C or 2C may be achieved by chiral salt resolution, in which chiral acids such as chiral sulfonic acids or mono- or di-carboxylic acids or derivatives thereof are used. Examples of such acids include, but are not limited to, (+/−)/(R/S) tartaric acid, (+/−)/(R/S) (mono- or di-acetyl)tartaric acid, (+/−)/(R/S) (mono- or di-benzoyl)tartaric acid, (+/−)/(R/S) (mono- or di-pivaloyl) tartaric acid, (+/−)/(R/S) mandelic acid, (+/−)/(R/S) acetoxyphenyl acetic acid, (+/−)/(R/S) methoxyphenyl acetic acid, (+/−)/(R/S) hydroxymandelic acid, (+/−)/(R/S) halomandelic acid (e.g. 4-fluoromandelic acid), (+/−)/(R/S) lactic acid, and (+/−)/(R/S) camphor sulfonic acid. Similarly, the enantiomeric separation of compounds of Formula 2B may be achieved by chiral salt resolution wherein chiral acids such as chiral sulfonic acids or mono- or di-carboxylic acids or derivatives thereof are used. Examples of such acids include, but are not limited to, (+/−)/(R/S) tartaric acid, (+/−)/(R/S) (mono- or di-acetyl)tartaric acid, (+/−)/(R/S) (mono- or di-benzoyl)tartaric acid, (+/−)/(R/S) (mono- or di-pivaloyl)tartaric acid, (+/−)/(R/S) mandelic acid, (+/−)/(R/S) acetoxyphenyl acetic acid, (+/−)/(R/S) methoxyphenyl acetic acid, (+/−)/(R/S) hydroxymandelic acid, (+/−)/(R/S) halomandelic acid (e.g. 4-fluoromandelic acid), (+/−)/(R/S) lactic acid, and (+/−)/(R/S) camphor sulfonic acid. Preferably, resolution of compounds of Formula 1B or 2B is accomplished by using mandelic acid. In an especially preferred embodiment, said acid is (S)-(+)-mandelic acid. Resolution may be optimized where undesired enantiomer is removed first. Therefore, in another preferred embodiment, resolution is accomplished by adding (R)-(−)-mandelic acid to remove the undesired enantiomer first, followed by the addition of (S)-(+)-mandelic acid to obtain the desired product. In some embodiments, only a single resolution is performed using only (S)-(+)-mandelic acid. Preferred solvents for the resolution include methanol, ethanol, methyl tert-butyl ether (MTBE), and combinations thereof.

In another embodiment, enantiomeric enrichment (or separation) of the stereoisomers of the Compounds of Formula 1B may be achieved by using chiral chromatography, for example using amylose tris(3,5-dimethylphenylcarbamate) column sold under the tradename "CHIRALPAK® AD®". The isomers of Formula 1B may be separated and eluted with a mobile phase such as ethanol at a flow rate of 100-450 mL/min. In yet another embodiment, the isomers of Formula 1B may be separated and eluted with mobile phase such as methanol or isopropyl alcohol. The fractions for the desired compounds, preferably, Compounds of Formula 1C or 2C, may be collected and isolated. In one embodiment, chiral chromatography comprises the use of CHIRALPAK® AD®, 20 μm, 5 cm ID×50 cm L column and 100% ethanol mobile phase at a flow rate of 150 mL/min. In another embodiment, chiral chromatography comprises the use of CHIRALPAK® AD®, 20 μm, 11 cm ID×25 cm L column and 100% ethanol mobile phase at a flow rate of 400 mL/min.

It is understood that upon the separation of the isomers of the Compounds of Formula 1B to yield the Compounds of Formula 1C or 2C, the diastereomeric or enantiomeric composition of the Compounds becomes fixed, or substantially fixed, as all further reactions in the sequence arriving at the Compound of Formula 1J or 2J do not substantially change the diastereomeric or enantiomeric composition of the Compounds. Thus, in all aspects and embodiments of the present disclosure, each of the intermediates according to Formulas 1D, 1E, 1F, 1H, and 1I, may each be substantially, essentially, or completely a single cis enantiomer, to the substantial or complete exclusion of the opposite cis isomer or any trans isomer. Likewise, in all aspects and embodiments of the present disclosure, each of the intermediates according to Formulas 2D, 2E, 2F, 2H, and 2I, may each be substantially, essentially, or completely a single cis enantiomer, specifically the 4aS, 9bR enantiomer, to the substantial or complete exclusion of the opposite cis isomer or any trans isomer. Thus, as used herein, each of the intermediates according to Formulas 1D, 2D, 1E, 2E, 1F, 2F, 1H, 2H, 1I and 2I, may be at least 70%, preferably at least 80%, more preferably at least 90%, most preferably greater than 95%, and up to 100%, cis stereoisomer relative to all other stereoisomers; and/or have an enantiomeric excess (e.e.) of at least 70%, preferably at least 80%, more preferably at least 90%, most preferably greater than 95%, or greater than 97%, or greater than 98.5%, or greater than 99%, or greater than 99.9%, and up to 100%.

In some embodiments, any of Methods 1I, 2I, 1J, 2J, or 5.1-5.52 or 6.1-6.102, may further comprise the step of preparing the compound of Formula 1A, in free or salt form, by reacting 2-bromophenylhydrazine with 4-piperidinone in an acidic solvent (a Fischer Indole reaction). In some embodiments the 2-bromophenylhydrazine and/or the 4-piperidinone is provided as an acid addition salt, for example, a hydrochloride, hydrobromide, acetate or trifluoroacetate salt. In some embodiments, the 4-piperidinone is present as a hydrate, e.g., a monohydrate. In some embodiments, the product is obtained as an acid addition salt, e.g., a hydrochloride, hydrobromide, trifluoroacetate, sulfate, or acetate salt. The reaction may be carried out in any suitable solvent, for example, an aqueous or alcoholic solvent (e.g., water, methanol, ethanol or isopropanol, or any mixture thereof) comprising a dissolved acid (e.g., HCl, HBr, $H_2SO_4$, acetic acid), or in a neat acidic solvent (e.g., acetic acid, trifluoroacetic acid). In some embodiments, the yield may be improved by using a solvent in which the product is poorly soluble. In some embodiments, the yield is improved by using neat acetic acid as the solvent.

In some embodiments, any of Methods 1I, 2I, 1J, 2J, or 5.1-5.52 or 6.1-6.102, may further comprise the step of preparing a compound of Formula 1D or 2D:

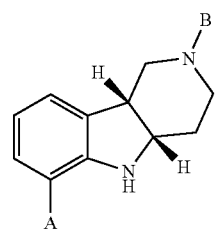

1D

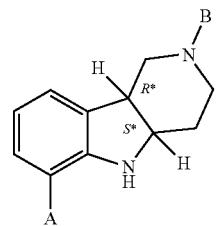

2D wherein:
(i) A is selected from Br, Cl and I; and
(ii) B is a protecting group, as defined herein; in free or salt form,
comprising the step of protecting the piperidine amine of the compound of Formula 1C or 2C with a protecting agent in the presence of a base;
wherein said protecting agent is a compound of the general formula:

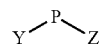

wherein:
(i) Y is halogen, imidazoyl, benzotriazole, N-(oxy)succinimide, alkoxy, —O— alkylaryl or —O-aryl;
(ii) Z is optionally substituted alkyl, aryl, alkylaryl or —OR wherein R is alkyl, aryl, arylalkyl or heteroarylalkyl;
(iii) P is —CH$_2$—, —C(O)—, —C(O)O— or S(O)$_2$.

Examples of suitable protecting agent for reaction with the compounds of Formula 1C or 2C include, but are not limited to, benzyloxycarbonyl chloride (Cbz-Cl), triphenylmethyl chloride, ethyl chloroformate, t-butoxycarbonyl anhydride (Boc$_2$O), benzyl N-succinimidyl carbonate, or benzoyl halide (e.g. benzoyl chloride or bromide), (benzyloxycarbonyl)-benzo triazole, benzyl halide (e.g. benzyl chloride or bromide), 1-arene sulfonyl chloride or toluene sulfonyl chloride. Another example of a protecting group of Compounds of Formula 1C or 2C is p-methoxybenzyl, which may be prepared using p-methoxybenzyl chloride, p-methoxybenzyl bromide or p-methoxybenzaldehyde. The protective agents disclosed herein are not intended to be exhaustive. For further examples of amine protecting agent, see one of the many general texts on the subject, for example, "Protective Groups in Organic Synthesis" by Theodora Green (publisher: John Wiley & Sons), the disclosure of which is hereby incorporated by reference. Upon addition of the protecting agent to the compounds of Formula 1C or 2C, the substituent B of the resulting compound 1D or 2D therefore has the general formula:

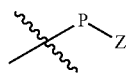

wherein:
(i) Z is optionally substituted alkyl, aryl, alkylaryl or —OR wherein R is alkyl, aryl, arylalkyl or heteroarylalkyl;
(ii) P is —CH$_2$—, —C(O)—, —C(O)O— or S(O)$_2$.

The protection step of this embodiment generally requires the addition of a base such as: butyl lithium or metal hydrides (e.g., potassium hydride); bicarbonates, carbonates, or hydroxides of alkali or alkaline earth metals (e.g., potassium or sodium carbonate, sodium bicarbonate, or sodium hydroxide), or organic amines (e.g., triethylamine). Preferably, the protecting agent of compounds of Formula 1D or 2D is ethyl chloroformate or BOC anhydride. In an especially preferred embodiment, said protecting agent is ethyl chloroformate and said base is triethylamine or sodium hydroxide.

In some embodiments, the conversion of the compound of Formula 1C or 2C to the compound of Formula 1D or 2D comprises treatment with ethyl chloroformate and sodium hydroxide in a mixture of water and THF.

In some embodiments, the procedure for protecting the piperidine nitrogen of the compound of Formula 1C or 2C will entail first neutralizing a salt of the compound of Formula 1C or 2C, for example a mandelic acid salt, with a suitable base, followed by isolation, separation, or purification of the free base of the compound of Formula 1C or 2C. The appropriate reagents for the protection of the piperidine nitrogen of the compound of Formula 1C or 2C are then added, along with suitable base to yield the compound of Formula 1D or 2D. The base used for neutralization may or may not be the base used for the protection reaction. In other embodiments, the salt of the compound of Formula 1C or 2C (e.g., the mandelate salt) is reacted with the appropriate protection reagents in the presence of excess base, in order to arrive at the compound of Formula 1D or 2D in a single step. Thus, the free base formation and acylation reactions are conducted simultaneously in these embodiments. Preferably the base is sodium hydroxide.

In some embodiments, any of Methods 1I, 2I, 1J, 2J, or 5.1-5.52 or 6.1-6.102, may further comprise the step of preparing a compound of Formula 1E or 2E:

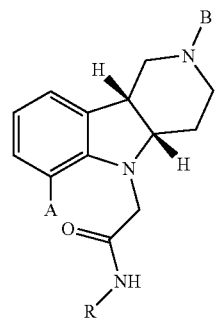

1E

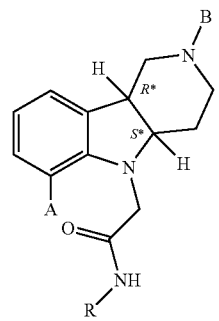

2E wherein:
(i) A is selected from Br, Cl and I;
(ii) R is selected from H and C$_{1-4}$ alkyl (e.g. methyl); and
(iii) B is a protecting group, as defined herein; in free or salt form, comprising the step of N-alkylating a compound of Formula 1D or 2D, as hereinbefore described, with (a) a nucleophilic alkyl halide of the general formula:

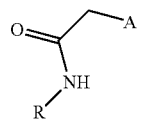

wherein:
(i) A=Cl, F, Br or I; and
(ii) R is H or C$_{1-4}$ alkyl; and (b) a base.

Examples of nucleophilic alkyl halides suitable for the alkylation of the compounds of Formula 1D and 2D include, but are not limited to, 2-chloroacetamide, 2-bromoacetamide, N—C$_{1-4}$ alkyl 2-chloroacetamides (e.g., N-methyl 2-chloroacetamide), and N—C$_{1-4}$ alkyl 2-bromoacetamides (e.g., N-methyl 2-bromoacetamide). Examples of bases useful for said alkylation include, but are not limited to, organic bases such as amine bases (e.g., ammonia, triethylamine, N,N'-diisopropylethylamine or 4-(dimethylamino)pyridine (DMAP), 1,5-diazabicycl[4.3.0]-non-5-ene (DBN), 1,5-diazabicyclo[5.4.0]undec-5-ene (DBU)); or inorganic bases such as hydrides (e.g. sodium, lithium or potassium hydride), alkoxides (e.g. sodium, potassium or lithium t-butoxide and K(OAr), Na(OAr)), or carbonates, bicarbonates, phosphates or hydroxides of alkali or alkaline earth metals (e.g. sodium, magnesium, calcium, potassium, cesium or barium carbonate, bicarbonate, hydroxide or phosphate). Optionally, such N-alkylation reaction may be achieved in the presence of an iodide source such as potassium iodide or sodium iodide, preferably potassium iodide. In particular embodiments, the alkylation may be carried out using 2-chloroacetamide or N-methyl 2-chloroacetamide in the presence of N,N'-diisopropylethylamine and potassium iodide in dimethylacetamide solvent. Suitable solvents also include acetonitrile, dioxane, dimethylformamide and dimethylacetamide.

In another aspect, the present disclosure provides an active pharmaceutical composition (active pharmaceutical ingredient, i.e., API) comprising the compound of Formula 1J or 2J, in substantially pure form. In further embodiments of this aspect, the present disclosure provides:

7.1 An active pharmaceutical composition (active pharmaceutical ingredient) comprising the compound of Formula 1J or 2J in pharmaceutically acceptable salt form, wherein the composition comprises at least 97% by weight of said compound (measured as the salt form).

7.2 Composition 7.1, wherein the compound is the compound of Formula 1J, wherein R is methyl and Q is 3-(4-fluorophenyl)-4-oxobutyl.

7.3 Composition 7.2, wherein said compound is in substantially enantiomerically pure form, e.g., at least 97% e.e., or in at least 98% e.e, or in at least 98.5% e.e., or in at least 99% e.e., up to 100% e.e.

7.4 Composition 7.2 or 7.3, wherein the composition comprises the compound is in at least 98%, at least 98.5% or at least 99.0% by weight (measured as the salt form).

7.5 Any of Compositions 7.2-7.4, wherein the compound is in tosylate or hydrochloride salt form (e.g., mono-, di- or tri-tosylate salt form, or mono-, di- or tri-hydrochloride salt form).

7.6 Composition 7.5, wherein the compound is in mono-tosylate salt form (i.e., wherein the composition comprises at least 97% by weight of the compound in mono-tosylate salt form).

7.7 Composition 7.6, wherein the compound is in mono-tosylate salt form and the composition comprises the compound in at least 98%, at least 98.5% or at least 99.0% by weight (measured as the mono-tosylate salt).

7.8 Any of Compositions 7.1 to 7.7, wherein the compound is in crystalline salt form.

7.9 Any of Compositions 7.1 to 7.7, wherein the composition comprises not more than 0.50% by weight of each of any Compound of Formula 1A, 1B, 1C, 1D, 2D, 1E, 2E, 1F, 2F, 1H, 2H, 1I or 2I, for example, not more than 0.40% by weight of each, or not more than 0.30% by weight of each.

7.10 Any of Compositions 7.1 to 7.8, wherein the composition comprises not more than 0.25% by weight of a Compound of Formula 1I or 2I (e.g., wherein R is methyl).

7.11 Any of Compositions 7.1 to 7.10, wherein the composition comprises not more than 50 ppm of copper, e.g., not more than 40 ppm, or not more than 25 ppm, or not more than 10 ppm of copper.

7.12 Any of Compositions 7.1 to 7.11, wherein the composition comprises at least 0.001% by weight and less than 1% by weight of at least one compound selected from the compound of Formula 1K or 2K, 1L or 2L, 1M or 2M, 1N or 2N, 1O or 2O, 1P or 2P, and 1Q or 2Q.

7.13 Any of Compositions 7.1 to 7.11, wherein the composition comprises the compound of Formula 1J or 2J in admixture with at least 0.005% by weight and less than 0.5% by weight of at least one compound selected from the compound of Formula 1K or 2K, 1L or 2L, 1M or 2M, 1N or 2N, 1O or 2O, 1P or 2P, and 1Q or 2Q.

7.14 Any of Compositions 7.1 to 7.11, wherein the composition comprises the compound of Formula 1J or 2J in admixture with at least 0.005% by weight and less than 0.5% by weight of at least two or at least three or at least four compounds selected from the compound of Formula 1K or 2K, 1L or 2L, 1M or 2M, 1N or 2N, 1O or 2O, 1P or 2P, and 1Q or 2Q.

7.15 Any of Compositions 7.1 to 7.11, wherein the composition comprises the compound of Formula 1J in admixture with at least 0.001% by weight and less than 1% by weight of each of the compounds of Formula 1K, 1L, 1M, 1N, 1O, 1P, and 2Q, e.g., at least 0.01% and less than 0.5% by weight of each of said compounds.

7.16 Any of Compositions 7.1 to 7.11, wherein the composition comprises the compound of Formula 2J in admixture with at least 0.001% by weight and less than 1% by weight of each of the compounds of Formula 2K, 2L, 2M, 2N, 2O, 2P, and 2Q, e.g., at least 0.01% and less than 0.5% by weight of each of said compounds.

7.17 Any of Compositions 7.1 to 7.11, wherein the composition comprises the compound of Formula 1J in admixture with about 0.01-0.80% by weight of the compound of Formula 1K, and/or about 0.005-0.40% by weight of the compound of Formula 1L, and/or about 0.005-0.30% by weight of the compound of Formula 1M, and/or about 0.01-0.60% by weight of the compound of Formula 1N, and/or about 0.005-0.40% by weight of the compound of Formula 1O, and/or about 0.005-0.45% by weight of the compound of Formula 1P, and/or about 0.005-0.30% by weight of the compound of Formula 1Q.

7.18 Any of Compositions 7.1 to 7.11, wherein the composition comprises the compound of Formula 2J in admixture with about 0.01-0.80% by weight of the compound of Formula 2K, and/or about 0.005-0.40% by weight of the compound of Formula 2L, and/or about 0.005-0.30% by weight of the compound of Formula 2M, and/or about 0.01-0.60% by weight of the compound of Formula 2N, and/or about 0.005-0.40% by weight of the compound of Formula 2O, and/or about 0.005-0.45% by weight of the compound of Formula 2P, and/or about 0.005-0.30% by weight of the compound of Formula 2Q.

7.19 Any of compositions 7.12 to 7.19, wherein in the compound of Formula 1K or 2K, 1L or 2L, 1M or 2M, 1N or 2N, 1O or 2O, 1P or 2P, and 1Q or 2Q, the group R is methyl and the group Q is —(C=O)—.

7.20 Any of Compositions 7.1 to 7.19, wherein the Compound of Formula 1J or 2J is a compound manufactured according to any of Methods 1J, 2J or 6.1-6.102, or any of Methods 1K, 2K or 8.1-8.49.

In another aspect, the present disclosure provides a Pharmaceutical Composition comprising the active pharmaceutical composition (active pharmaceutical ingredient) according to any of compositions 7.1-7.20 in admixture with one or more pharmaceutically acceptable excipients, diluents, or solvents. In some embodiments, the Pharmaceutical Composition is selected from a tablet, capsule, caplet, powder, wafer, gel, or sterile injectable solution. In some embodiments, the Pharmaceutical Composition is an orally disintegrating tablet. In some embodiments, the Pharmaceutical Composition is a long-acting injectable composition, e.g., for intramuscular or subcutaneous administration. In some embodiments, the Pharmaceutical Composition comprises from 1 to 60 mg of the Compound of Formula 1J or 2J, measured by weight of the equivalent free base (e.g., from 20-60 mg, or 20-40 mg, or 40-60 mg, for an oral ingested dosage form; e.g., from 1-30 mg, or 5-20 mg, or 5-15 mg, or 1-10 mg, for an oral rapidly dissolving dosage form).

In a particular embodiment, the Pharmaceutical Composition comprises 40-42 mg of Compound of Formula 1J or 2J, measured by weight of the equivalent free base; for example, a Pharmaceutical composition comprising 60 mg of the Compound of Formula 1J or 2J, wherein R is methyl and Q is 4-(4-fluorophenyl)-4-oxobutyl and the Compound is in monotosylate acid addition salt form.

In another embodiment, the present disclosure provides a Pharmaceutical Composition comprising a Compound of Formula 1J or 2J, or any of 3.1-3.15 or 4.1-4.15, wherein the Compound is in admixture with toluenesulfonic acid and at least one excipient, diluent, or solvent. For example, in some embodiments, the Pharmaceutical Composition comprising a Compound of Formula 1J or 2J in toluenesulfonic acid addition salt form in admixture with toluenesulfonic acid. In some embodiments, the toluenesulfonic acid is present in an amount of at least 1 molar equivalent to the amount of the Compound of Formula 1J or 2J present in the Composition, e.g., about 1 molar equivalent, or 1-1.15 molar equivalents, 1-1.5 molar equivalent, or 1-2 molar equivalents. The Composition may be, for example, a solid oral dosage form, such as a tablet, capsule, or orally dissolving tablet. The Compound of Formula 1J or 2J is preferably a Compound wherein R is methyl and Q is 4-(4-fluorophenyl)-4-oxobutyl.

Examples of suitable excipients, diluents and solvents for a Pharmaceutical Composition include, but are not limited to: cellulose acetate, cellulose acetate phthalate, methacrylate/methyl acrylate copolymer, hydroxypropyl cellulose, hydroxypropyl methyl cellulose, hydroxypropyl methyl cellulose acetate succinate (HPMC-AS), hydroxypropyl methyl cellulose phthalate (HPMC-P), polyvinyl acetate, polyvinyl pyrrolidone, polyvinyl pyrrolidone/vinyl acetate copolymer, polyethylene glycol/polyvinyl acetate/polyvinylcaprolactam copolymer, tocopherol, butylated hydroxytoluene (BHT), propyl gallate (OPG), ascorbic acid, butylated hydroxyanisole (BHA), tert-Butylhydroquinone (TBHQ), carotenoids, glutathione, sodium metabisulfite, sodium ethylenediaminetetraacetate, cysteine, methionine, sesamol, citric acid, and surfactants (e.g., anionic, cationic, zwitterionic or neutral surfactants). Generally, suitable excipients can be selected from the following categories: (a) diluent/filler (e.g., cellulose or microcrystalline cellulose (e.g., silicified microcrystalline cellulose), mannitol, lactose monohydrate, dicalcium phosphate, or isomalt), (b) binder (e.g., hydroxypropyl cellulose, hydroxypropyl methyl cellulose, copovidone), (c) disintegrant (e.g., sodium starch glycolate, crospovidone or croscarmellose sodium), (d) lubricant (e.g., magnesium stearate or glyceryl monostearate), (e) glidant (e.g., silicon dioxide or talc), (f) effervescent, (g) polymer, (h) plasticizer, (i) drying agent or desiccant, (j) humectant (e.g., polyol), (k) wetting agent, (l) anti-oxidant (e.g., BHT, citric acid, propyl gallate, ascorbic acid or sodium metabisulfite), (m) thickening agent (e.g., gelling agent), (n) surfactant, (o) buffer, (p) sweetener or flavor, and (q) dye or colorant.

As used herein, "active pharmaceutical composition" refers to an active pharmaceutical ingredient (API) intended for incorporation into a pharmaceutical composition for administration to the body of a human or animal subject. As such, an API consists only of the active medicinal compound (e.g., the compound of Formula 1J or 2J) and any incidental impurities resulting from its synthesis. In contrast a "pharmaceutical composition" comprises an API in admixture with at least one excipient, diluent, or solvent. Suitable excipients, diluents and solvents are known in the art and include, but are not limited to, binders, disintegrants, polymers, sugars, fillers, sweeteners, adhesives, buffers, release-modulating agents, protective coatings (e.g., gastric coatings), colorants, flavors, and liquid carriers (including water, ethanol, glycerol, sorbitol, propylene glycol, and the like).

In another aspect, the present disclosure provides a method (Method 1K) for preparing a compound of Formula 1J, or any of 3.1-3.15 (as appropriate), wherein the compound of Formula 1J is in pharmaceutically acceptable salt form, wherein the method comprises the step of (a) converting a compound of Formula 1J in free form or in salt form into the compound of Formula 1J (or any of 3.1-3.15) in pharmaceutically acceptable salt form (e.g., in a different salt form), such as acid addition salt form (e.g., tosylate salt form). Thus, for example, step (a) may involve converting a compound of Formula 1J in a non-pharmaceutically acceptable salt form into a compound of Formula 1J in pharmaceutically acceptable salt form. Alternatively, step (a) may involve converting a compound of Formula 1J in a less-preferred pharmaceutically acceptable salt form (e.g., hydrochloride) into a more-preferred pharmaceutically acceptable salt form (e.g., tosylate). In some embodiments, step (a) may involve converting a compound of Formula 1J in monotosylate salt form into a compound of Formula 1J in di-tosylate salt form.

In another aspect, the present disclosure provides a method (Method 2K) for preparing a compound of Formula 2J, or any of 4.1-4.15 (as appropriate), wherein the compound of Formula 2J is in pharmaceutically acceptable salt form, wherein the method comprises the step of (a) converting a compound of Formula 2J in free form or in salt form into the compound of Formula 2J (or any of 4.1-4.15) in pharmaceutically acceptable salt form (e.g., in a different salt form), such as acid addition salt form (e.g., tosylate salt form). Thus, for example, step (a) may involve converting a compound of Formula 2J in a non-pharmaceutically acceptable salt form into a compound of Formula 2J in pharmaceutically acceptable salt form. Alternatively, step (a) may involve converting a compound of Formula 2J in a less-preferred pharmaceutically acceptable salt form (e.g., hydrochloride) into a more-preferred pharmaceutically acceptable salt form (e.g., tosylate). In some embodiments, step (a) may involve converting a compound of Formula 2J in monotosylate salt form into a compound of Formula 2J in di-tosylate salt form.

In all respects, steps (a) of Method 1K and 2K may be carried out according to the description above for step (e) or step (f) of Method 1J and 2J, respectively. For example, when step (a) of Method 1K or 2K involves converting the compound of Formula 1J or 2J in free base form into a compound of Formula 1J or 2J in salt form, then the method may be carried out according to the description above for step (e) of Method 1J or 2J, respectively. When step (a) of Method 1K or 2K involves converting the compound of Formula 1J or 2J in salt form into a compound of Formula 1J or 2J in a different salt form, then the method may be carried out according to the description above for step (f) of Method 1J or 2J, respectively.

In further embodiments of Method 1K and 2K, the present disclosure provides:

- 8.1 Method 1K or 2K, wherein the method begins with a compound of Formula 1J or 2J in free base form, and wherein the method comprises the step (a) of converting said compound of Formula 1J or 2J in free base form into the compound of Formula 1J or 2J in pharmaceutically acceptable salt form, e.g., acid addition salt form (e.g., a tosylate salt form, e.g., mono-tosylate and/or di-tosylate salt form).
- 8.2 Method 8.1, wherein step (a) is performed by reacting the initial free base form of the compound of Formula 1J or 2J with an appropriate acid in one or more organic solvents, or in water, or in a mixture thereof.
- 8.3 Method 1K or 2K, wherein the method begins with a compound of Formula 1J or 2J in salt form, e.g., acid addition salt form, and wherein the method comprises the step (a) of converting said compound of Formula 1J or 2J in salt form into the compound of Formula 1J or 2J in pharmaceutically acceptable salt form which is a different salt form, e.g., a different acid addition salt form (e.g., a tosylate salt form, e.g., mono-tosylate and/or di-tosylate salt form).
- 8.4 Method 8.3, wherein step (a) is performed by reacting the initial salt form of the compound of Formula 1J or 2J with an appropriate acid in one or more organic solvents, or in water, or in a mixture thereof.
- 8.5 Method 8.2, or 8.4, wherein the appropriate acid of step (a) is toluenesulfonic acid.
- 8.6 Method 8.5, wherein the amount of toluenesulfonic acid is from 0.9 to 3.2 equivalents, 0.9 to 2.2 equivalents, 0.9 to 1.2 equivalents, e.g., 0.95 to 1.10 equivalents, or 0.95 to 1.05 equivalents, or about 1.0 equivalents, for example, 0.89 to 1.1 equivalents.
- 8.7 Method 1K or 2K, or any of 8.1 et seq., wherein the solvent for step (a) comprises methanol, ethanol, isopropanol, n-propanol, isobutanol, n-butanol, t-butanol, water, methyl tert-butyl ether, dioxane, diethyl ether, diisopropyl ether, or a mixture thereof.
- 8.8 Method 8.7, wherein the solvent for step (a) substantially comprises isopropanol, e.g., at least 70% by volume isopropanol, or at least 80% by volume isopropanol, or at least 90% by volume isopropanol.
- 8.9 Method 8.8, wherein the solvent for step (a) consists essentially of isopropanol and methyl tert-butyl ether, e.g., at least 70%, 80% or 90% isopropanol by volume and the balance essentially methyl tert-butyl ether.
- 8.10 Method 1K or 2K, or any of 8.1 et seq., wherein the method provides the compound of Formula 1J or 2J in pharmaceutically acceptable acid addition salt form.
- 8.11 Method 8.10, wherein the acid addition salt form is a tosylate salt form (e.g., mono-tosylate, di-tosylate, or tri-tosylate salt form, or a mixture thereof).
- 8.12 Any of Methods 8.3-8.12, wherein the initial salt form of the compound of Formula 1J or 2J is a toluenesulfonic acid addition salt form (e.g., monotosylate) and wherein the salt form of the compound of Formula 1J or 2J after step (a) is a different toluenesulfonic acid addition salt form (e.g., a di-tosylate).
- 8.13 Any of Methods 8.3-8.12, wherein the initial salt form of the compound of Formula 1J or 2J is a hydrochloride acid addition salt form (e.g., mono-HCl or di-HCl) and wherein the salt form of the compound of Formula 1J or 2J after step (a) is a toluenesulfonic acid addition salt form (e.g., a monotosylate or di-tosylate).
- 8.14 Method 1K or 2K, or any of 8.1 et seq., wherein the method further comprises, after step (a), a step (b) of crystallization and/or recrystallization from a suitable solvent of the initially formed compound of Formula 1J or 2J in salt form (from step (a)), to yield a crystallized or recrystallized compound of Formula 1J or 2J in the same salt form (e.g., either one or two, or more, rounds of crystallization may be used to achieve higher purity).
- 8.15 Method 8.14, wherein the suitable crystallization solvent for any one or more crystallizations comprises ethanol, isopropanol, water, methyl tert-butyl ether, or a mixture thereof, for example, a first crystallization from isopropanol and a second recrystallization from isopropanol/water.
- 8.16 Method 8.15, wherein the suitable crystallization solvent for any one or more crystallizations comprises isopropanol and water, optionally in a ratio by volume of 90:10 to 99:1, e.g., from 95:5 to 99:1, or from 97:3 to 99:1 or about 98:2.
- 8.17 Any of methods 8.14 to 8.16, wherein the recrystallization comprises the addition of a seed crystal (e.g., a seed crystal of the product of the method).
- 8.18 Method 1K or 2K, or any of 8.1 et seq., wherein the method begins with a compound of Formula 1J or 2J in salt form, and wherein the method further comprises a step prior to step (a) as described above, of converting the initial salt form of the compound of Formula 1J or 2J into a free base form, and thereafter converting said free base form into a salt form according to step (a), as described above.
- 8.19 Method 8.18, wherein the prior step comprises treating the initial salt form of the compound of Formula 1J or 2J with a suitable base in a suitable solvent.
- 8.20 Method 8.19, wherein the suitable base is an inorganic base, such as a hydroxide, oxide, carbonate or bicarbonate of an alkali metal or alkaline earth metal.
- 8.21 Method 8.20, wherein the base is selected from NaOH, KOH, LiOH, Ca(OH)$_2$, Mg(OH)$_2$, CaO, MgO, Na$_2$CO$_3$, K$_2$CO$_3$, Li$_2$CO$_3$, NaHCO$_3$, KHCO$_3$, LiHCO$_3$, CaCO$_3$, and MgCO$_3$.
- 8.22 Method 8.19, 8.20 or 8.21, wherein the suitable solvent is selected from water, methanol, ethanol, isopropanol, n-propanol, isobutanol, n-butanol, t-butanol, THF, dioxane, methyl t-butyl ether, or any combination thereof.
- 8.23 Any of Methods 8.18-8.22, wherein the initial salt form is an acid addition salt form, e.g., hydrochloride, hydrobromide, hydroiodide, sulfate, phosphate, methanesulfonate, or toluenesulfonate (e.g., monotosylate or di-tosylate).
- 8.24 Any of Methods 8.18-8.22, wherein the salt form of the compound of Formula 1J or 2J after step (a) is a toluenesulfonic acid addition salt form (e.g., a monotosylate or di-tosylate).
- 8.25 Method 1K or 2K, or any of 8.1 et seq., wherein the method begins with a compound of Formula 1J or 2J in free base form, and wherein the method further comprises a step prior to step (a) as described above, of converting the free base form of the compound of Formula 1J or 2J into an intermediate salt form, and thereafter converting said intermediate salt form into a final salt form according to step (a), as described above.

8.26 Method 8.25, wherein the initial salt form is an acid addition salt form, e.g., hydrochloride, hydrobromide, hydroiodide, sulfate, phosphate, methanesulfonate, or toluenesulfonate (e.g., monotosylate).

8.27 Method 8.25 or 8.26 wherein the prior step is performed by reacting the initial free base form of the compound of Formula 1J or 2J with an appropriate acid in one or more organic solvents, or in water, or in a mixture thereof, to yield the intermediate salt form.

8.28 Method 8.22, 8.23 or 8.24 wherein the solvent for the prior step comprises water, methanol, ethanol, isopropanol, n-propanol, isobutanol, n-butanol, t-butanol, THF, dioxane, methyl t-butyl ether, or any combination thereof.

8.29 Method 8.27 or 8.28 wherein the appropriate acid is toluenesulfonic acid.

8.30 Any of Methods 8.25-8.29, wherein the salt form of the compound of Formula 1J or 2J after step (a) is a toluenesulfonic acid addition salt form (e.g., a mono-tosylate or di-tosylate).

8.31 Method 1K or 2K, or any of 8.1 et seq., wherein the method provides the compound of Formula 1J or 2J in solid form, e.g., solid amorphous form or solid crystalline form.

8.32 Method 1K or 2K, or any of 8.1 et seq., wherein the method provides the compound of Formula 1J or 2J in stable, crystalline salt form, e.g., in a stable crystalline tosylate salt form (e.g., in mono-tosylate, di-tosylate, or tri-tosylate salt form).

8.33 Method 1K or 2K, or any of 8.1 et seq., wherein the method begins with a compound of Formula 1J or 2J in stable, crystalline salt form.

8.34 Method 8.33, wherein the method begins with a compound of Formula 1J or 2J in stable, crystalline toluenesulfonic acid addition salt form (e.g., in mono-tosylate, di-tosylate or tri-tosylate salt form).

8.35 Method 1K or 2K, or any of 8.1 et seq., wherein the method provides the compound of Formula 1J or 2J in at least 70%, preferably at least 80%, more preferably at least 90%, most preferably greater than 95%, up to 100%, cis stereoisomer relative to all other stereoisomers.

8.36 Method 1K or 2K, or any of 8.1 et seq., wherein the method provides the compound of Formula 1J or 2J in substantially enantiomerically pure form, e.g., in at least 90% e.e., preferably in at least 95% e.e., or in at least 97% e.e, or in at least 99% e.e., or at least 99.5% e.e., or in at least 99.9% e.e., up to 100% e.e.

8.37 Method 1K or 2K, or any of 8.1 et seq., wherein the method provides the compound of Formula 1J or 2J in substantially pure form, e.g., as measured by HPLC, for example greater than 95% pure form, or greater than 97%, greater than 98%, greater than 98.5%, greater than 99%, greater than 99.5% or greater than 99.9% pure form, up to 100% pure form.

8.38 Method 1K or 2K, or any of 8.1 et seq., wherein the method provides the compound of Formula 1J or 2J in a form having less than about 50 ppm of copper, or less than about 10 ppm of copper, or less than about 5 ppm of copper.

8.39 Method 1K or 2K, or any of 8.1 to 8.38, wherein the method provides the compound of Formula 1J or 2J in admixture with at least 0.001% by weight and less than 1% by weight of at least one compound selected from the compound of Formula 1K or 2K, 1L or 2L, 1M or 2M, 1N or 2N, 1O or 2O, 1P or 2P, and 1Q or 2Q.

8.40 Method 8.39, wherein the method provides the compound of Formula 1J or 2J in admixture with at least 0.01% by weight and less than 0.5% by weight of at least one compound selected from the compound of Formula 1K or 2K, 1L or 2L, 1M or 2M, 1N or 2N, 1O or 2O, 1P or 2P, and 1Q or 2Q.

8.41 Method 8.39, wherein the method provides the compound of Formula 1J or 2J in admixture with at least 0.01% by weight and less than 0.5% by weight of at least two or at least three or at least four compounds selected from the compound of Formula 1K or 2K, 1L or 2L, 1M or 2M, 1N or 2N, 1O or 2O, 1P or 2P, and 1Q or 2Q.

8.42 Method 8.39, wherein the method provides the compound of Formula 1J in admixture with at least 0.001% by weight and less than 1% by weight of each of the compounds of Formula 1K, 1L, 1M, 1N, 1O, 1P, and 2Q, e.g., at least 0.01% and less than 0.5% by weight of each of said compounds.

8.43 Method 8.39, wherein the method provides the compound of Formula 2J in admixture with at least 0.001% by weight and less than 1% by weight of each of the compounds of Formula 2K, 2L, 2M, 2N, 2O, 2P, and 2Q, e.g., at least 0.0005% and less than 0.5% by weight of each of said compounds.

8.44 Method 8.39, wherein the method provides the compound of Formula 1J in admixture with about 0.01-0.80% by weight of the compound of Formula 1K, and/or about 0.005-0.40% by weight of the compound of Formula 1L, and/or about 0.005-0.30% by weight of the compound of Formula 1M, and/or about 0.01-0.60% by weight of the compound of Formula 1N, and/or about 0.005-0.40% by weight of the compound of Formula 1O, and/or about 0.005-0.45% by weight of the compound of Formula 1P, and/or about 0.0005-0.30% by weight of the compound of Formula 1Q.

8.45 Method 8.39, wherein the method provides the compound of Formula 2J in admixture with about 0.01-0.80% by weight of the compound of Formula 2K, and/or about 0.005-0.40% by weight of the compound of Formula 2L, and/or about 0.005-0.30% by weight of the compound of Formula 2M, and/or about 0.01-0.60% by weight of the compound of Formula 2N, and/or about 0.005-0.40% by weight of the compound of Formula 2O, and/or about 0.005-0.45% by weight of the compound of Formula 2P, and/or about 0.005-0.30% by weight of the compound of Formula 2Q.

8.46 Any of methods 8.39-8.45, wherein in the compound of Formula 1K or 2K, 1L or 2L, 1M or 2M, 1N or 2N, 1O or 2O, 1P or 2P, and 1Q or 2Q, the group R is methyl and the group Q is —(C=O)—.

8.47 Method 1K or 2K, or any of 8.1 et seq., wherein the method comprises the isolation and/or purification of the compound of Formula 1J or 2J in mono-tosylate salt form, e.g., in solid crystalline mono-tosylate salt form, and wherein the method further comprises combining the compound of Formula 1J or 2J with at least one molar equivalent of toluenesulfonic acid.

8.48 Method 8.47, wherein the solvent is water and/or an alcoholic solvent (e.g., methanol, ethanol, propanol, butanol) and/or a ketone solvent (e.g., acetone, 2-butanone, 2-pentanone, 3-pentanone, cyclohexanone, cyclopentanone) and/or an ether solvent (e.g., diethyl ether, diisopropyl ether, tetrahydrofuran, 1,4-dioxane, methyl tert-butyl ether), and/or a hydrocarbon solvent (e.g., hexane, pentane, cyclohexane, cyclopentane) or any combination thereof.

8.49 Method 8.47 or 8.48, wherein the mono-tosylate salt of the compound of Formula 1J or 2J is converted, in whole or in part, to a bis-tosylate salt of the compound of Formula 1J or 2J.

The compounds described herein and their pharmaceutically acceptable salts may be made using the methods as described and exemplified herein and by methods similar thereto and by methods known in the chemical art. In the description of the synthetic methods described herein, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. Therefore, at times, any reaction may be required to run at an elevated temperature or for a longer or shorter period of time than described herein. It is understood by one skilled in the art of organic synthesis that functionality present on various portions of the molecule must be compatible with the reagents and reactions proposed. If not commercially available, starting materials for these processes may be made by procedures which are selected from the chemical art using techniques similar or analogous to the synthesis of known compounds. All references cited herein are hereby incorporated by reference in their entirety.

Unless the terms are specifically defined for an embodiment, the terms used herein are generally defined as follows.

The phrase "pharmaceutically acceptable salts" refers to derivatives of the disclosed compounds wherein the parent compound is modified by making acid or base addition salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media such as ether, ethyl acetate, isopropyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418, the disclosure of which is hereby incorporated by reference. Compounds of the present disclosure, have more than one basic nitrogen atom. For example, compounds of Formula 1J and 2J each have three basic nitrogen atoms (two N-aryl piperazine nitrogens, and one aliphatic piperidine nitrogen). It is understood that the piperidine nitrogen is more basic than the two piperazine nitrogens. It is also understood that any one or two or all of these nitrogen atoms can form an acid addition salt with an acidic hydrogen of a monoprotic, diprotic or triprotic Bronsted acid, depending on the molar ratio of free base to acid provided in a reaction. As a result, when terms such as "acid addition salt" are used in this disclosure, such term refers to any such salts that are possible, as well as combinations thereof. For example, the term "tosylate salt form" of a compound of Formula 1J or 2J may refer to a mono-tosylate salt, di-tosylate salt, or tri-tosylate salt of said compound, or any mixture thereof. Similarly, the term "hydrochloride salt form" of a compound of Formula 1I or 2I may refer to a mono-hydrochloride salt, di-hydrochloride salt, or tri-hydrochloride salt of said compound, or any mixture thereof. The same is true of all other acid addition salt forms disclosed herein.

The term "alkyl" is intended to include both branched and straight-chain saturated aliphatic hydrocarbon groups having the specified number of carbon atoms; for example, "$C_1$-$C_4$ alkyl" denotes alkyl having 1 to 4 carbon atoms. Examples of alkyl include, but are not limited to, methyl, ethyl, n-propyl, isopropyl, n-butyl, isobutyl, sec-butyl, and tert-butyl.

"Halo", "halogen" or "halide" as used herein refers to fluoro, chloro, bromo, and iodo. Therefore, "alkyl halide" refers to a halogen group attached to an alkyl group as defined above, such as methyl iodide or iodobutane.

"Cycloalkyl" is intended to include monocyclic or polycyclic ring systems comprising at least one aliphatic ring. Therefore, "cycloalkyl" includes cyclopropyl, cyclobutyl, cyclopentyl, cyclopentenyl, cyclohexyl, cyclohexenyl and the like. Wherein cycloalkyl is a polycyclic system, such system may contain an aliphatic ring fused to an aromatic, non-aromatic, heteroaromatic or hetero nonaromatic rings. Examples of such include octahydro-1H-indene, 2,3-dihydro-1H-indene and 5,6,7,8-tetrahydroquinoline.

The term "heterocycloalkyl" herein refers to a monocyclic or polycyclic system comprising at least one aliphatic ring containing at least one heteroatom selected from a group consisting of O, N and S. Therefore, heterocycloalkyl may refer to piperidinyl, piperazinyl, 2-pyrrolidonyl, 1,2,3,4-tetrahydroquinolinyl, 2H,6H-1,5,2-dithiazinyl, 2H-pyrrolyl or 1,2,3,4-tetrahydro-1,8-naphthyridine.

As used herein, the term "aryl" is intended to mean a stable 5- to 7-membered monocyclic or polycyclic or 7- to 14-membered polycyclic ring system which comprises at least one aromatic ring (i.e., planar ring that contains 4n+2 Pi electrons, wherein n is an integer). Therefore, the term "aryl" includes phenyl, naphthyl and their derivatives. The term "aryl" is also intended to include polycyclic ring systems which contain at least one aromatic ring fused to one or more aromatic or non-aromatic or heteroaromatic rings (e.g., 2,3-dihydro-1H-indene).

As used herein, the term "heterocycle", "heterocyclic ring" or "heteroaryl" is intended to mean a stable 5- to 7-membered monocyclic or polycyclic or 7- to 14-membered polycyclic ring which comprises at least one aromatic ring containing at least one heteroatom independently selected from the group consisting of N, O and S. Therefore, a "heterocycle" or "heterocyclic ring" or "heteroaryl" may include a single heteroaromatic ring or a heteroaromatic ring fused to another heteroaromatic ring or to a non-heteroaromatic or non-aromatic ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of heterocycles or heteroaryl group include, but are not limited to 1H-indazole, thiazolyl, furyl, pyridyl, quinolinyl, pyrrolyl, indole or 5,6,7,8-tetrahydroquinoline.

The term "substituted," as used herein, means that any one or more hydrogens on the designated atom is replaced with a selection from the indicated group, provided that the designated atom's normal valency is not exceeded, and that the substitution results in a stable compound. Therefore, optionally substituted alkyl may refer to an alkyl group as defined above whereby one or more hydrogens are replaced with a selection from the indicated group including, but not limited to, halogen, hydroxy, amino, sulfhydryl, alkyl, alkenyl, alkynyl, haloalkyl (e.g. $CH_2C_1$, $CF_3$, $CH_3CH_2Br$, etc.), amido, aryl, arylalkyl, heteroaryl, heteroarylalkyl, cycloalkyl, heterocycloalkyl, alkoxy, carboxy, carbonyl, silyl, alkylamino, alkylamido, nitro, cyano, halo, —S(O)-alkyl, —S(O)$_2$-alkyl, R-cycloalkyl, R-heterocycloalkyl, R—C(O)—, R—C(O)—OR', R—O—, —N(R)(R') wherein R and R' are independently H, alkyl, aryl, heteroaryl, cycloalkyl, heterocycloalkyl, arylalkyl, heteroarylalkyl, heteroarylalkyl or heterocycloalkyl.

The term "resolution" is a term of art and refers to the separation of a racemic mixture into its enantiomers by any means, including reacting a chiral organic acid or base with the components of the racemic mixture to form diastereomeric salts and separating said salts by, for example, crystallization techniques. The term "chiral salt resolution" refers to the separation of a racemic mixture into its enantiomers through the use of a chiral acid.

The term "chromatography" is well known in the art and refers to a technique of separating the components of a mixture by interacting it with a stationary phase and eluting the components of the mixture with a mobile phase such as ethanol, methanol, acetonitrile, water or mixtures thereof. The term "chiral chromatography" refers to chromatography wherein the stationary phase is chiral.

The term "chiral acid" refers to any optically active acid capable of forming diastereomeric salts with compounds of Formula 1B or 2B. The terms "mono or di-carboxylic acid" or "sulfonic acid" herein refers to any compound that contains one or two carboxylic functional groups and a sulfonic acid group respectively. Examples of such acids include but are not limited to (+/−)/(R/S) tartaric acid, (+/−)/(R/S) (mono- or di-acetyl)tartaric acid, (+/−)/(R/S) (mono- or di-benzoyl)tartaric acid, (+/−)/(R/S) (mono- or di-pivaloyl)tartaric acid, (+/−)/(R/S) mandelic acid, (+/−)/(R/S) acetoxyphenyl acetic acid, (+/−)/(R/S) methoxyphenyl acetic acid, (+/−)/(R/S) hydroxymandelic acid, (+/−)/(R/S) halomandelic acid (e.g. 4-fluoromandelic acid), (+/−)/(R/S) lactic acid, and (+/−)/(R/S) camphor sulfonic acid.

The term "protecting agent" refers to any compound that reacts with the atom for which protection is desired so as to block or mask its functionality. It is typically used to temporarily modify a potentially reactive functional group so as to protect it from undesired chemical transformation. A desirable protecting agent is one which is compatible with or stable to the reaction condition and is easily cleaved off at a later point when protection is no longer desired.

The terms "protecting group" and "protective group" refer to removable chemical groups that are used to protect or mask reactive functional moieties during synthetic transformations. The term "protecting agent" refers to a reagent that is used to attach protecting a group to the functional moiety to be protected. For example, the protecting agent ethyl chloroformate is used to attach the protecting group ethoxycarbonyl, and the protecting agent BOC-anhydride is used to attach the protecting group t-butoxycarbonyl. Protecting groups, as defined herein, include groups with the general formula —P—Z, wherein Z is optionally substituted alkyl, aryl, alkylaryl, alkoxycarbonyl, or —OR wherein R is alkyl, aryl, arylalkyl or heteroarylalkyl, and wherein P is —CH$_2$—, —C(O)—, —C(O)O—, or S(O)$_2$. Examples of protecting groups include benzyloxycarbonyl (Cbz), triphenylmethyl, alkyloxy and aryloxy carbonyl (e.g., methoxycarbonyl, ethoxycarbonyl, t-butoxycarbonyl, phenoxycarbonyl), benzyl N-succinimidyl carbonyl, benzoyl, substituted benzoyl, substituted benzyloxycarbonyl, benzyl, substituted benzyl, and alkyl and aryl sulfonyl (e.g., methanesulfonyl, benzenesulfonyl, toluenesulfonyl). Further suitable protecting agents and protecting groups can be found, for example, in "Protective Groups in Organic Synthesis" by Theodora Green (publisher: John Wiley & Sons, Fourth Edition, 2007), the disclosure of which is hereby incorporated by reference in its entirety.

The term "deprotection" or "deprotect" or "deprotecting" refers to the act of removing or cleaving off a protecting group. The deprotection conditions for the above protecting groups necessarily vary with the choice of protecting group and may involve acid (e.g., hydrochloric, sulphuric, phosphoric or trifluoroacetic acid or a Lewis acid such as boron tris(trifluoroacetate)) or base (alkali metal hydroxide, e.g., lithium, potassium or sodium hydroxide) catalysis or catalytic hydrogenation condition (e.g., hydrogen and palladium-on-carbon).

The term "catalyst" herein refers to any substance or agent capable of affecting, inducing, increasing, influencing or promoting the reactivity of a compound or reaction without itself being consumed. The phrase "transition metal catalyst" refers to any metal having valence electrons in the d-orbitals, e.g. metals selected from one of Groups 3-12 of the periodic table. The catalysts useful for the methods of this invention include atoms, ions, salts or complexes of transition metals from Groups 8-11 of the Periodic Table. "Group 3-12 of the Periodic Table" refers to the groups of the Periodic Table as numbered according to the IUPAC system. Therefore, transition metals from Group 8-11 which include iron, ruthenium, osmium, cobalt, rhodium, iridium, nickel, palladium, platinum, copper, silver and gold. Examples of such catalysts include, but are not limited to CuI, CuCl, CuBr, CuBr$_2$, Cu(II) acetate, Cu$_2$Cl$_2$, Cu$_2$O, CuSO$_4$, Cu$_2$SO$_4$, Cu, Pd/C, PdCl$_2$, Pd(OAc)$_2$, (CH$_3$CN)$_2$PdCl$_2$, Pd[P(C$_6$H$_5$)$_3$]$_4$, bis(dibenzylideneacetone)palladium [Pd(dba)$_2$], tris(dibenzylideneacetone)dipalladium [Pd$_2$(dba)$_3$], Ni(acetylacetonate)$_2$, NiCl$_2$[P(C$_6$H$_5$)]$_2$ and Ni(1,5-cyclooctadiene)$_2$. Catalysts are typically, but not necessarily used in sub-stoichiometric amount relative to the reactants. Preferably, 0.5-20 mol %, most preferably, 10 mol % of the transition metal catalyst relative to the reactants is used.

The term "base" herein refers to organic or inorganic bases such as amine bases (e.g., ammonia, triethylamine, N,N'-diisopropylethylamine or 4-(dimethylamino)pyridine (DMAP); 1,5-diazabicycl[4.3.0]-non-5-ene (DBN), 1,5-diazabicyclo[5.4.0]undec-5-ene (DBU)); hydrides (e.g. sodium, lithium or potassium hydride); alkoxides, (e.g. sodium, potassium or lithium t-butoxide and K(OAr), Na(OAr)); or carbonates, bicarbonates, phosphates or hydroxides of an alkali or alkaline earth metal (e.g. sodium, magnesium, calcium, potassium, cesium or barium carbonate, bicarbonate, hydroxide or phosphate).

The term "Bronsted base" is art-recognized term and refers to an uncharged or charged atom or molecule, e.g., an oxide, amine, alkoxide, or carbonate, which is a proton acceptor. Examples of Bronsted base include, but are not limited to K₃PO₄, K₂CO₃, Na₂CO₃, Tl₂CO₃, Cs₂CO₃, K(OtBu), Li(OtBu), Na(OtBu), K(OPh), and Na(OPh), or mixtures thereof.

The term "Lewis base" is recognized in the art and refers to a chemical moiety capable of donating a pair of electrons under certain reaction conditions. Examples of Lewis bases include, but are not limited to, uncharged compounds such as alcohols, thiols, olefins, and amines (e.g., ammonia, triethylamine), and charged moieties such as alkoxides, thiolates, carbanions, and a variety of other organic anions.

The term "acid" herein refers to Lewis or Bronsted acid. Lewis acid is a term of art and refers to a chemical moiety capable of accept a pair of electrons (e.g., boron trifluoride). Bronsted acid refers to any chemical moiety capable of donating a proton (e.g., acetic acid, trifluoroacetic acid, methanesulfonic acid, hydrochloric acid, hydrobromic acid, sulfuric acid, phosphoric acid as well as other organic acids known in the art).

The term "ligand" refers to any atom, molecule or ion capable of donating or sharing one or more electrons through a coordinate and/or covalent bond with another central atom, typically a metal. "Monodentate ligand" refers to ligands that have one binding site to the central atom (e.g., pyridine or ammonia). "Bidentate ligand" refers to ligands that have two binding sites (e.g., N,N'-dimethylethylenediamine, N,N,N',N'-tetramethylethylenediamine or 1,10-phenathroline). Examples of useful ligands for group 8-11 transition metals include, but are not limited to, 2-phenylphenol, 2,6-dimethylphenol, 2-isopropylphenol, 1-naphthol, 8-hydroxyquinoline, 8-aminoquinoline, DBU, DBN, DABCO, 2-(dimethylamino)ethanol, N,N-diethylsalicylamide, 2-(dimethylamino)glycine, N,N,N',N'-tetramethyl-1,2-diaminoethane, 4,7-diphenyl-1,10-phenanthroline, 4,7-dimethyl-1,10-phenanthroline, 5-methyl-1,10-phenanthroline, 5-chloro-1,10-phenanthroline, 5-nitro-1,10-phenanthroline, 4-(dimethylamino)pyridine, 2-(aminomethyl)pyridine, (methylimino)diacetic acid, cis-1,2-diaminocyclohexane, trans-1,2-diaminocyclohexane, a mixture of cis- and trans-1,2-diaminocyclohexane, cis-N,N'-dimethyl-1,2-diaminocyclohexane, trans-N,N'-dimethyl-1,2-diaminocyclohexane, a mixture of cis- and trans-N,N'-dimethyl-1,2-diaminocyclohexane, cis-N-tolyl-1,2-diaminocyclohexane, trans-N-tolyl-1,2-diaminocyclohexane, a mixture of cis- and trans-N-tolyl-1,2-diaminocyclohexane, ethanolamine, 1,2-diaminoethane, N,N'-dimethyl-1,2-diaminoethane, N,N-dimethyl-2-hydroxybenzamide, N,N-diethyl-2-hydroxybenzamide, fluoro-N,N-diethyl-2-hydroxybenzamide, chloro-N,N'-diethyl-2-hydroxybenzamide, (2-hydroxyphenyl)(pyrrolidin-1-yl)methanone, biphenyl-2-ol, 2-pyridylphenol, 1,2-benezenediamine, ammonia, N,N-dimethylformamide, dimethylsulfoxide, 1-methyl-2-pyrrolidinone or mixtures thereof as well as the biphenyl and binaphthyl ligands hereinbefore described. In certain embodiments, the amount of ligand used may be a stoichiometric or an excess amount. In other embodiments, the ligand may be used as a solvent for the reaction. Therefore, reagents such as N,N-dimethylformamide, dimethylsulfoxide, 1-methyl-2-pyrrolidinone or other liquid amines may serve as a solvent as well as ligand for the reaction.

The term "N,N'-dimethylethylenediamine" is used interchangeably with "N,N'-dimethyl-1,2-diaminoethane".

The phrase "nucleophilic alkyl halide" refers to any compound having both an alkyl halide functional group (electrophilic) and a nucleophilic functional group. The term "nucleophilic" or "nucleophile" is well recognized in the art and refers to a chemical moiety having a reactive pair of electrons.

The term "reduction" or "reducing" refers to the conversion of a functional group in a molecule from a higher oxidation state to a lower oxidation state. The term "reducing agent" or "reductive agent" refers to any compound or complex that is known in the field for its effects in converting a functional group in a molecule from a higher oxidation state to a lower oxidation state. Examples of reduction include both the reduction of a carbon-carbon double bond to a carbon-carbon single bond, and reduction of a carbonyl group (C=O) to a methylene ($CH_2$). The reduction may be achieved via a direct electron, hydride or hydrogen-atom transfer. Typical reducing agents useful for Methods 1C and 2C include metal hydrides (e.g., lithium aluminum hydride, sodium borohydride, sodium cyanoborohydride) and hydrogen in the presence of a catalyst (e.g., Raney nickel, palladium on charcoal, nickel boride, platinum metal or its oxide, rhodium, ruthenium and zinc oxide, pentacyanocobaltate(II) $Co(CN)_5^{3-}$). Catalytic hydrogenation is typically carried out at room temperature and at atmospheric pressure, but higher temperature and/or higher pressure may be required for more resistant double bonds. Other reducing agents useful for converting double bonds to single bonds include silane and acid; sodium cyanoborohydride and acid; zinc and acid; sodium and liquid ammonia; sodium in ethanol; and borane-triethylamine. Typical reducing agents useful for reducing a carbonyl to a methylene as in Methods 1H and 2H include but are not limited to metal hydrides (e.g., diisobutyl aluminum hydride (DIBAL), sodium bis(2-methoxyethoxy) aluminum hydride (Red-Al) or sodium cyanoborohydride); boranes (e.g., $BH_3$-THF); or organoboranes (e.g. bis(benzyloxy)borane). Alternatively, such conversion may also be accomplished through catalytic hydrogenation by using hydrogen in presence of a catalyst (e.g. nickel, palladium on charcoal, nickel boride, platinum metal, platinum oxide, palladium oxide, rhodium oxide, ruthenium oxide or zinc oxide); Wolff-Kishner reduction by heating the ketone with hydrazine hydrate in the presence of a base such as sodium or potassium hydroxide (See Todd, Org. React. 4, 378-422 (1948)); or Clemmensen reduction by heating the ketone with zinc amalgam and aqueous mineral acid such as hydrochloric acid (See Vedejs, Org. React. 22, 401-422 (1975)). Other reagents that may also accomplish such reduction include triisopropyl phosphate, copper in the presence of sulfuric acid and tin in the presence of hydrochloric acid. For further examples of reducing agents, see "Advanced Organic Chemistry: Reactions, Mechanisms, and Structure" by Jerry March, p. 771-790, John Wiley & Sons, Inc. (Fourth Edition).

The term "alkylation" refers to the introduction of an alkyl radical onto an organic compound by substitution or addition. Therefore, the term "N-alkylation" refers to the introduction of an alkyl radical onto the nitrogen atom of the organic compound.

Procedures for the production of compounds described herein and for the carrying out of some of the steps of the methods described herein are known to those skilled in the art, and can be found, for example, in U.S. Pat. Nos. 8,309,722; 8,779,139; 9,315,504; 9,751,883; 8,648,077; 9,199,995; and 9,586,960; the contents of each of which are hereby incorporated by reference in their entireties.

EXAMPLES

Example 1: 6-bromo-2,3,4,5-tetrahydro-1H-pyrido[4,3-b]indole hydrochloric Acid Salt

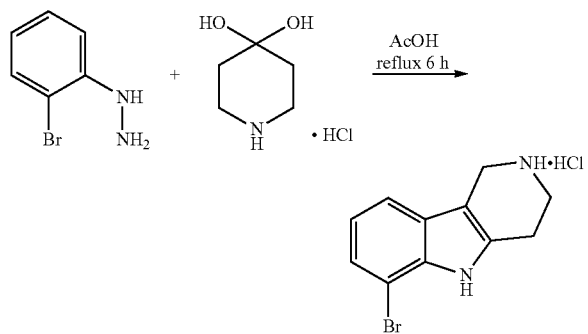

1-(2-bromophenyl)hydrazine hydrochloride and 4-piperidinone monohydrate hydrochloride are combined in about 1:1.1 molar ratio, in acetic acid, and the resulting slurry is heated to reflux until less than 1% of the hydrazine starting material remains by HPLC analysis (e.g., for 6 hours). The reaction mixture is then cooled to room temperature, filtered, and the cake is washed with acetone and dried to a solid which is used in the next step.

Example 2: [4aS, 9bR]-6-bromo-2,3,4,4a,5,9b-hexahydro-1H-pyrido[4,3-b]indole

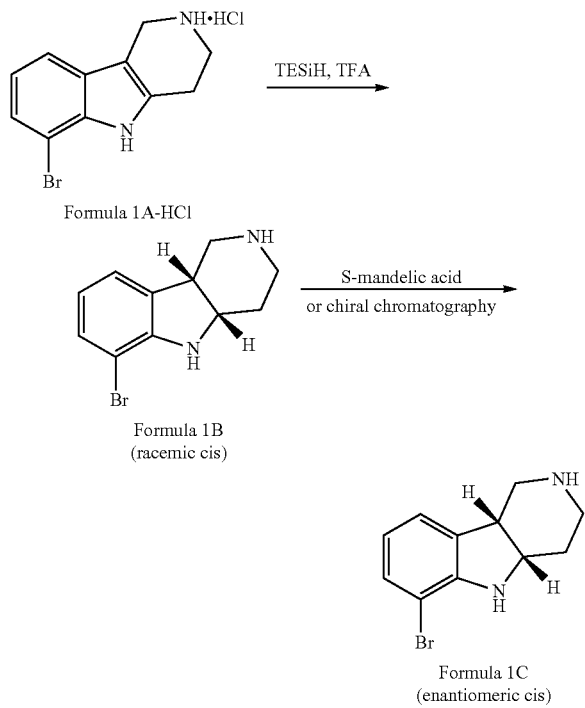

Reduction (Option 1):

[4aS, 9bR]-6-bromo-2,3,4,4a,5,9b-hexahydro-1H-pyrido[4,3-b]indole may be prepared by mixing 6-bromo-2,3,4,5-tetrahydro-1H-pyrido[4,3-b]indole hydrochloric acid salt with trifluoroacetic acid (630 ml, 8.48 mmol, 10 volumes) and triethylsilane (172 ml). The mixture is stirred at room temperature under nitrogen for 19 hours. Excess trifluoroacetic acid and triethylsilane are removed in vacuo. Hexanes (550 ml) are added to the remaining oil and stirred at room temperature for 1 hour; the hexanes are decanted. An additional 250 ml of hexanes are added, stirred for 1 hour and decanted. 2N aqueous sodium hydroxide is added to the remaining oil until the pH is 10 and then the solution is extracted with dichloromethane. The organic layers are combined and washed with brine and dried ($Na_2SO_4$).

Reduction (Option 2):

In an alternative method, to a 3 L 3-neck RBF with magnetic stirrer, $N_2$ inlet and drying tube is charged methanesulfonic acid (400 mL). 6-bromo-2,3,4,5-tetrahydro-1H-pyrido[4,3-b]indole hydrochloric acid salt (100 g) is charged in portions. The reaction mixture is heated to 40° C. to 45° C., and then triethylsilane (TES) (55.5 mL, 1 eq.) is charged drop wise over 1 hour in order to control exotherm. The temperature is kept at 40° C. to 45° C. Once the addition is complete, the mixture is stirred at 40° C. to 45° C. for 1.5 h. Additional TES (13.9 mL, 0.25 eq.) may be added over approximately 10 minutes, after which, the mixture is stirred at 40° C. to 45° C. for 30 min. Additional TES (13.9 mL, 0.25 eq.) may be added over approximately 10 minutes, after which the mixture is stirred at room temperature overnight. Additional TES (5.5 mL, 0.1 eq.) may be charged and the mixture stirred at room temperature for 90 min. After cooling to <10° C., the reaction is quenched with water (600 mL) by adding water drop wise at a rate to maintain <40° C. (strong exotherm observed). Dichloromethane (1000 mL) is added and the mixture is adjusted to about pH=12 with 50% w/v aqueous NaOH. The mixture is filtered through a layer of Celite. The layers are separated and the aqueous layer is extracted with dichloromethane (100 mL). The combined organic layer is washed with water (100 mL), dried over magnesium sulfate (120 g), filtered and concentrated under vacuum. The residue is treated with heptanes. After filtration, the obtained solid is dried under vacuum at 30° C. to give 73.1 g of product (yield: 83%, HPLC purity: 97.1%).

Separation (Option 1):

Enantiomeric separation of [4aS, 9bR]-6-bromo-2,3,4,4a,5,9b-hexahydro-1H-pyrido[4,3-b]indole may be carried out by dissolving the racemic cis 6-bromo-2,3,4,4a,5,9b-hexahydro-1H-pyrido[4,3-b]indole (8 g, 31.6 mmol) in methanol (160 mL) at 50° C. (oil bath) and adding (R)-(−)-Mandelic acid (4.8 g, 31.6 mmol) in portions. The resulting clear solution is stirred at 50° C. for several minutes and then ether (80 mL) is added dropwise. The resulting solution is cooled to room temperature and the white precipitate (R-Mandelate salt, 3.7 g) is filtered off. HPLC analysis shows >99% e.e. The filtrate is concentrated, treated with 1N sodium hydroxide (100 mL) and is extracted twice with dichloromethane (2×50 mL). The dichloromethane layers are combined, washed with brine (2×200 mL) and dried with sodium sulfate. The dichloromethane solution is concentrated to an oil (5.59 g) and is redissolved in methanol (90 mL) at 50° C. (S)-(+)-Mandelic acid (3.53 g, 23.2 mmol) is added in portions. The resulting clear solution is stirred at 50° C. for several minutes and ether (45 mL) is added dropwise. The resulting solution is cooled to room temperature and the white precipitate (S-Mandelate salt, 4.19 g) is filtered off. HPLC analysis shows >99% e.e. R-Mandelate: $[\alpha]_D^{25}$=−98.1, S-Mandelate: $[\alpha]_D^{25}$=+102, solvent:DMSO. Alternatively, the resolution may be carried out in a mixture of methanol and t-butyl methyl ether (MTBE), or alternatively, in ethanol.

Separation (Option 2):

Alternatively, [4aS, 9bR]-6-bromo-2,3,4,4a,5,9b-hexahydro-1H-pyrido[4,3-b]indole may be separated by dissolving the racemic cis 6-bromo-2,3,4,4a,5,9b-hexahydro-1H-pyrido[4,3-b]indole (9.61 g, 38.0 mmol) in methanol (190 mL) at 50° C. and adding (S)-(+)-Mandelic acid (5.78 g, 38.0 mmol) in portions. The resulting clear solution is stirred at 50° C. for several minutes and ether (95 mL) is added dropwise. The resulting solution is cooled to room temperature. The white precipitate (S-Mandelate salt, 4.1 g) is filtered off. HPLC analysis shows >99% e.e.

In a variation of the preceding method, [4aS, 9bR]-6-bromo-2,3,4,4a,5,9b-hexahydro-1H-pyrido[4,3-b]indole may be separated by dissolving the racemic cis 6-bromo-2,3,4,4a,5,9b-hexahydro-1H-pyrido[4,3-b]indole in a solution of 2 wt % water in ethanol at 45° C., and this mixture is then heated to reflux, resulting in a clear solution. (S)-(+)-Mandelic acid (0.5-0.58 equivalents) in 2 wt %  water/ethanol is added slowly to the starting material solution at a rate to maintain a temperature between 65 and 80° C. After refluxing for an additional one hour, the mixture is cooled to 70° C. and optionally seeded with pure [4aS, 9bR]-6-bromo-2,3,4,4a,5,9b-hexahydro-1H-pyrido[4,3-b]indole to stimulate crystallization. The reaction becomes a slurry as it cools further to about 20° C. over 2-3 hours. The product cake is finally isolated by filtration and washed with ethanol, followed by drying under vacuum at 35 to 50° C.

Separation (Option 3):

Enantiomeric separation of [4aS, 9bR]-6-bromo-2,3,4,4a,5,9b-hexahydro-1H-pyrido[4,3-b]indole may also be carried out by dissolving the racemic cis 6-bromo-2,3,4,4a,5,9b-hexahydro-1H-pyrido[4,3-b]indole (1710 g "as is," 1570 g by theory, 6.21 mol) in methanol (24 l) by warming to 40-50° C. (under nitrogen). To the mixture is added (R)-(−)-Mandelic acid (944 g, 6.2 mol) in one portion. The power to the heating mantle is turned-off and MTBE (13L) is charged to the mixture. The resulting solution is allowed to cool to room temperature with stirring and aged for 30-40 hours at 15-25° C. with stirring. The product is isolated by filtration as a white to off-white precipitate and allowed to air dry at ambient temperature overnight. This affords 580 gm (23%) of the R-Mandelate salt. Chiral HPLC analysis shows >99% e.e.

The filtrate is concentrated, diluted with water (25 L), stirred and treated with 50% NaOH (800 ml) to a pH of ~14 as measured by pH paper. The free base is extracted with dichloromethane (2×17L and 1×6L). The DCM layers are combined, dried (Na$_2$SO$_4$) and concentrated to afford a solid free base (~1150 g). The free base is dissolved in methanol (17 L) by warming to 40-50° C. under N$_2$ and (S)-(+)-Mandelic acid (692 g, 4.55 mol) is added. The heating mantle is turned off and to the solution is added MTBE (8.5 L) in one portion. The resulting solution is allowed to cool to room temperature with stirring and aged for 30-40 hours. The product is isolated by filtration as a white to off-white precipitate and air dried at ambient temperature overnight. This afforded 828 gm (33%) of S-Mandelate salt. Chiral HPLC analysis showed the faster moving enantiomer is present (>99% ee) with two other impurities present at ~1% each (which elute just before the undesired enantiomer). R-Mandelate: $[\alpha]_D^{25}=-98.1$, S-Mandelate: $[\alpha]_D^{25}=+102$, solvent:DMSO (about 10 mg in 3 ml DMSO). Chiral HPLC conditions: ChiralPak AD-H, 250×4.6 mm, 30% IPA in hexanes containing 0.1% diethylamine, flow 0.8 ml/min, UV detection at 254 nm. Samples are prepared by sonicating the salt in IPA.

Separation (Option 4):

Alternative to chiral resolution, enantiomeric separation of [4aS, 9bR]-6-bromo-2,3,4,4a,5,9b-hexahydro-1H-pyrido[4,3-b]indole may also be achieved by preparative chromatography using CHIRALPAK® AD® column, 20 μm, 5 cm id×50 cm L. 26.4 g, 23.0 g and 14.8 g of racemic 6-bromo-2,3,4,4a,5,9b-hexahydro-1H-pyrido[4,3-b]indole are dissolved separately in 100% ethanol with stirring (optionally with low heating) and then filtered through a 0.4 μm filter. The feeds are injected separately at 25 mL volume and eluted with 100% Ethanol at a flow rate of 150 mL/min at 25° C. Alternatively, 420 g of racemic 6-bromo-2,3,4,4a,5,9b-hexahydro-1H-pyrido[4,3-b]indole is similarly dissolved, filtered and injected at 55 mL volume onto a CHIRALPAK® AD® column, 20 μm, 11 cm ID×25 cm L with a flow rate of 400 mL/min. The products are detected at an ultraviolet wavelength of 330 nm. The products are collected and the solvents are evaporated on rotary evaporators at 40° C. and under a vacuum of 50-70 mbar. The products are analysed through chiral HPLC analysis by using an AD-H 4.6 mm ID×250 mm column at 30° C. column temperature, 100% ethanol mobile phase at a flow rate of 0.7 mL/min and detected at 200 nm, 230 nm, 250 nm, 280 nm or 325 nm. The products are also analysed by achiral HPLC analysis using an Eclipse, 5 μm XDB-C8, 4.6 mm ID×250 mm column at 30° C. column temperature, 75:25 methanol/0.1% aqueous diethylamine at a flow rate of 1 mL/min and detected at 250 nm, 200 nm, 230 nm, 280 nm or 325 nm. The isolated product is >98% e.e.

Example 3: (4aS,9bR)-ethyl 6-bromo-3,4,4a,5-tetrahydro-1H-pyrido[4,3-b]indole-2(9bH)-carboxylate

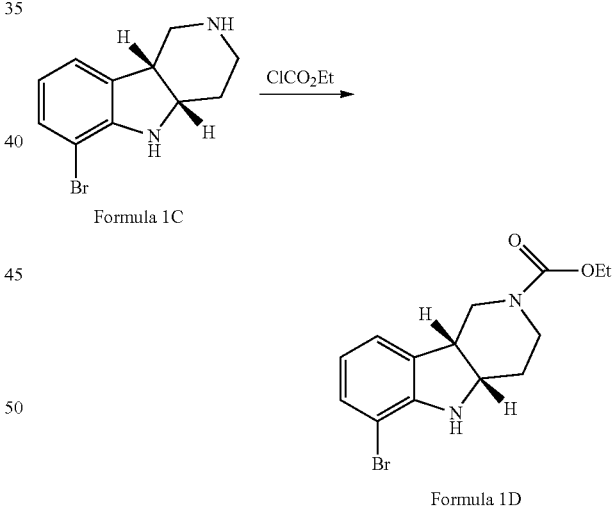

(4aS,9bR)-ethyl 6-bromo-3,4,4a,5-tetrahydro-1H-pyrido[4,3-b]indole-2(9bH)-carboxylate may be prepared by first obtaining [4aS, 9bR]-6-bromo-2,3,4,4a,5,9b-hexahydro-1H-pyrido[4,3-b]indole (36.0 g, 0.142 mol)) as a free base by using 50% aqueous sodium hydroxide solution and extracting the product into MTBE. The conversion to (4aS, 9bR)-ethyl 6-bromo-3,4,4a,5-tetrahydro-1H-pyrido[4,3-b]indole-2(9bH)-carboxylate may then be done by cooling a suspension of [4aS, 9bR]-6-bromo-2,3,4,4a,5,9b-hexahydro-1H-pyrido[4,3-b]indole (36.0 g, 0.142 mol)) in THF (300 ml) and triethylamine (24 ml) in an ice-water bath. Ethyl chloroformate is added dropwise (13.5 ml, 0.142 mol)

via a syringe pump over 1 hour. The ice-water bath is removed and the reaction mixture is stirred at room temperature for another hour. The reaction mixture is passed through a pad of Celite and the solvent is evaporated to give (4aS,9bR)-ethyl 6-bromo-3,4,4a,5-tetrahydro-1H-pyrido[4,3-b]indole-2(9bH)-carboxylate). $^1$H NMR (CDCl$_3$, 300 MHz): 1.20-1.35 (m, 3H), 1.73-1.85 (m, 1H), 1.85-1.99 (m, 1H), 3.22-3.52 (m, 3H), 3.52-3.66 (m, 1H), 3.66-3.95 (Br, 1H), 3.95-4.21 (m, 4H), 6.60 (t, J=7.7 Hz, 1H), 7.04 (d, J=7.2 Hz, 1H), 7.20 (d, J=8.1 Hz, 1H).

Alternative to the use of [4aS, 9bR]-6-bromo-2,3,4,4a,5,9b-hexahydro-1H-pyrido[4,3-b]indole (Compound of Formula 1C) free base, the reaction may also be carried out by starting with the (S)-mandelate salt of [4aS, 9bR]-6-bromo-2,3,4,4a,5,9b-hexahydro-1H-pyrido[4,3-b]indole. A 100 mL round-bottomed flask is equipped with a magnetic stirring bar, a pressure-equalizing addition funnel, and a N$_2$ inlet on top of the addition funnel. The flask is charged with the S-mandelate starting material (5 g, 12.35 mmol), Na$_2$CO$_3$ (2.88 g, 27.17 mmol), and 25 mL of THF. To the yellow reaction mixture at 25° C. (heating block temperature) is added a solution of ethyl chloroformate (1.64 g, 15.11 mmol) in 5 mL of THF dropwise over ca 70 minutes. The batch is stirred at 25° C. for another 10 min, and then is checked by HPLC. Less than 2% of the starting material is observed by HPLC, and the desired product is registered at ca. 98%. To the batch is added 12.5 mL of EtOH, and the batch is concentrated under reduced pressure to remove about 30 mL of solvent (mostly THF). To the batch is then added 37.5 mL of H$_2$O, and the resultant mixture shows pH>9 by pH paper. The yellow mixture is then stirred at room temperature for about 1 h, and then is filtered. The solid is rinsed with 25 mL of H$_2$O. After drying in a vacuum oven at 58° C. for about 16 h, 3.9442 g of a yellow solid is obtained (98% yield). $^1$H NMR of the solid conformed and showed no (s)-mandelic acid. HPLC analysis of the product shows the desired product at >99% purity. LC-MS showed a peak with M/e=326 (M+1).

Example 4: [4aS,9bR]-ethyl 5-(2-amino-2-oxoethyl)-6-bromo-3,4,4a,5-tetrahydro-1H-pyrido[4,3-b]indole-2(9bH)-carboxylate

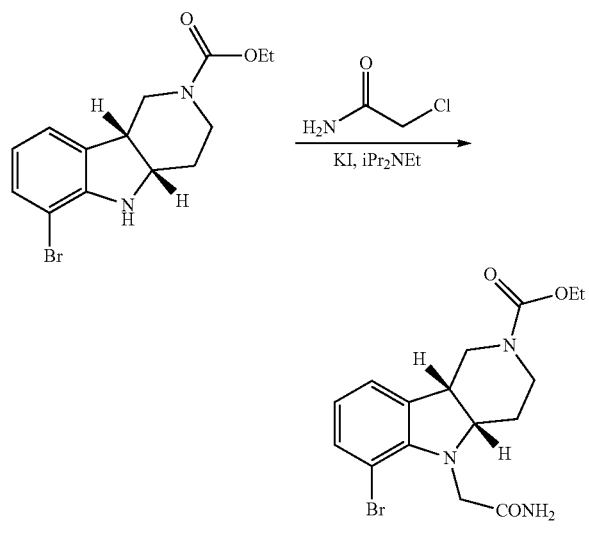

(4aS,9bR)-ethyl 5-(2-amino-2-oxoethyl)-6-bromo-3,4,4a,5-tetrahydro-1H-pyrido[4,3-b]indole-2(9bH)-carboxylate may be prepared by heating to a reflux a suspension of (4aS,9bR)-ethyl 6-bromo-3,4,4a,5-tetrahydro-1H-pyrido[4,3-b]indole-2(9bH)-carboxylate (5.648 g, 17.4 mmol), 2-chloroacetamide (7.32 g, 78.2 mmol), potassium iodide (19.2 g, 77.7 mol) and diisopropylethylamine (19 mL, 115 mmol) in acetonitrile (80 mL) for 27 hours. The solvent is removed in a vacuo and water (200 mL) is added to the residue and stirred for 1 hour. The resulting white solid is filtered off, washed with ethanol and dried.

Example 5: (4aS,9bR)-ethyl 6-bromo-5-(2-(methylamino)-2-oxoethyl)-1,3,4,4a,5,9b-hexahydro-2H-pyrido[4,3-b]indole-2-carboxylate

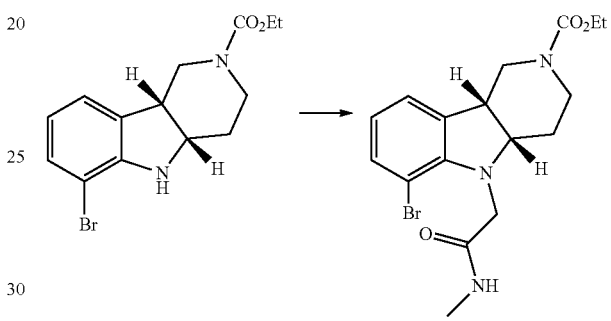

1.000 equivalents of ethyl (4aS,9bR)-6-bromo-1,3,4,4a,5,9b-hexahydro-2H-pyrido[4,3-b]indole-2-carboxylate is charged into a reactor with 0.50 volumes of dimethylacetamide solvent at 20° C. A solution of 1.500 equivalents of N-methyl chloroacetamide in 0.30 volumes of dimethylacetamide is added, followed by 1.000 equivalents of potassium iodide, and 1.700 equivalents of diisopropylethylamine. The resulting suspension is heated at 102° C. for 15 to 18 hours. After cooling to 45° C., 5.00 volumes of water are added. After further cooling and agitation, the product is isolated as a solid filter cake and is washed with additional water and dried under vacuum.

Example 6: (6bR,10aS)-ethyl 2,3,6b,9,10,10a-hexahydro-2-oxo-1H-pyrido[3',4':4,5]-pyrrolo[1,2,3-de]quinoxaline-8-carboxylate

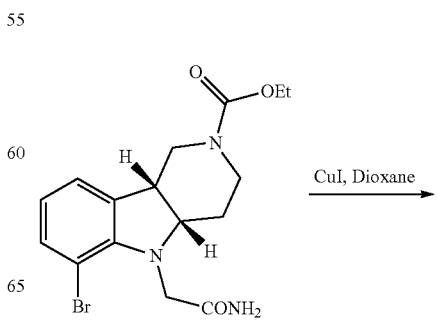

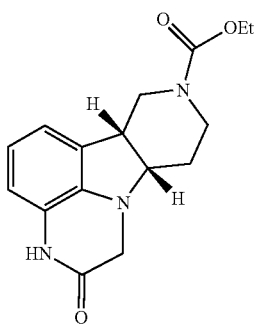

A suspension of [4aS,9bR]-ethyl 5-(2-amino-2-oxoethyl)-6-bromo-3,4,4a,5-tetrahydro-1H-pyrido[4,3-b]indole-2(9bH)-carboxylate (254 mg, 1.34 mmol), cuprous iodide (254 mg, 1.34 mol), potassium carbonate (3.96 g, 28.7 mmol) and N,N'-dimethyl ethylenediamine (0.31 mL, 2.87 mmol) in dioxane (20 mL) is heated at reflux for 4.5 hours. Another portion of cuprous iodide (250 mg, 1.32 mmol) and N,N'-dimethyl ethylenediamine (0.33 mL, 3.05 mmol) is added. The resulting mixture is heated to a reflux for another 3 hours and then at 73° C. for about 66 hours. The reaction mixture is concentrated and passed through a short alumina column using 100:3:3 dichloromethane:triethylamine:methanol. The resulting solvent from the column is evaporated to a solid and redissolved in dichloromethane. The dichloromethane solution is washed with brine, dried with sodium sulfate and concentrated to a solid (3.7 g, 95%, 83% pure by HPLC).

Example 7: (6bR,10aS)-ethyl 2,3,6b,9,10,10a-hexahydro-3-methyl-2-oxo-1H-pyrido[3',4':4,5]-pyrrolo[1,2,3-de]quinoxaline-8-carboxylate

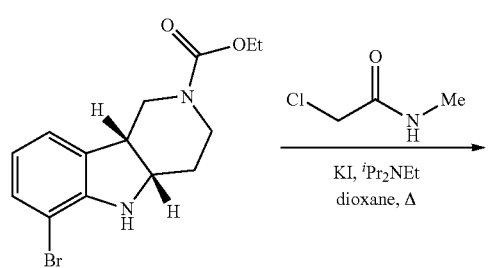

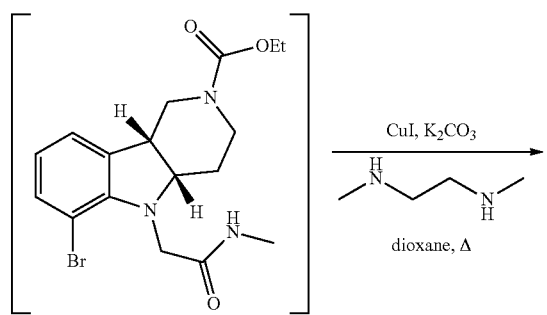

(6bR,10aS)-ethyl 3,6b,9,10,10a-hexahydro-3-methyl-2-oxo-1H-pyrido[3',4':4,5]-pyrrolo[1,2,3-de]quinoxaline-8-carboxylate may also be made in a one pot method starting from Compound of Formula 1D. A 2 liter 4-neck round bottom flask is equipped with a mechanical stirrer, reflux condenser, $N_2$ inlet, Teflon covered K-type temperature probe with a controller, and a heating mantle. To the flask is charged (4aS,9bR)-ethyl 6-bromo-3,4,4a,5-tetrahydro-1H-pyrido[4,3-b]indole-2(9bH)-carboxylate (250 g, 769 mmol), N-methyl chloroacetamide (124 g, 1153 mmol, 1.5 eq.), potassium iodide (191.5 g, 1160 mmol, 1.5 equiv.), diisopropylethylamine (266 mL, 1531 mmol, 2.0 eq.), and dioxane (625 mL). The reaction is heated to reflux temperature of about 103° C. until less than 3% of the starting substrate is observed by HPLC (about 48 hours). Additional charge of N-methyl chloroacetamide and diisopropylethylamine may be necessary. The reaction is then cooled to ca. 80° C., and at this temperature copper iodide (29.2 g, 153.8 mmol, 0.2 eq.), potassium carbonate (232.5 g, 1682 mmol, 2.2 eq.), dimethylethylene diamine (49.6 mL, 461 mmol, 0.6 eq.), and additional dioxane (375 mL) is added. The reaction is then re-heated to reflux and is monitored by HPLC. Reflux occurs at ca. 103° C. The reaction is monitored by HPLC.

When complete, the reaction is cooled to ca. 40° C. and poured onto a plug of flash-grade silica gel (625 g, 2.5 g/g). It is eluted (under vacuum) with 6.25 L of ethyl acetate. The eluent is concentrated to a solid residue (320 gm), and then is dissolved in hot ethanol (800 ml). This mixture is allowed to cool to ambient temperature and stirred overnight. The next day it is cooled to 0-5° C., aged for 1 h and filtered. The cake is washed with cold ethanol (150 ml) and allowed to air dry to afford 170 grams (70%) of product as a white solid which is >99A % pure by HPLC. HPLC 10:90 to 90:10 $CH_3CN:H_2O$ over 15 min. Hold at 90:10 for 2 min, 0.025% TFA Buffer, 1.5 mL/min, UV at 220 nm, Phenomenex Jupiter C18 column 4.6 mm×250 mm. The product is 75A % pure by LC/MS in the total ion chromatogram. $^1$H-NMR (300 MHz, CDCl$_3$) 1.28 (t, J=6.9 Hz, 3H), 1.86-1.96 (m, 2H), 2.72 (br, 1H), 3.09-3.48 (m, 7H), 3.86-4.21 (m, 5H), 6.75 (dd, J=1.2, 7.8 Hz, 1H), 6.82 (t, J=7.8 Hz, 1H), 6.90 (dd, J=1.2, 7.2 Hz, 1H).

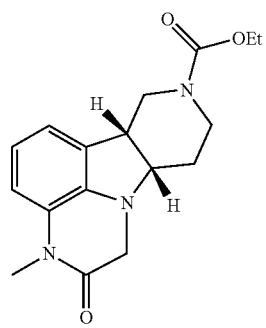

Example 8: (6bR,10aS)-3-methyl-2,3,6b,9,10,10a-hexahydro-1H-pyrido-[3',4':4,5]-pyrrolo[1,2,3-de]quinoxaline-8-carboxylate

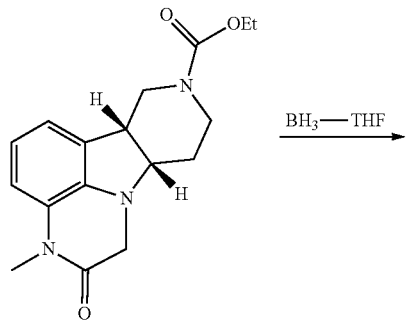

(6bR,10aS)-ethyl 2,3,6b,9,10,10a-hexahydro-3-methyl-1H-pyrido-[3',4':4,5]-pyrrolo[1,2,3-de]quinoxaline-8-carboxylate may be prepared by adding BH$_3$.THF (1M in THF, 143 mL, 143 mmol) dropwise at room temperature over 15 minutes to a suspension of (6bR,10aS)-ethyl 2,3,6b,9,10,10a-hexahydro-3-methyl-2-oxo-1H-pyrido[3',4':4,5]-pyrrolo[1,2,3-de]quinoxaline-8-carboxylate (18.0 g, ca.57 mmol) in 50 ml of THF. The resulting mixture is heated to a reflux for 3 hours. The reaction mixture is cooled in an ice-water bath and 150 ml of 6N HCl is added dropwise. After THF is removed in vacuo, 2N NaOH is added until pH=9 followed by extraction with 500 ml of DCM. The DCM layer is washed with brine and dried over Na$_2$SO$_4$. Evaporation of the solvent yields crude (6bR,10aS)-ethyl 2,3,6b,9,10,10a-hexahydro-3-methyl-1H-pyrido-[3',4':4,5]-pyrrolo[1,2,3-de]-quinoxaline-8-carboxylate.

Alternatively, (6bR,10aS)-3-methyl-2,3,6b,9,10,10a-hexahydro-1H-pyrido-[3',4':4,5]-pyrrolo [1,2,3-de]quinoxaline may be prepared as follows: To a 5 L, 3-necked round-bottomed flask equipped with an overhead stirrer, an N$_2$ inlet, and a K-type Teflon covered temperature probe is charged with (6bR,10aS)-ethyl 2,3,6b,9,10,10a-hexahydro-3-methyl-2-oxo-1H-pyrido[3',4':4,5]-pyrrolo[1,2,3-de]quinoxaline-8-carboxylate (218 g, 691.3 mmol) using THF (ca. 50 mL). The reaction vessel is vacuum/N$_2$ purged three times, and then is added a 1 M solution of BH$_3$-THF complex in THF (1962 mL, 1962 mmol, 2.8 eq.) slowly through an addition funnel. The resultant clear solution is then heated at 60° C. The resultant batch is then stirred at 60° C. for ca. 17 h and showed 89.0% of the desired product with ca. 3.0% of unreacted substrate by HPLC. The batch is stirred at 60° C. for another 3 h, and then is cooled in an ice bath to ca. 10° C. To the batch is added MeOH (327 mL, 8073 mmol, 11.7 eq.) slowly through an addition funnel while keeping the internal temperature below 25° C. The resultant batch is stirred in the ice bath for ca. 30 min, and then is concentrated in vacuo to afford a yellow paste. The crude paste is then partitioned between EtOAc (2180 mL) and H$_2$O (2180 mL). The separated organic layer is dried (Na$_2$SO$_4$), filtered, and concentrated under reduced pressure to afford 227.6 g of a yellow liquid. HPLC analysis of the liquid showed 89% of the desired product with 2.6% of an impurity at RRt 0.62 and 2.5% of the starting material. $^1$H NMR (CDCl$_3$, 300 MHz) δ 1.28 (t, J=7.0 Hz, 3H), 1.79-1.95 (m, 2H), 2.74-2.92 (m, 5H), 3.02-3.22 (m, 2H), 3.22-3.38 (m, 3H), 3.54-3.64 (m, 1H), 3.78-4.24 (m, 4H), 6.41 (d, J=7.8 Hz, 1H), 6.54 (d, J=7.2 Hz, 1H), 6.66 (t, J=7.7 Hz, 1H); $^{13}$C—NMR (CDCl$_3$, 75 MHz) δ 14.9, 24.7, 37.7, 39.9, 41.4, 44.4, 45.8, 50.7, 61.4, 65.0, 109.3, 113.3, 120.6, 128.8, 135.1, 138.2, 155.6.

Example 9: (6bR,10aS)-3-methyl-2,3,6b,7,8,9,10,10a-octahydro-1H-pyrido-[3',4':4,5]-pyrrolo[1,2,3-de]quinoxaline

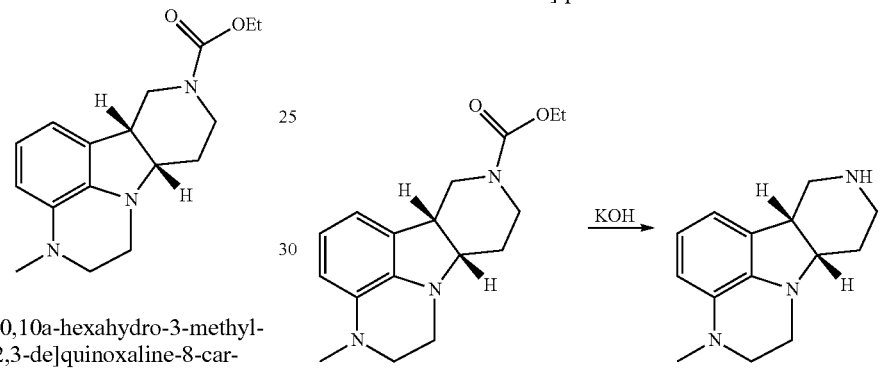

Ethyl (6bR,10aS)-3-methyl-2,3,6b,9,10,10a-hexahydro-1H-pyrido-[3',4':4,5]-pyrrolo[1,2,3-de]quinoxaline-8-carboxylate (ca. 18.5 g, 57 mmol), KOH (12.7 g, 226 mmol) and n-butanol are placed in a 300 ml pressure bottle and heated in an oil bath at 120° C. for 3 hours. n-butanol is removed in vacuo and 300 ml of water is added and then extracted with DCM. The DCM layers are combined and washed with brine and dried (Na$_2$SO$_4$). Evaporation of the solvent gives (6bR,10aS)-3-methyl-2,3,6b,7,8,9,10,10a-octahydro-1H-pyrido-[3',4':4,5]-pyrrolo[1,2,3-de]quinoxaline.

Example 10: (6bR,10aS)-3-methyl-2,3,6b,7,8,9,10,10a-octahydro-1H-pyrido[3',4':4,5]pyrrolo[1,2,3-de]quinoxaline hydrochloride

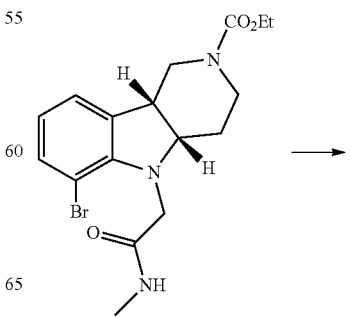

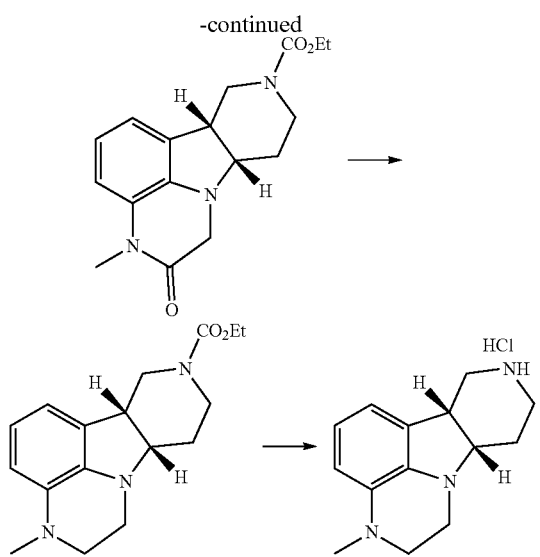

This Example presents a one-pot three-step conversion, which includes the cyclization of a Compound of Formula 1E to yield a Compound of Formula 1F, the reduction of the amide of the Compound of Formula 1F to yield a Compound of Formula 1H, and the deprotection of the Compound of Formula 1H to yield a Compound of Formula 1I, wherein in each of said Formulas R is methyl, and wherein B is ethoxycarbonyl.

1.00 equivalents of ethyl (4aS,9bR)-6-bromo-5-(2-(methylamino)-2-oxoethyl)-1,3,4,4a,5,9b-hexahydro-2H-pyrido[4,3-b]indole-2-carboxylate is charged into a reactor with 1.90 volumes of toluene, followed by the addition of 2.20 equivalents of potassium carbonate. The batch is distilled at 110° C. with an azeotropic separator until the distillate is clear. The temperature is adjusted to 50° C., and then 0.20 equivalents of copper (I) iodide and 0.25 equivalents of DBU are added. The reaction is heated and agitated for 3-4 hours at 95° C. When the alkylation reaction is completed, as judged by HPLC, the temperature is adjusted to 35° C. and 3.00 equivalents of 1.0M borane-THF complex in THF is added. The reaction is stirred for 3-4 hour at 10° C. to 40° C. When the reduction reaction is completed, as judged by HPLC, the reaction is cooled to 5° C. and then the excess reagent is quenched by the slow addition of 1.0 volume of methanol. The reaction is stirred for an additional hour, and then it is filtered through celite and washed with THF. Solvent is removed by distillation, and the intermediate product, ethyl (6bR,10aS)-3-methyl-2,3,6b,9,10,10a-hexahydro-1H-pyrido[3',4':4,5]pyrrolo[1,2,3-de]quinoxaline-8(7H)-carboxylate, is isolated by aqueous extraction between 5% sodium hydroxide solution and ethyl acetate. The organic phases are combined and washed with brine, and then filtered through Florisil. 20-33% aqueous hydrochloric acid is added to reduce the pH to 1 or below, and the biphasic mixture is vigorously stirred for 15 minutes. The layers are separated, the organic layer is discarded, and the aqueous layer is distilled under vacuum to remove solvent. 33% aqueous hydrochloric acid is added to the residue, and the reaction is refluxed for 15-17 hours. When the decarboxylation reaction is shown to be complete by HPLC, the reaction is cooled to 5° C., diluted with 5 volumes of MTBE and basified to pH 12 with 30% aqueous sodium hydroxide solution. After stirring for 30 minutes, the aqueous layer is extracted further with MTBE, the organic phases are combined and then filtered through celite. The solvent is removed under vacuum, and the residual material is dissolved in 3 volumes of isopropanol. 33% aqueous hydrochloric acid is added to adjust the pH to 4.5 to 6.5. After stirring at least one hour, the product is isolated by filtration at 2° C. followed by vacuum drying. Yield is 65% to 85% over several runs.

A series of experiments is performed to evaluate the range of experimental conditions which produce the product of Example 10 in acceptable yield and purity. It is found that the reaction is successfully performed starting with 1.0 equivalents of the starting material in tolune with 2.20 equivalents of potassium carbonate, and using from 0.18 to 0.22 equivalents of copper iodide, 0.23 to 0.27 equivalents of DBU, and 2.7 to 3.3 equivalents of borane-THF complex.

Example 11: 4-6bR,10aS)-3-methyl-2,3,6b,9,10,10a-hexahydro-1H-pyrido-[3',4':4,5]-pyrrolo[1,2,3-de]quinoxalin-8-(7H)-yl)-1-(4-fluorophenyl)-1-butanone free base

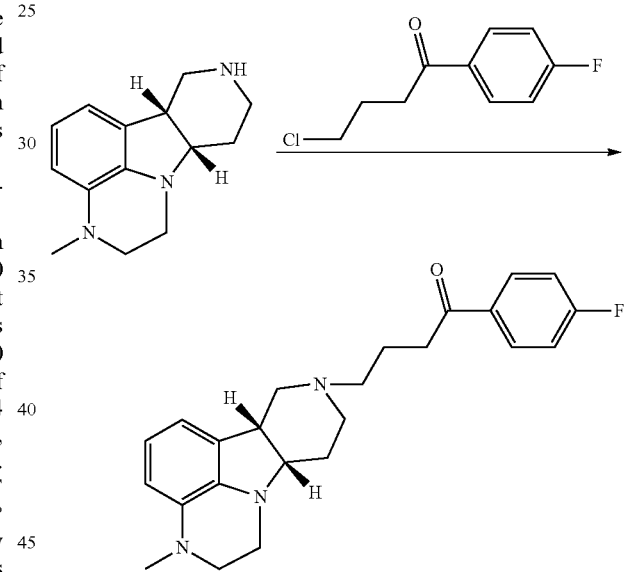

A suspension of (6bR,10aS)-3-methyl-2,3,6b,7,8,9,10,10a-octahydro-1H-pyrido-[3',4':4,5]-pyrrolo[1,2,3-de]quinoxaline (ca. 11.8 g, ca.50 mmol), 4-chloro-4'-fluorobutyrophenone (15.0 g, 74.8 mmol), triethylamine (30 mL, 214 mmol), and potassium iodide (12.6 g, 76 mmol) in dioxane (65 ml) and toluene (65 ml) is heated to reflux for 7 hours. After filtration and evaporation of the solvent, 200 ml of DCM is added. The DCM solution is washed with brine, dried (Na$_2$SO$_4$) and concentrated to approximately 55 ml. The concentrated solution is added dropwise to 600 ml of 0.5N HCl in ether solution. The solid is filtered off and washed with ether and then dissolved in water. The resulting aqueous solution is basified with 2N NaOH and extracted with DCM. The DCM layers are combined, washed with brine (2×200 mL) and dried (Na$_2$SO$_4$). Evaporation of the solvent and chromatography of the residue over silica gel gives 4-((6bR,10aS)-3-methyl-2,3,6b,9,10,10a-hexahydro-1H-pyrido-[3',4':4,5]-pyrrolo[1,2,3-de]quinoxalin-8-(7H)-yl)-1-(4-fluorophenyl)-1-butanone.

Alternative to the use of dioxane, the reaction may be carried out in 3-pentanone. To a 5 L, three-necked, round-bottomed flask equipped with a mechanical stirrer, a N₂ inlet, a reflux condenser, and a temperature probe is charged with 230 g of (6bR,10aS)-3-methyl-2,3,6b,7,8,9,10,10a-octahydro-1H-pyrido-[3',4':4,5]-pyrrolo[1,2,3-de]quinoxaline (1 mol), 249.78 g of KI (1.5 mol, 1.5 eq.), 194.12 g of ⁱPr₂NEt (1.5 mol, 1.5 eq.), 301.76 g of 4-chloro-4'-fluorobutyrophenone (1.5 mol, 1.5 eq.), and 2300 mL of 3-pentanone. The resultant mixture is then heated at 95° C. (internal temperature) for 17 h, and then is checked by HPLC for reaction completion. The batch is then cooled to ca. 10° C. with an ice bath, and then is added 5% NaOH solution (2300 mL). The separated aqueous layer is then extracted with EtOAc (2300 mL). The combined organic layer is filtered through a pad of silica gel (115 g) that is pre-packed with EtOAc. The silica gel is then flushed with EtOAc (2300 mL). The combined filtrate is concentrated under reduced pressure to afford a dark brown liquid. To the liquid is then added EtOAc (2300 mL) and 1.5 N HCl solution (2300 mL). The batch is stirred at RT for ca. 20 min, and layers are cut. The separated organic layer is extracted with 1.5 N HCl solution (1150 mL), and the layers are separated. The combined aqueous layer is cooled in an ice bath to about 10° C. and EtOAc (2300 mL) is added. To the stirring mixture is then added 25% NaOH solution (1000 mL) through an addition funnel while maintaining the internal temperature under 25° C. The resultant mixture is stirred in an ice bath for ca. 20 min, and the layers are separated. The aqueous layer shows a pH of between 11 and 12 by pH paper. The aqueous layer is back extracted with EtOAc (1150 mL), and the layers are cut. The combined organic layer is washed with brine (1150 mL), dried over Na₂SO₄ (230 g), filtered, and concentrated in vacuo to afford 368.8 g of a dark brown liquid. The crude free base is stored under N₂ in a dark cold room.

Example 12: 4-((6bR,10aS)-3-methyl-2,3,6b,9,10,10a-hexahydro-1H-pyrido-[3',4':4,5]-pyrrolo[1,2,3-de]quinoxalin-8-(7H)-yl)-1-(4-fluorophenyl)-1-butanone hydrochloride To a 250 mL 3-neck round bottom flask fitted with a mechanical stirrer, nitrogen inlet and thermocouple, is added 4-((6bR,10aS)-3-methyl-2,3,6b,9,10,10a-hexahydro-1H-pyrido-[3',4':4,5]-pyrrolo[1,2,3-de]quinoxalin-8-(7H)-yl)-1-(4-fluorophenyl)-1-butanone (10 g) in isopropyl acetate (100 mL). The pH is adjusted to about pH 1 by addition of 18 wt % HCl/isopropyl acetate solution (1.8 mL). The reaction is stirred for 1.5 hours under nitrogen at 0-5° C. The suspension is filtered, and the solids are washed with isopropyl acetate (25 mL) to yield solids of 4-((6bR,10aS)-3-methyl-2,3,6b,9,10,10a-hexahydro-1H-pyrido-[3',4':4,5]-pyrrolo[1,2,3-de]quinoxalin-8-(7H)-yl)-1-(4-fluorophenyl)-1-butanone hydrochloride and a clear filtrate. The solids are dried in a vacuum oven at 45° C. to yield 10.77 g (95% purity by HPLC).

Example 13: 4-((6bR,10aS)-3-methyl-2,3,6b,7,8,9,10,10a-octahydro-1H-pyrido-[3',4':4,5]-pyrrolo[1,2,3-de]quinoxaline free base

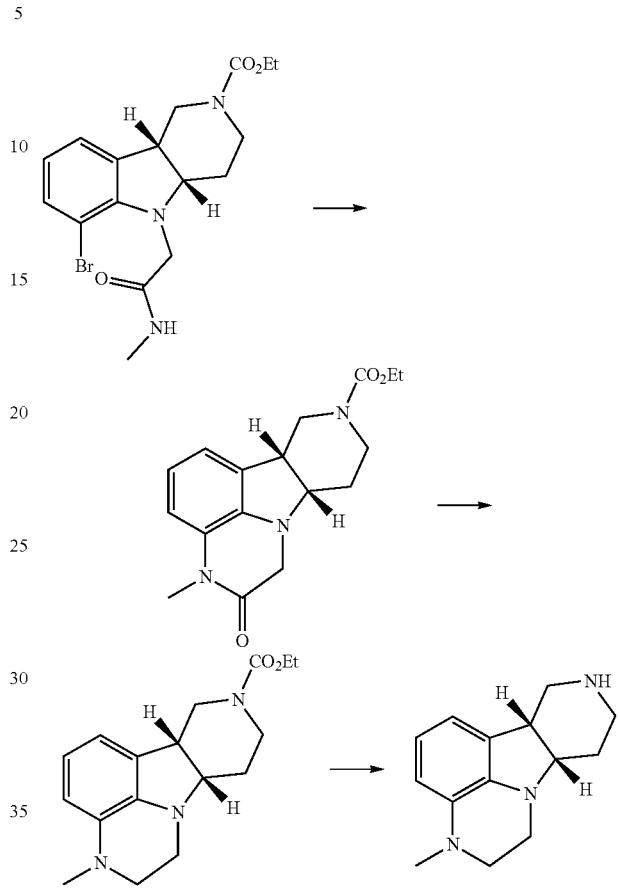

This Example presents a variation of the one-pot three-step conversion, carried out in Example 10, which includes the cyclization of a Compound of Formula 1E to yield a Compound of Formula 1F, the reduction of the amide of the Compound of Formula 1F to yield a Compound of Formula 1H, and the deprotection of the Compound of Formula 1H to yield a Compound of Formula 1I, wherein in each of said Formulas R is methyl, and wherein B is ethoxycarbonyl, but with isolation of the product as a free base instead of hydrochloride salt.

To a 22-L 3-neck round-bottom flask with a mechanical stirrer, nitrogen inlet, thermocouple, dean-stark trap, and condenser is added (4aS,9bR)-ethyl 6-bromo-5-(2-(methylamino)-2-oxoethyl)-3,4,4a,5-tetrahydro-1H-pyrido[4,3-b]indole-2(9bH)-carboxylate (1.45 kg), potassium carbonate powder 325 mesh (1.11 kg), and toluene (2.9 L). The resulting suspension is heated to reflux (110-112° C.) and stirred for 30 to 60 minutes. The reaction is cooled to between 45° C. and 55° C., and then copper (I) iodide (139.4 g) and DBU (139.3 g) are added, and the reaction is stirred for one hour at same temperature. The reaction is then heated back to reflux and maintained for 2.5-5 hours, with reaction progress monitored by HPLC. The reaction is continued until HPLC indicates less than or equal to 3.5% starting material.

A solution of borane-THF complex (1M in THF, 11 L) is added via addition funnel, with cooling provided to maintain the temperature at 15-25° C. The reaction is stirred at same for 12 to 24 hours, with reaction progress monitored by HPLC. The reaction is continued until HPLC indicates less than or equal to 1% of amide intermediate. The reaction mixture is then transferred to a 50 L 3-neck round-bottom flask fitted with a mechanical stirrer, nitrogen inlet and thermocouple. The reaction is cooled to 0-10° C. and is slowly quenched by the addition of methanol (1.45 L) at a rate to control foaming and maintain desired temperature. After the addition is complete, the reaction is stirred for one hour at 0-20° C., and then it is filtered through a 0.5-inch-thick layer of Celite, followed by rinsing with THF (3×2.2 L).

The combined filtrate is concentrated under vacuum (30-50° C. and 60-80 mm Hg) to give an amber oil with fine brown solids. The residue is resuspended in ethyl acetate (4.35 L), filtered through a 0.5-inch-thick layer of Celite, followed by rinsing with ethyl acetate (2×1.45 L). The filtrates are combined and washed with 5 wt % aqueous sodium hydroxide solution (2.18 L), followed by a wash with brine (1.45 L).

A 22 L 3-neck round bottom flask is charged with Florisil (0.435 kg) and ethyl acetate (1 L), stirred for 30 minutes, and then the washed filtrate is added. The resulting suspension is stirred for 14 to 24 hours at 15-25° C. Water (2.2 L) is added, and the mixture is stirred for an additional 2-4 hours. The suspension is filtered, and the filter cake is washed with ethyl acetate (2×1.45 L).

A 22 L 3-neck round bottom flask, fitted with a mechanical stirrer, nitrogen inlet and thermocouple, is charged with water (2.9 L) and concentrated aqueous hydrochloric acid (1.45 L). The solution is cooled to 0-10° C., then the ethyl acetate filtrate is added at a rate to maintain a temperature below 20° C. After stirring for 15 minutes, the layers are separated and the organic layer is concentrated to remove the solvent. The concentrate is added to a 22L 3-beck round bottom flask fitted with a mechanical stirrer, nitrogen inlet and thermocouple and concentrated aqueous hydrochloric acid is added (1.45 L). The solution is stirred for 15 minutes at ambient temperature, then is heated to reflux (99-104° C.) for 24 to 40 hours. Reaction progress is monitored by HPLC.

Upon completion, the reaction mixture is cooled to ambient temperature. Water (2.9 L) and isopropyl acetate (2.9 L) are added. The layers are partitioned, the organic layer is discarded, and isopropyl acetate (4.35 L) is added to the aqueous layer. The aqueous layer is cooled to 0-15° C., and 50 wt % aqueous sodium hydroxide solution is added at a rate to maintain a temperature below 20° C. After addition is complete, the reaction is stirred 10-20 minutes at 0-20° C., then the layers are separated. The aqueous layer is extracted with isopropyl acetate (1.5 L), and the two organic layers are combined and washed once with brine (1.45 L), then dried with sodium sulfate. The filtrate is then stirred for 2-4 hours with Florisil (363 g), filtered, and the filter cake is washed with isopropyl acetate (2×2.9 L). The organic solution is concentrated under vacuum, and the product is recrystallized from n-heptane. Yield is 642 g (76%) of light brown crystalline solids, 99% pure by HPLC.

Example 14: 4-((6bR,10aS)-3-methyl-2,3,6b,7,8,9, 10,10a-octahydro-1H-pyrido-[3',4':4,5]-pyrrolo[1,2, 3-de]quinoxaline hydrochloride To a 2 L three neck round bottom flask equipped with a mechanical stirrer, thermocouple, nitrogen inlet is charged (6bR,10aS)-3-Methyl-2,3,6b,7,8,9,10,10a-octahydro-1H-pyrido[3',4':4,5]pyrrolo[1,2,3-de]quinoxaline (80 g) (free base) and 2-Propanol (360 mL, 4.5 vol). The mixture is stirred for 10 to 30 minutes to give a dark amber solution. Water (80 mL, 0.3488 mol) is added. The mixture is stirred at room temperature for 5 to 15 minutes. The mixture is adjusted to pH 6 to 8 (using pH paper) by portion-wise addition of concentrated HCl from an addition funnel. A thick suspension is formed during addition. Once the desired pH is reached, the mixture is stirred at room temperature for an additional 30 to 60 minutes and is then cooled to 0-5° C. The suspension is diluted with 2-Propanol (40 mL, 0.5 vol) to enable stirring. After filtration, the filter cake is washed successively with a cold (0-5° C.) mixture of water (4 mL, 0.05 vol) and 2-Propanol (76 mL, 0.95 vol) twice, cold (0-5° C.) 2-Propanol (80 mL, 1 vol), cold (0-5° C.) MTBE (80 mL, 1 vol) and MTBE (80 mL, 1 vol). The solid is dried under vacuum at 40-45° C. to give 68.9 g product as a crystalline mono-hydrochloride salt (HPLC purity: 99.18%).

The obtained mono-hydrochloride salt of 4-((6bR,10aS)-3-methyl-2,3,6b,7,8,9,10,10a-octahydro-1H-pyrido-[3',4':4, 5]-pyrrolo[1,2,3-de]quinoxaline hydrochloride is analyzed by X-ray Powder Diffraction (XRPD).

The XRPD Pattern of 4-((6bR,10aS)-3-methyl-2,3,6b,7, 8,9,10,10a-octahydro-1H-pyrido-[3',4':4,5]-pyrrolo[1,2,3-de]quinoxaline mono-hydrochloride salt is shown in FIG. 1.

Figure 2:
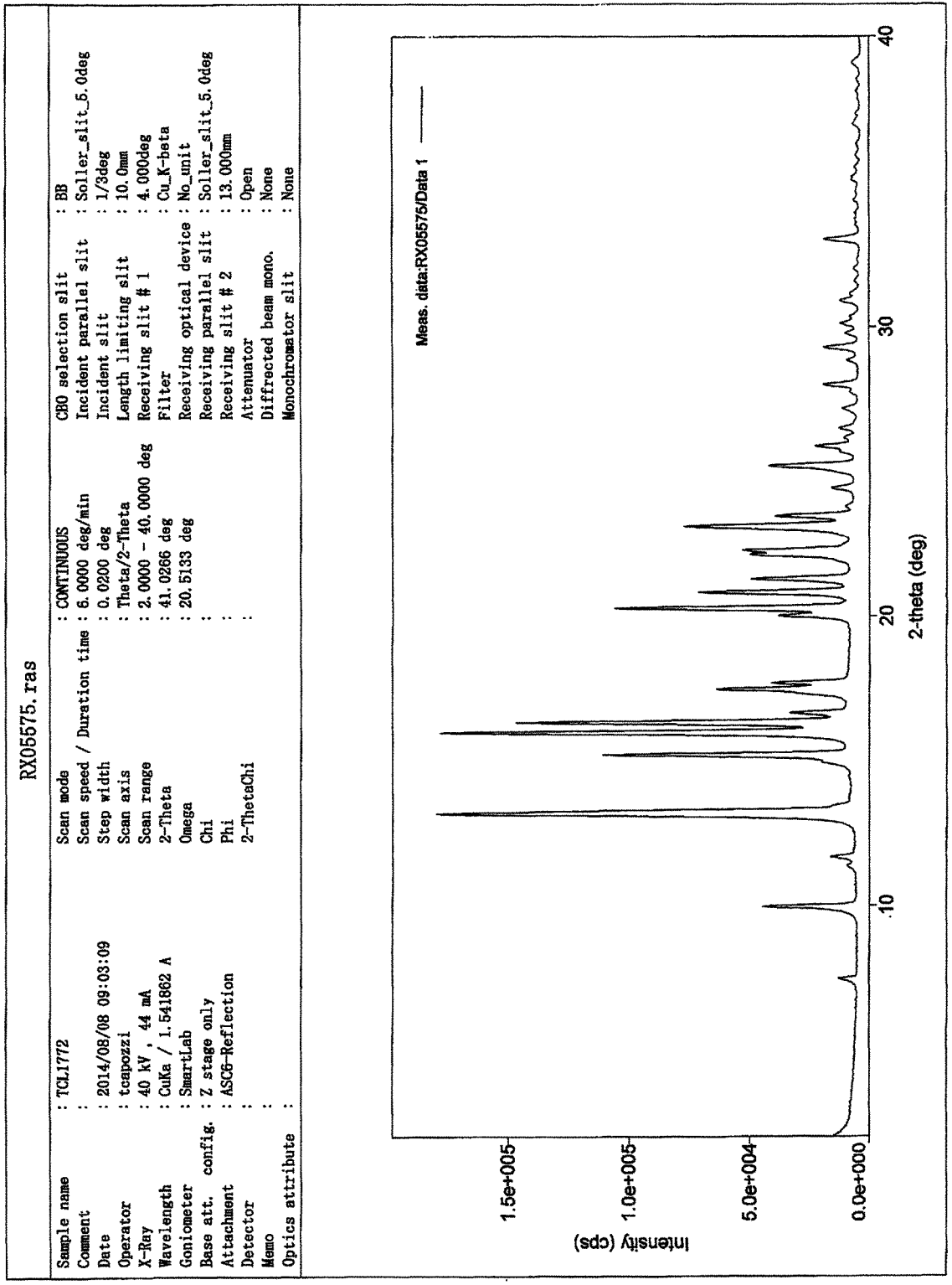
FIG. 2 shows the XRPD Pattern of 4-((6bR,10aS)-3-methyl-2,3,6b,7,8,9,10,10a-octahydro-1H-pyrido-[3',4':4,5]-pyrrolo[1,2,3-de]quinoxaline free base as obtained according to Example 14.

The XRPD Pattern of 4-((6bR,10aS)-3-methyl-2,3,6b,7, 8,9,10,10a-octahydro-1H-pyrido-[3',4':4,5]-pyrrolo[1,2,3-de]quinoxaline free base is shown in FIG. 2.

Example 15: 4-((6bR,10aS)-3-methyl-2,3,6b,9,10, 10a-hexahydro-1H-pyrido-[3',4':4,5]-pyrrolo[1,2,3-de]quinoxalin-8-(7H)-yl)-1-(4-fluorophenyl)-1-butanone tosylate Water, (6bR,10aS)-3-methyl-2,3,6b,7,8,9,10,10a-octahydro-1H-pyrido[3',4':4,5]pyrrolo[1,2,3-de]quinoxaline hydrochloride (1.0 eq.) and isopropyl acetate are mixed and cooled to 0° C. to 30° C. A diluted NaOH solution is added keeping temperature below 0° C. to 30° C. and the mixture is stirred for at least 30 minutes, with the pH maintained at 12 or more. The phases are then separated, and the lower aqueous phase is back-extracted once with isopropyl acetate. The layers are separated again, and the organic extracts are combined and washed with 10% sodium chloride solution. The organic layer is distilled under vacuum to remove isopropyl acetate.

3-Pentanone is then added and vacuum distillation is performed to remove any remaining isopropyl acetate. 3-pentanone is added again and the temperature is then adjusted to 20° C.±10° C. 4-Chloro-4'-fluorobutyrophenone (1.35 to 1.65 eq.) is added. Sodium carbonate (2.7 to 3.3 eq.) and potassium iodide (0.9 to 1.1 eq.) are added. The reaction is purged with nitrogen and then heated to about 73° C. slowly and kept at that temperature for at least 16 hours until the reaction is complete, by HPLC. Once reaction is completed, the reaction is cooled to 30° C. Water is then added and the mixture is stirred for at least 30 minutes. The layers are then separated and the lower aqueous phase is discarded. The organic layer is cooled to 5° C. and washed with a 10% HCl solution (keeping the temperature below 20° C. and at a pH less than 1). The layers are then separated, the aqueous layer is transferred to a clean vessel and the organic layer is discarded. Ethyl acetate is added and the mixture is stirred for 15 minutes, then the layers are separated and the organic layer is discarded.

Ethyl acetate is added to the aqueous layer and the mixture is cooled to 3° C. A 30% NaOH solution is then slowly added maintaining temperature below 20° C. The mixture pH is adjusted to at least 10. After mixing, the phases are separated and the lower aqueous phase is transferred to a clean vessel. Ethyl acetate is added to the aqueous layer and after mixing, the layers are separated and the aqueous layer discarded. The remaining organic layers are combined and washed with a 20% sodium chloride solution. The aqueous layer is then discarded. The organic layer is vacuum distilled to remove solvent, and residue is taken up in MTBE. The organic layer is treated with activated carbon in ethyl acetate for at least 60 minutes at 20° C. The activated carbon is removed by filtration, and the mixture is distilled under vacuum to remove MTBE. Isopropyl alcohol is added, and the mixture is distilled under vacuum to remove any remaining MTBE. Isopropyl alcohol is added again to the reactor, and p-toluenesulfonic acid (0.89 to 1.11 eq.) in isopropyl alcohol is added keeping the temperature at 33° C. Optionally, seeds of the desired tosylate salt product may be added to spur crystallization. The product is isolated by centrifugation. The cake is washed with isopropanol followed by MTBE. The crude product is dried at 45° C. under vacuum. The crude product is added to a reactor with isopropanol and water. The mixture is heated to reflux and stirred at reflux for at least 10 minutes to ensure all solids are in solution. The solution is then filtered and cooled to 65° C., and the solution is optionally seeded with product and/or further cooled to 55° C., then cooled to 0-10° C. and granulated at this temperature for at least 60 minutes. The final product is isolated and washed with isopropanol and MTBE, and then the cake is dried at 45° C. under vacuum. The material is then milled to achieve the desired particle size. In various batches, the yield is found to be 65% to 85% over the steps.

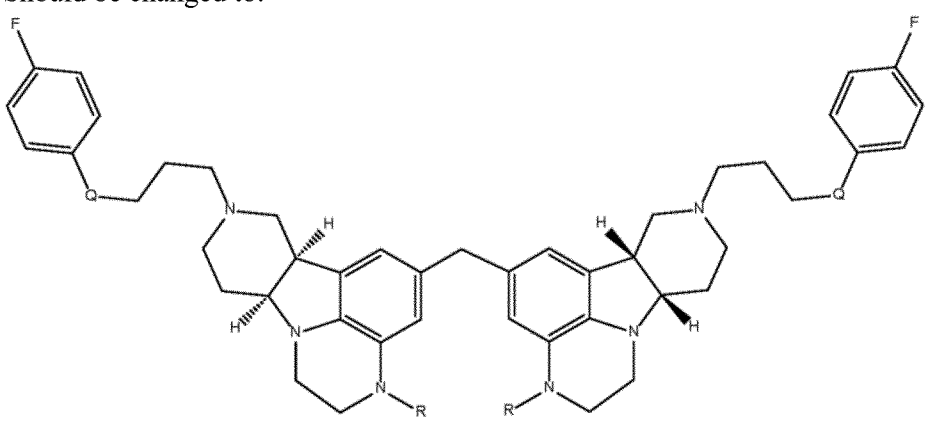

What is claimed is:

1. A method for preparing (A) a compound of Formula 1I or (B) a compound of Formula 1J, as provided below:

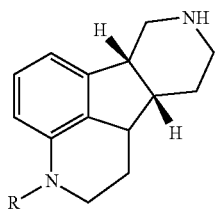

Formula 1I

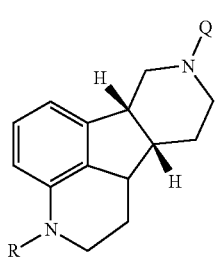

Formula 1J wherein:

R is methyl; and

Q is selected from 4-(4-fluorophenyl)-4-oxobutyl and 3-(4-fluorophenoxy)propyl;

each in free or salt form, comprising the steps of:

(a) reacting a compound of Formula 1E:

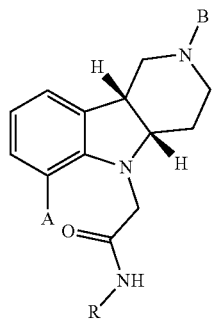

in free or salt form, wherein (i) A is Br; (ii) R is methyl; and (iii) B is an acyl protecting group;

with (i) a transition metal catalyst selected from the group consisting of CuI, CuBr, CuCl, $Cu(OAc)_2$, $Cu_2Cl_2$, $CuBr_2$, $CuSO_4$, $Cu_2SO_4$, and $Cu_2O$, (ii) a carbonate base, (iii) optionally an alkali metal iodide, and (iv) the ligand DBU, in a solvent selected from toluene, xylene, and chlorobenzene, to form an intermediate of Formula 1F:

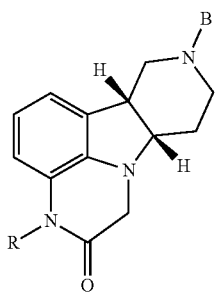

in free or salt form, wherein (i) R is methyl; and (ii) B is an acyl protecting group;

(b) reducing the amide carbonyl of the compound of Formula 1F to yield an intermediate of Formula 1H,

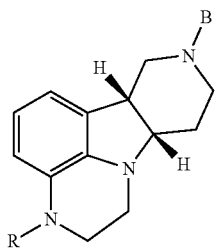

in free or salt form, wherein (i) R is methyl; and (ii) B is an acyl protecting group; and (c) deprotecting the piperidine nitrogen of the compound of Formula 1H to yield the compound of Formula 1I,

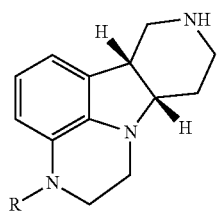

in free or salt form, wherein (i) R is methyl;

and when the product of the method is the compound of Formula 1J, the method further comprising the steps of:
(d) alkylating the piperidine nitrogen of the compound of Formula 1I with a suitable alkylating agent to yield the compound of Formula 1J, in free or salt form; and optionally
(e) converting the compound of Formula 1J in free form to a compound of Formula 1J in salt form.

2. The method according to claim 1, wherein the protecting group B is an acyl group of the formula P-Z, wherein P is C(O) and Z is OR' wherein R' is alkyl or arylalkyl.

3. The method according to claim 2, wherein the protecting group B is ethoxycarbonyl.

4. The method according to claim 1, wherein the transition metal catalyst is CuI.

5. The method according to claim 1, wherein the base of step (a) is a selected from sodium carbonate, potassium carbonate, cesium carbonate, or sodium bicarbonate, and mixtures thereof.

6. The method according to claim 1, wherein step (a) comprises an alkali metal iodide.

7. The method according to claim 1, wherein the reduction of step (b) is accomplished using a reducing agent selected from metal hydrides, boranes and organoboranes.

8. The method according to claim 7, wherein the reducing agent is borane-THF complex.

9. The method according to claim 1, wherein the deprotection step (c) is an aqueous hydrolysis.

10. The method according to claim 9, wherein the aqueous hydrolysis comprises aqueous hydrochloric acid.

11. The method according to claim 1, wherein steps (a), (b) and (c) take place sequentially in a single reaction vessel or a set of connected reaction vessels.

12. The method according to claim 1, wherein the group Q of the compound of Formula 1J is 4-(4-fluorophenyl)-4-oxobutyl and the group R of the compound of Formula 1J is methyl.

13. The method according to claim 1, wherein the compound of Formula 1J is obtained in free base form from step (d), and wherein the method further comprises a step (e) of converting said compound of Formula 1J in free base form into a compound of Formula 1J in acid addition salt form.

14. The method of claim 13, wherein the acid addition salt form is a tosylate salt form.

15. The method according to claim 1, wherein the method provides the compound of Formula 1J in a form having less than about 50 ppm of copper.

16. The method according to claim 2, wherein the protecting group B is selected from t-butoxycarbonyl, phenoxycarbonyl, ethoxycarbonyl, methoxycarbonyl, and an optionally substituted benzyloxycarbonyl.

17. The method according to claim 1, wherein the alkali metal iodide is selected from sodium iodide, potassium iodide, and lithium iodide.

18. The method according to claim 14, wherein the tosylate salt form is selected from mono-tosylate and di-tosylate.

19. The method according to claim 1, wherein the method provides the compound of Formula 1J in a form having less than about 10 ppm of copper.

20. The method according to claim 1, wherein the method provides the compound of Formula 1J in a form having less than about 5 ppm of copper.

21. The method according to claim 1, wherein the transition metal catalyst of step (a) is CuI, wherein the reduction of step (b) is accomplished using the reducing agent borane-THF complex, and wherein the deprotection step (c) is an aqueous hydrolysis comprising aqueous hydrochloric acid.

22. The method according to claim 21, wherein the method provides the compound of Formula 1J in a form having less than about 50 ppm of copper.

23. The method according to claim 1, wherein the solvent of step (a) is toluene.

24. The method according to claim 1, wherein the ligand of step (a) is DBU present in an amount of 0.01 to 0.50 equivalents.

25. The method according to claim 1, wherein the transition metal catalyst of step (a) is CuI present in an amount of 0.10 to 0.30 equivalents, wherein the base of step (a) is potassium carbonate in an amount of 2 to 2.5 equivalents, wherein the ligand of step (a) is DBU present in an amount of 0.01 to 0.50 equivalents, and wherein the solvent of step (a) is toluene.

26. The method according to claim 1, wherein the Compound of Formula 1I is obtained in solid form.

27. The method according to claim 26, wherein the Compound of Formula 1I is obtained in solid crystalline form.

28. The method according to claim 27, wherein the Compound of Formula 1I is obtained in the form of a solid, crystalline hydrochloride salt.

* * * * *

UNITED STATES PATENT AND TRADEMARK OFFICE
CERTIFICATE OF CORRECTION

| | | |
|---|---|---|
| PATENT NO. | : 11,453,670 B2 | Page 1 of 2 |
| APPLICATION NO. | : 16/438163 | |
| DATED | : September 27, 2022 | |
| INVENTOR(S) | : Peng Li and Qiang Zhang | |

It is certified that error appears in the above-identified patent and that said Letters Patent is hereby corrected as shown below:

In the Specification

Column 5, Lines 55-65:

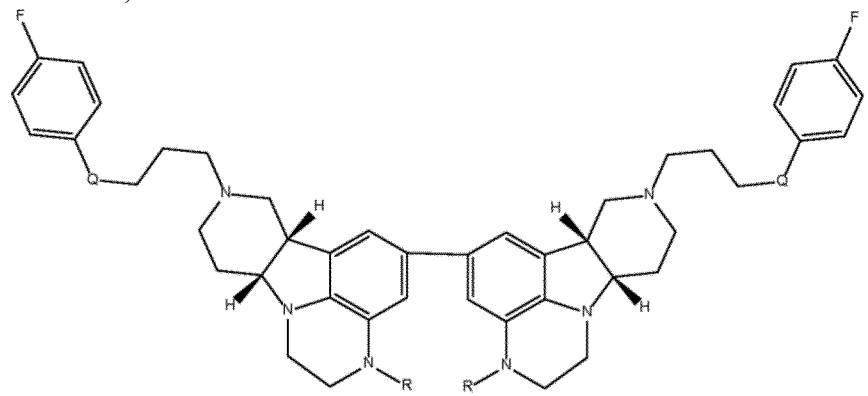

Should be changed to:

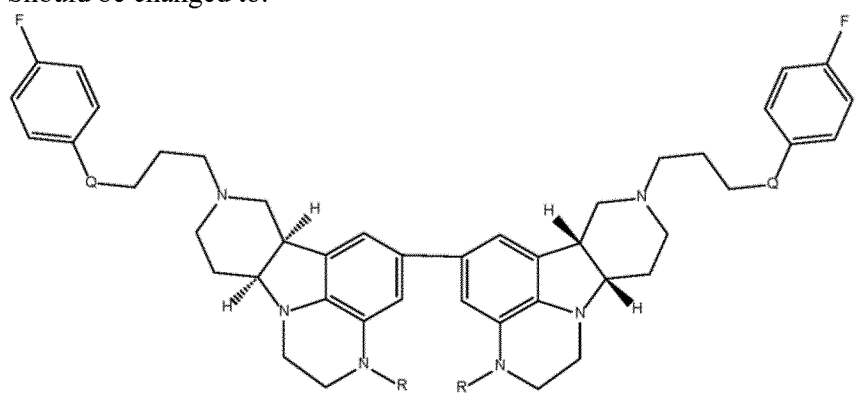

Signed and Sealed this
Ninth Day of July, 2024

Katherine Kelly Vidal
*Director of the United States Patent and Trademark Office*

CERTIFICATE OF CORRECTION (continued)
U.S. Pat. No. 11,453,670 B2

Column 6, Lines 1-15:

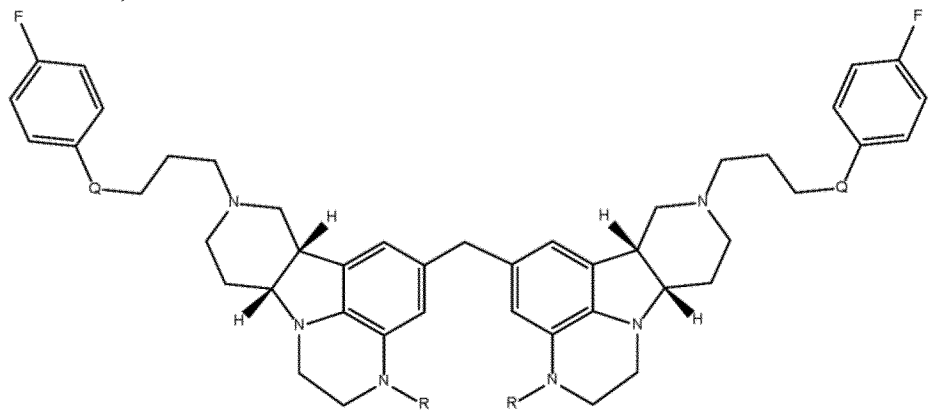

Should be changed to: